(12) United States Patent
Boudreaux et al.

(10) Patent No.: US 10,092,292 B2
(45) Date of Patent: Oct. 9, 2018

(54) STAPLE FORMING FEATURES FOR SURGICAL STAPLING INSTRUMENT

(71) Applicant: Ethicon Endo-Surgery, Inc., Cincinnati, OH (US)

(72) Inventors: Chad P. Boudreaux, Cincinnati, OH (US); Charles J. Scheib, Loveland, OH (US); Douglas B. Hoffman, Harrison, OH (US); Janna B. Volz, Fort Thomas, KY (US); Megan O'Connor, West Chester, OH (US); Adam R. Dunki-Jacobs, Cincinnati, OH (US); Robert P. Kruth, Fort Wayne, IN (US)

(73) Assignee: Ethicon LLC, Guaynabo, PR (US)

( * ) Notice: Subject to any disclaimer, the term of this patent is extended or adjusted under 35 U.S.C. 154(b) by 919 days.

(21) Appl. No.: 13/780,379

(22) Filed: Feb. 28, 2013

(65) Prior Publication Data
US 2014/0239037 A1   Aug. 28, 2014

(51) Int. Cl.
*A61B 17/072* (2006.01)
*A61B 17/00* (2006.01)
*A61B 90/00* (2016.01)

(52) U.S. Cl.
CPC .......... *A61B 17/07207* (2013.01); *A61B 2017/00398* (2013.01); *A61B 2017/00734* (2013.01); *A61B 2017/07264* (2013.01); *A61B 2090/0814* (2016.02)

(58) Field of Classification Search
CPC ....... A61B 2017/07264; A61B 17/0684; B27F 7/19; B25C 5/0278; B25C 5/02
USPC ...................................................... 227/175.1
See application file for complete search history.

(56) References Cited

U.S. PATENT DOCUMENTS

| 66,052 | A | 6/1867 | Smith |
| 662,587 | A | 11/1900 | Blake |
| 951,393 | A | 3/1910 | Hahn |
| 1,306,107 | A | 6/1919 | Elliott |

(Continued)

FOREIGN PATENT DOCUMENTS

| CA | 2458946 | 3/2003 |
| CA | 2512960 | 1/2006 |

(Continued)

OTHER PUBLICATIONS

U.S. Appl. No. 13/780,067, filed Feb. 28, 2013.
(Continued)

*Primary Examiner* — Andrew M Tecco
*Assistant Examiner* — Chinyere Rushing-Tucker
(74) *Attorney, Agent, or Firm* — Frost Brown Todd LLC

(57) ABSTRACT

An end effector for a surgical instrument comprises a first jaw and a second jaw. The first jaw is configured to receive a staple cartridge. The second jaw is movable relative to the first jaw and is configured to provide an anvil for forming staples. The anvil has staple forming pockets. Each staple forming pocket comprises first and second staple forming surface regions configured to receive respective first and second staple legs. The first and second staple forming surface regions each have a respective length that is greater than half of the length of the staple forming pocket. The staple forming surface regions may include convex surfaces that drive staple legs laterally. The pocket minimizes re-entry of staple leg tips into tissue.

11 Claims, 45 Drawing Sheets

(56) References Cited

U.S. PATENT DOCUMENTS

| | | |
|---|---|---|
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,441,096 A | 5/1948 | Happe |
| 2,526,902 A | 10/1950 | Rublee |
| 2,674,149 A | 4/1954 | Benson |
| 2,804,848 A | 9/1957 | O'Farrell et al. |
| 2,808,482 A | 10/1957 | Zanichkowsky et al. |
| 2,853,074 A | 9/1958 | Olson |
| 3,032,769 A | 5/1962 | Palmer |
| 3,075,062 A | 1/1963 | Iaccarino |
| 3,078,465 A | 2/1963 | Bobrov |
| 3,166,072 A | 1/1965 | Sullivan, Jr. |
| 3,266,494 A | 8/1966 | Brownrigg et al. |
| 3,269,630 A | 8/1966 | Fleischer |
| 3,357,296 A | 12/1967 | Lefever |
| 3,490,675 A | 1/1970 | Green et al. |
| 3,551,987 A | 1/1971 | Wilkinson |
| 3,598,943 A | 8/1971 | Barrett |
| 3,643,851 A | 2/1972 | Green et al. |
| 3,662,939 A | 5/1972 | Bryan |
| 3,664,860 A | 5/1972 | Kamiya et al. |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,797,364 A | 3/1974 | Schulze |
| 3,819,100 A | 6/1974 | Noiles et al. |
| 3,821,919 A | 7/1974 | Knohl |
| 3,841,474 A | 10/1974 | Maier |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| RE28,932 E | 8/1976 | Noiles et al. |
| 4,060,089 A | 11/1977 | Noiles |
| 4,129,059 A | 12/1978 | Van Eck |
| 4,213,562 A | 7/1980 | Garrett et al. |
| 4,250,436 A | 2/1981 | Weissman |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,402,445 A | 9/1983 | Green |
| 4,408,692 A | 10/1983 | Sigel et al. |
| 4,415,112 A | 11/1983 | Green |
| 4,428,376 A | 1/1984 | Mericle |
| 4,429,695 A | 2/1984 | Green |
| 4,434,796 A | 3/1984 | Karapetian et al. |
| 4,442,964 A | 4/1984 | Becht |
| 4,451,743 A | 5/1984 | Suzuki et al. |
| 4,454,887 A | 6/1984 | Kruger |
| 4,467,805 A | 8/1984 | Fukuda |
| 4,475,679 A | 10/1984 | Fleury, Jr. |
| 4,485,816 A | 12/1984 | Krumme |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,548,202 A | 10/1985 | Duncan |
| 4,565,189 A | 1/1986 | Mabuchi |
| 4,566,620 A | 1/1986 | Preen et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,671,445 A | 6/1987 | Barker et al. |
| 4,676,245 A | 6/1987 | Fukuda |
| 4,693,248 A | 9/1987 | Failla |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,741,336 A | 3/1988 | Failla et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,834,720 A | 2/1989 | Blinkhorn |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,890,613 A | 1/1990 | Golden et al. |
| 4,892,244 A | 1/1990 | Fox et al. |
| 4,915,100 A | 4/1990 | Green |
| 4,930,503 A | 6/1990 | Pruitt |
| 4,930,674 A | 6/1990 | Barak |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |

(56) References Cited

U.S. PATENT DOCUMENTS

| | | |
|---|---|---|
| 5,014,899 A | 5/1991 | Presty et al. |
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,156,315 A | 10/1992 | Green et al. |
| 5,156,614 A | 10/1992 | Green et al. |
| 5,158,567 A | 10/1992 | Green |
| D330,699 S | 11/1992 | Gill |
| 5,136,598 A | 11/1992 | Peters et al. |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,195,968 A | 3/1993 | Lundquist et al. |
| 5,197,648 A | 3/1993 | Gingold |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A * | 6/1993 | Takase .............. A61B 17/072 227/178.1 |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,256,366 A | 11/1993 | Reydel et al. |
| 5,258,009 A * | 11/1993 | Conners ............. A61B 17/0644 606/219 |
| 5,258,012 A | 11/1993 | Luscombe et al. |
| 5,260,637 A | 11/1993 | Pizzi |
| 5,263,629 A | 11/1993 | Trumbull et al. |
| 5,263,973 A | 11/1993 | Cook |
| 5,269,622 A | 12/1993 | Phillipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,281,216 A | 1/1994 | Klicek |
| 5,282,806 A | 2/1994 | Haber et al. |
| 5,282,829 A | 2/1994 | Hermes |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,318,221 A | 6/1994 | Green et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,395 A | 8/1994 | Jarrett et al. |
| 5,342,396 A | 8/1994 | Cook |
| 5,344,060 A | 9/1994 | Gravener et al. |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,510 A | 10/1994 | Luscombe et al. |
| 5,359,231 A | 10/1994 | Flowers et al. |
| D352,780 S | 11/1994 | Glaeser et al. |
| 5,360,428 A | 11/1994 | Hutchinson, Jr. |
| 5,364,003 A | 11/1994 | Williamson, IV |
| 5,366,134 A | 11/1994 | Green et al. |
| 5,366,479 A | 11/1994 | McGarry et al. |
| 5,370,645 A | 12/1994 | Klicek et al. |
| 5,372,596 A | 12/1994 | Klicek et al. |
| 5,372,602 A | 12/1994 | Burke |
| 5,374,277 A | 12/1994 | Hassler |
| 5,379,933 A | 1/1995 | Green et al. |
| 5,381,782 A | 1/1995 | DeLaRama et al. |
| 5,382,247 A | 1/1995 | Cimino et al. |
| 5,382,782 A | 1/1995 | DeLaRama et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,312 A | 3/1995 | Desai |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,344 A | 4/1995 | Williamson et al. |
| 5,407,293 A | 4/1995 | Crainich |
| 5,409,498 A | 4/1995 | Braddock et al. |
| 5,411,508 A | 5/1995 | Bessler et al. |
| 5,413,267 A | 5/1995 | Solyntjes et al. |
| 5,413,268 A | 5/1995 | Green et al. |
| 5,413,272 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,421,829 A | 6/1995 | Olichney et al. |
| 5,422,567 A | 6/1995 | Matsunaga |
| 5,423,809 A | 6/1995 | Klicek |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,438,302 A | 8/1995 | Goble |

(56) References Cited

U.S. PATENT DOCUMENTS

| | | |
|---|---|---|
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,494 A | 8/1995 | Ortiz |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,452,836 A | 9/1995 | Huitema et al. |
| 5,452,837 A | 9/1995 | Williamson, IV et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A * | 1/1996 | Blewett ............ A61B 17/072 227/175.1 |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,543,119 A | 8/1996 | Sutter et al. |
| 5,547,117 A | 8/1996 | Hamblin et al. |
| 5,549,621 A | 8/1996 | Bessler et al. |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,789 A | 11/1996 | Bell et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,450 A | 3/1997 | Zvenyatsky et al. |
| 5,609,285 A | 3/1997 | Grant et al. |
| 5,611,709 A | 3/1997 | McAnulty |
| 5,613,966 A | 3/1997 | Makower et al. |
| 5,618,294 A | 4/1997 | Aust et al. |
| 5,618,303 A | 4/1997 | Marlow et al. |
| 5,618,307 A | 4/1997 | Donlon et al. |
| 5,620,289 A | 4/1997 | Curry |
| 5,620,452 A | 4/1997 | Yoon |
| 5,624,452 A | 4/1997 | Yates |
| 5,626,587 A | 5/1997 | Bishop et al. |
| 5,628,446 A | 5/1997 | Geiste et al. |
| 5,628,743 A | 5/1997 | Cimino |
| 5,630,539 A | 5/1997 | Plyley et al. |
| 5,630,540 A | 5/1997 | Blewett |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher |

(56) References Cited

U.S. PATENT DOCUMENTS

| | | |
|---|---|---|
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | heard |
| 5,658,300 A | 8/1997 | Bito et al. |
| 5,660,546 A | 8/1997 | Shafer |
| 5,662,258 A | 9/1997 | Knodel et al. |
| 5,662,260 A | 9/1997 | Yoon |
| 5,662,662 A | 9/1997 | Bishop et al. |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,693,051 A | 12/1997 | Schulze et al. |
| 5,695,494 A | 12/1997 | Becker |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,747,985 A | 5/1998 | Lee et al. |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,806,676 A | 9/1998 | Wasgien |
| 5,807,378 A | 9/1998 | Jensen et al. |
| 5,807,393 A | 9/1998 | Williamson, IV et al. |
| 5,809,441 A | 9/1998 | McKee |
| 5,810,811 A | 9/1998 | Yates et al. |
| 5,810,855 A | 9/1998 | Rayburn |
| 5,813,813 A | 9/1998 | Daum et al. |
| 5,814,055 A | 9/1998 | Knodel et al. |
| 5,814,057 A | 9/1998 | Oi et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,132 A | 12/1998 | Ilvento |
| 5,846,254 A | 12/1998 | Schulze et al. |
| 5,849,011 A | 12/1998 | Jones et al. |
| 5,855,311 A | 1/1999 | Hamblin et al. |
| 5,855,583 A | 1/1999 | Wang et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |

(56) References Cited

U.S. PATENT DOCUMENTS

| | | |
|---|---|---|
| 5,878,938 A | 3/1999 | Bittner et al. |
| 5,891,160 A | 4/1999 | Williamson, IV et al. |
| 5,893,506 A | 4/1999 | Powell |
| 5,894,979 A | 4/1999 | Powell |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,693 A | 5/1999 | Dicesare et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,948,030 A | 9/1999 | Miller et al. |
| 5,951,552 A | 9/1999 | Long et al. |
| 5,951,574 A | 9/1999 | Stefanchik et al. |
| 5,954,259 A | 9/1999 | Viola et al. |
| 5,964,774 A | 10/1999 | McKean et al. |
| 5,971,916 A | 10/1999 | Koren |
| 5,988,479 A | 11/1999 | Palmer |
| 6,003,517 A | 12/1999 | Sheffield et al. |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,017,322 A | 1/2000 | Snoke et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,039,733 A | 3/2000 | Buysse et al. |
| 6,039,734 A | 3/2000 | Goble |
| 6,045,560 A | 4/2000 | McKean et al. |
| 6,050,472 A | 4/2000 | Shibata |
| 6,053,390 A | 4/2000 | Green et al. |
| 6,053,922 A | 4/2000 | Krause et al. |
| 6,056,746 A | 5/2000 | Goble et al. |
| 6,063,097 A | 5/2000 | Oi et al. |
| 6,063,098 A | 5/2000 | Houser et al. |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,077,286 A | 6/2000 | Cuschieri et al. |
| 6,079,606 A | 6/2000 | Milliman et al. |
| 6,082,577 A | 7/2000 | Coates et al. |
| 6,083,234 A | 7/2000 | Nicholas et al. |
| 6,083,242 A | 7/2000 | Cook |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,132,368 A | 10/2000 | Cooper |
| 6,139,546 A | 10/2000 | Koenig et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,162,208 A | 12/2000 | Hipps |
| 6,165,175 A | 12/2000 | Wampler et al. |
| 6,165,184 A | 12/2000 | Verdura et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,776 B1 | 1/2001 | Adams et al. |
| 6,181,105 B1 | 1/2001 | Cutolo et al. |
| 6,193,129 B1 | 2/2001 | Bittner et al. |
| 6,197,042 B1 | 3/2001 | Ginn et al. |
| 6,202,914 B1 | 3/2001 | Geiste et al. |
| 6,214,028 B1 | 4/2001 | Yoon et al. |
| 6,220,368 B1 | 4/2001 | Ark et al. |
| 6,223,835 B1 | 5/2001 | Habedank et al. |
| 6,228,081 B1 | 5/2001 | Goble |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,723 B1 | 6/2001 | Heim et al. |
| 6,249,076 B1 | 6/2001 | Madden et al. |
| 6,250,532 B1 | 6/2001 | Green et al. |
| 6,258,107 B1 | 7/2001 | Balazs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,306,134 B1 | 10/2001 | Goble et al. |
| 6,309,403 B1 | 10/2001 | Minor et al. |
| 6,315,184 B1 | 11/2001 | Whitman |
| 6,320,123 B1 | 11/2001 | Reimers |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,334,860 B1 | 1/2002 | Dorn |
| 6,336,926 B1 | 1/2002 | Goble |
| 6,338,737 B1 | 1/2002 | Toledano |
| 6,346,077 B1 | 2/2002 | Taylor et al. |
| 6,352,503 B1 | 3/2002 | Matsui et al. |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,373,152 B1 | 4/2002 | Wang et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,409,724 B1 | 6/2002 | Penny et al. |
| H2037 H | 7/2002 | Yates et al. |
| 6,416,486 B1 | 7/2002 | Wampler |
| 6,416,509 B1 | 7/2002 | Goble et al. |
| 6,419,695 B1 | 7/2002 | Gabbay |
| RE37,814 E | 8/2002 | Allgeyer |
| 6,436,097 B1 | 8/2002 | Nardella |
| 6,436,107 B1 | 8/2002 | Wang et al. |

(56) References Cited

U.S. PATENT DOCUMENTS

| | | |
|---|---|---|
| 6,436,110 B2 | 8/2002 | Bowman et al. |
| 6,436,122 B1 | 8/2002 | Frank et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,450,391 B1 | 9/2002 | Kayan et al. |
| 6,468,275 B1 | 10/2002 | Wampler et al. |
| 6,471,106 B1 | 10/2002 | Reining |
| 6,482,200 B2 | 11/2002 | Shippert |
| 6,485,490 B2 | 11/2002 | Wampler et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,543,456 B1 | 4/2003 | Freeman |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,588,643 B2 | 7/2003 | Bolduc et al. |
| 6,589,164 B1 | 7/2003 | Flaherty |
| 6,592,597 B2 | 7/2003 | Grant et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,605,078 B2 | 8/2003 | Adams |
| 6,605,669 B2 | 8/2003 | Awo et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema et al. |
| 6,641,528 B2 | 11/2003 | Torii |
| 6,644,532 B2 | 11/2003 | Green et al. |
| 6,648,816 B2 | 11/2003 | Irion et al. |
| D484,243 S | 12/2003 | Ryan et al. |
| D484,595 S | 12/2003 | Ryan et al. |
| D484,596 S | 12/2003 | Ryan et al. |
| 6,656,193 B2 | 12/2003 | Grant et al. |
| 6,666,875 B1 | 12/2003 | Sakurai et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,692,507 B2 | 2/2004 | Pugsley et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,736,854 B2 | 5/2004 | Vadurri et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,768 B2 | 7/2004 | Spencer |
| 6,758,846 B2 | 7/2004 | Goble et al. |
| 6,761,685 B2 | 7/2004 | Adams et al. |
| 6,767,352 B2 | 7/2004 | Field et al. |
| 6,767,356 B2 | 7/2004 | Kanner et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,821,284 B2 | 11/2004 | Sturtz et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,843,403 B2 | 1/2005 | Whitman |
| 6,843,789 B2 | 1/2005 | Goble |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,905,057 B2 | 6/2005 | Swayze et al. |
| 6,905,497 B2 | 6/2005 | Truckai et al. |
| 6,913,608 B2 | 7/2005 | Liddicoat et al. |
| 6,913,613 B2 | 7/2005 | Schwarz et al. |
| 6,923,803 B2 | 8/2005 | Goble |
| 6,925,849 B2 | 8/2005 | Jairam |
| 6,929,641 B2 | 8/2005 | Goble et al. |
| 6,931,830 B2 | 8/2005 | Liao |
| 6,936,042 B2 | 8/2005 | Wallace et al. |
| 6,939,358 B2 | 9/2005 | Palacios et al. |
| 6,942,662 B2 | 9/2005 | Goble et al. |

(56) References Cited

U.S. PATENT DOCUMENTS

| | | |
|---|---|---|
| 6,945,444 B2 | 9/2005 | Gresham et al. |
| 6,953,138 B1 * | 10/2005 | Dworak ............ B21D 13/02 227/154 |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,018,390 B2 | 3/2006 | Turovskiy et al. |
| 7,025,743 B2 | 4/2006 | mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,868 B2 | 5/2006 | Greene et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,508 B2 | 6/2006 | Shelton, IV et al. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,070,083 B2 | 7/2006 | Jankowski |
| 7,070,559 B2 | 7/2006 | Adams et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,097,089 B2 | 8/2006 | Marczyk |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,182,239 B1 | 2/2007 | Myers |
| 7,188,758 B2 | 3/2007 | Viola et al. |
| 7,195,627 B2 | 3/2007 | Amoah et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,213,736 B2 | 5/2007 | Wales |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,258,262 B2 | 8/2007 | Mastri et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,994 B2 | 10/2007 | Goble |
| 7,282,048 B2 | 10/2007 | Goble et al. |
| 7,282,189 B2 | 10/2007 | Zauderer |
| 7,295,907 B2 | 11/2007 | Lu et al. |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |

(56) References Cited

U.S. PATENT DOCUMENTS

| | | |
|---|---|---|
| 7,303,108 B2 | 12/2007 | Shelton, IV et al. |
| 7,303,556 B2 | 12/2007 | Metzger |
| 7,308,998 B2 | 12/2007 | Mastri et al. |
| 7,322,975 B2 | 1/2008 | Goble et al. |
| 7,324,572 B2 | 1/2008 | Chang |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,334,717 B2 | 2/2008 | Rethy et al. |
| 7,335,199 B2 | 2/2008 | Goble et al. |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,388,217 B2 | 6/2008 | Buschbeck et al. |
| 7,394,630 B2 | 7/2008 | Ker et al. |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,076 B2 | 8/2008 | Racenet et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,418,078 B2 | 8/2008 | Blanz et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,455,676 B2 | 11/2008 | Holsten et al. |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,608 B2 | 1/2009 | Smith |
| 7,481,347 B2 | 1/2009 | Roy |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,985 B2 | 5/2009 | Takemoto et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,577,717 B2 | 8/2009 | Smith |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,624,902 B2 | 12/2009 | Marczyk et al. |
| 7,624,903 B2 | 12/2009 | Green et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,641,092 B2 | 1/2010 | Kruszynski et al. |
| 7,641,093 B2 | 1/2010 | Doll et al. |
| 7,644,848 B2 | 1/2010 | Swayze et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,674,263 B2 | 3/2010 | Ryan |
| 7,682,307 B2 | 3/2010 | Danitz et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,695,485 B2 | 4/2010 | Whitman et al. |
| 7,699,204 B2 | 4/2010 | Viola |
| 7,699,846 B2 | 4/2010 | Ryan |
| 7,699,859 B2 | 4/2010 | Bombard et al. |
| 7,708,180 B2 | 5/2010 | Murray et al. |

(56) References Cited

U.S. PATENT DOCUMENTS

| | | |
|---|---|---|
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton et al. |
| 7,721,934 B2 | 5/2010 | Shelton, IV et al. |
| 7,721,936 B2 | 5/2010 | Shalton, IV et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,775 B2 | 8/2010 | Shelton, IV et al. |
| 7,771,396 B2 | 8/2010 | Stefanchik et al. |
| 7,772,720 B2 | 8/2010 | McGee et al. |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,803,151 B2 | 9/2010 | Whitman |
| 7,806,891 B2 | 10/2010 | Nowlin et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,592 B2 | 11/2010 | Bettuchi et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailey et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,533 B2 | 12/2010 | Marczyk et al. |
| 7,845,534 B2 | 12/2010 | Viola et al. |
| 7,845,537 B2 | 12/2010 | Shelton, IV et al. |
| 7,846,149 B2 | 12/2010 | Jankowski |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,887,530 B2 | 2/2011 | Zemlok et al. |
| 7,891,531 B1 | 2/2011 | Ward |
| 7,896,877 B2 | 3/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,902 B2 | 3/2011 | Huitema et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,377 B2 | 4/2011 | Fuchs et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,927,328 B2 | 4/2011 | Orszulak et al. |
| 7,931,630 B2 | 5/2011 | Shelton, IV et al. |
| 7,938,307 B2 | 5/2011 | Bettuchi |
| 7,941,435 B2 | 5/2011 | Kao et al. |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,959,050 B2 | 6/2011 | Smith et al. |
| 7,959,051 B2 | 6/2011 | Smith et al. |
| 7,963,963 B2 | 6/2011 | Francischelli et al. |
| 7,966,799 B2 | 6/2011 | Morgan et al. |
| 7,967,180 B2 | 6/2011 | Scirica |
| 7,972,298 B2 | 7/2011 | Wallace et al. |
| 7,980,443 B2 | 7/2011 | Scheib et al. |
| 7,988,015 B2 | 8/2011 | Mason, II et al. |
| 7,992,757 B2 | 8/2011 | Wheeler et al. |
| 7,997,469 B2 | 8/2011 | Olson et al. |
| 8,002,784 B2 | 8/2011 | Jinno et al. |
| 8,002,795 B2 | 8/2011 | Beetel |
| 8,011,550 B2 | 9/2011 | Aranyi et al. |
| 8,011,551 B2 | 9/2011 | Marczyk et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,883 B2 | 10/2011 | Stopek |
| 8,028,885 B2 | 10/2011 | Smith et al. |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,043,328 B2 | 10/2011 | Hahnen et al. |
| 8,056,787 B2 | 11/2011 | Boudreaux et al. |
| 8,062,330 B2 | 11/2011 | Prommersberger et al. |
| 8,066,167 B2 | 11/2011 | Measamer et al. |
| D650,074 S | 12/2011 | Hunt et al. |
| 8,070,743 B2 | 12/2011 | Kagan et al. |
| 8,083,119 B2 | 12/2011 | Prommersberger |
| 8,083,120 B2 | 12/2011 | Shelton, IV et al. |

(56) References Cited

U.S. PATENT DOCUMENTS

| | | |
|---|---|---|
| 8,084,001 B2 | 12/2011 | Burns et al. |
| 8,091,756 B2 | 1/2012 | Viola |
| 8,097,017 B2 | 1/2012 | Viola |
| 8,100,310 B2 | 1/2012 | Zemlok |
| 8,108,072 B2 | 1/2012 | Zhao et al. |
| 8,113,410 B2 | 2/2012 | Hall et al. |
| 8,123,103 B2 | 2/2012 | Milliman |
| 8,123,767 B2 | 2/2012 | Bauman et al. |
| 8,128,645 B2 | 3/2012 | Sonnenschein et al. |
| 8,136,712 B2 | 3/2012 | Zingman |
| 8,141,762 B2 | 3/2012 | Bedi et al. |
| 8,141,763 B2 | 3/2012 | Milliman |
| 8,152,041 B2 | 4/2012 | Kostrzewski |
| 8,157,145 B2 | 4/2012 | Shelton, IV et al. |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,138 B2 | 4/2012 | Bettenhausen et al. |
| 8,167,185 B2 | 5/2012 | Shelton, IV et al. |
| 8,167,895 B2 | 5/2012 | D'Agostino et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,180,458 B2 | 5/2012 | Kane et al. |
| 8,186,555 B2 | 5/2012 | Shelton, IV et al. |
| 8,186,560 B2 | 5/2012 | Hess et al. |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,211,125 B2 | 7/2012 | Spivey |
| 8,215,531 B2 | 7/2012 | Shelton, IV et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,225,799 B2 | 7/2012 | Bettuchi et al. |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,901 B2 | 8/2012 | Stopek |
| 8,254,391 B2 | 9/2012 | Orban, III et al. |
| 8,256,654 B2 | 9/2012 | Bettuchi et al. |
| 8,267,300 B2 | 9/2012 | Boudreaux |
| 8,269,121 B2 | 9/2012 | Smith |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,285,367 B2 | 10/2012 | Hyde et al. |
| 8,286,845 B2 | 10/2012 | Perry et al. |
| 8,286,846 B2 | 10/2012 | Smith et al. |
| 8,287,561 B2 | 10/2012 | Nunez et al. |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,677 B2 | 10/2012 | Wiesner et al. |
| 8,308,040 B2 | 11/2012 | Huang et al. |
| 8,308,042 B2 | 11/2012 | Aranyi |
| 8,308,046 B2 | 11/2012 | Prommersberger |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,074 B2 | 11/2012 | Ortiz et al. |
| 8,322,455 B2 | 12/2012 | Shelton, IV et al. |
| 8,322,589 B2 | 12/2012 | Boudreaux |
| 8,328,062 B2 | 12/2012 | Viola |
| 8,328,064 B2 | 12/2012 | Racenet et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,348,127 B2 | 1/2013 | Marczyk |
| 8,348,129 B2 | 1/2013 | Bedi et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,299 B2 | 1/2013 | Zemlok et al. |
| 8,365,973 B1 | 2/2013 | White et al. |
| 8,365,976 B2 | 2/2013 | Hess et al. |
| 8,366,787 B2 | 2/2013 | Brown et al. |
| 8,371,491 B2 | 2/2013 | Huitema et al. |
| 8,371,492 B2 | 2/2013 | Aranyi et al. |
| 8,372,094 B2 | 2/2013 | Bettuchi et al. |
| 8,397,971 B2 | 3/2013 | Yates et al. |
| 8,403,198 B2 | 3/2013 | Sorrentino et al. |
| 8,403,950 B2 | 3/2013 | Palmer et al. |
| 8,408,439 B2 | 4/2013 | Huang et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,740 B2 | 4/2013 | Shelton, IV et al. |
| 8,424,741 B2 | 4/2013 | McGuckin, Jr. et al. |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,914 B2 | 6/2013 | Laurent et al. |
| 8,454,640 B2 | 6/2013 | Johnston et al. |
| 8,459,520 B2 | 6/2013 | Giordano et al. |
| 8,459,525 B2 | 6/2013 | Yates et al. |
| 8,464,923 B2 | 6/2013 | Shelton, IV |
| 8,464,925 B2 | 6/2013 | Hull et al. |
| 8,474,677 B2 | 7/2013 | Woodard, Jr. et al. |
| 8,479,969 B2 | 7/2013 | Shelton, IV et al. |
| 8,485,412 B2 | 7/2013 | Shelton, IV et al. |
| 8,485,413 B2 | 7/2013 | Scheib et al. |
| 8,491,603 B2 | 7/2013 | Yeung et al. |
| 8,499,993 B2 | 8/2013 | Shelton, IV et al. |
| 8,517,239 B2 | 8/2013 | Scheib et al. |
| 8,517,243 B2 | 8/2013 | Giordano et al. |
| 8,517,244 B2 | 8/2013 | Shelton, IV et al. |
| 8,532,747 B2 | 9/2013 | Nock et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,550,984 B2 | 10/2013 | Takemoto |
| 8,561,870 B2 | 10/2013 | Baxter, III et al. |
| 8,567,656 B2 | 10/2013 | Shelton, IV et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,579,176 B2 | 11/2013 | Smith et al. |
| 8,584,919 B2 | 11/2013 | Hueil et al. |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,602,287 B2 | 12/2013 | Yates et al. |
| 8,602,288 B2 | 12/2013 | Shelton, IV et al. |
| 8,608,044 B2 | 12/2013 | Hueil et al. |
| 8,608,045 B2 | 12/2013 | Smith et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,631,987 B2 | 1/2014 | Shelton, IV et al. |
| 8,631,993 B2 | 1/2014 | Kostrzewski |

(56) References Cited

U.S. PATENT DOCUMENTS

| | | | |
|---|---|---|---|
| 8,632,462 B2 | 1/2014 | Yoo et al. | |
| 8,632,535 B2 | 1/2014 | Shelton, IV et al. | |
| 8,636,187 B2 | 1/2014 | Hueil et al. | |
| 8,636,193 B2 * | 1/2014 | Whitman | A61B 17/068 227/176.1 |
| 8,636,736 B2 | 1/2014 | Yates et al. | |
| 8,646,674 B2 | 2/2014 | Schulte et al. | |
| 8,652,120 B2 | 2/2014 | Giordano et al. | |
| 8,657,174 B2 | 2/2014 | Yates et al. | |
| 8,657,814 B2 | 2/2014 | Werneth et al. | |
| 8,668,130 B2 | 3/2014 | Hess et al. | |
| 8,672,207 B2 | 3/2014 | Shelton, IV et al. | |
| 8,672,208 B2 | 3/2014 | Hess et al. | |
| 8,672,951 B2 | 3/2014 | Smith et al. | |
| 8,679,154 B2 | 3/2014 | Smith et al. | |
| 8,679,156 B2 | 3/2014 | Smith et al. | |
| 8,684,253 B2 | 4/2014 | Giordano et al. | |
| 2002/0022836 A1 | 2/2002 | Goble et al. | |
| 2002/0029036 A1 | 3/2002 | Goble et al. | |
| 2002/0117534 A1 | 8/2002 | Green et al. | |
| 2002/0134811 A1 | 9/2002 | Napier et al. | |
| 2003/0093103 A1 | 5/2003 | Malackowski et al. | |
| 2003/0139741 A1 | 7/2003 | Goble et al. | |
| 2003/0153908 A1 | 8/2003 | Goble et al. | |
| 2003/0195387 A1 | 10/2003 | Kortenbach et al. | |
| 2003/0205029 A1 | 11/2003 | Chapolini et al. | |
| 2003/0216732 A1 | 11/2003 | Truckai et al. | |
| 2004/0006335 A1 | 1/2004 | Garrison | |
| 2004/0006340 A1 | 1/2004 | Latterell et al. | |
| 2004/0030333 A1 | 2/2004 | Goble | |
| 2004/0034357 A1 | 2/2004 | Beane et al. | |
| 2004/0044364 A1 | 3/2004 | Devries et al. | |
| 2004/0068161 A1 | 4/2004 | Couvillon, Jr. | |
| 2004/0068307 A1 | 4/2004 | Goble | |
| 2004/0070369 A1 | 4/2004 | Sakakibara | |
| 2004/0078037 A1 | 4/2004 | Batchelor | |
| 2004/0093024 A1 | 5/2004 | Lousararian et al. | |
| 2004/0101822 A1 | 5/2004 | Wiesner et al. | |
| 2004/0108357 A1 | 6/2004 | Milliman et al. | |
| 2004/0115022 A1 | 6/2004 | Albertson et al. | |
| 2004/0116952 A1 | 6/2004 | Sakurai et al. | |
| 2004/0147909 A1 | 7/2004 | Johnston et al. | |
| 2004/0164123 A1 | 8/2004 | Racenet et al. | |
| 2004/0167572 A1 | 8/2004 | Roth et al. | |
| 2004/0181219 A1 | 9/2004 | Goble et al. | |
| 2004/0193189 A1 | 9/2004 | Kortenbach et al. | |
| 2004/0222268 A1 | 11/2004 | Bilotti et al. | |
| 2004/0243151 A1 | 12/2004 | Demmy et al. | |
| 2004/0243163 A1 | 12/2004 | Casiano et al. | |
| 2004/0254566 A1 | 12/2004 | Plicchi et al. | |
| 2004/0260315 A1 | 12/2004 | Dell et al. | |
| 2004/0267310 A1 | 12/2004 | Racenet et al. | |
| 2005/0032511 A1 | 2/2005 | Malone et al. | |
| 2005/0054946 A1 | 3/2005 | Krzyzanowski | |
| 2005/0059997 A1 | 3/2005 | Bauman et al. | |
| 2005/0070929 A1 | 3/2005 | Dalessandro et al. | |
| 2005/0085693 A1 | 4/2005 | Belson et al. | |
| 2005/0090817 A1 | 4/2005 | Phan | |
| 2005/0103819 A1 | 5/2005 | Racenet et al. | |
| 2005/0119669 A1 | 6/2005 | Demmy | |
| 2005/0124855 A1 | 6/2005 | Jaffe et al. | |
| 2005/0131173 A1 | 6/2005 | McDaniel et al. | |
| 2005/0131211 A1 | 6/2005 | Bayley et al. | |
| 2005/0131390 A1 | 6/2005 | Heinrich et al. | |
| 2005/0131436 A1 | 6/2005 | Johnston et al. | |
| 2005/0131457 A1 | 6/2005 | Douglas et al. | |
| 2005/0137454 A1 | 6/2005 | Saadat et al. | |
| 2005/0137455 A1 | 6/2005 | Ewers et al. | |
| 2005/0143759 A1 | 6/2005 | Kelly | |
| 2005/0154258 A1 | 7/2005 | Tartaglia et al. | |
| 2005/0165419 A1 | 7/2005 | Sauer et al. | |
| 2005/0169974 A1 | 8/2005 | Tenerz et al. | |
| 2005/0171522 A1 | 8/2005 | Christopherson | |
| 2005/0177181 A1 | 8/2005 | Kagan et al. | |
| 2005/0182298 A1 | 8/2005 | Likeda et al. | |
| 2005/0187545 A1 | 8/2005 | Hooven et al. | |
| 2005/0189397 A1 | 9/2005 | Jankowski | |
| 2005/0203550 A1 | 9/2005 | Laufer et al. | |
| 2005/0216055 A1 | 9/2005 | Scirica et al. | |
| 2005/0228224 A1 | 10/2005 | Okada et al. | |
| 2005/0261676 A1 | 11/2005 | Hall et al. | |
| 2005/0263563 A1 | 12/2005 | Racenet et al. | |
| 2005/0267455 A1 | 12/2005 | Eggers et al. | |
| 2006/0004407 A1 | 1/2006 | Hiles et al. | |
| 2006/0008787 A1 | 1/2006 | Hayman et al. | |
| 2006/0015009 A1 | 1/2006 | Jaffe et al. | |
| 2006/0020336 A1 | 1/2006 | Liddicoat | |
| 2006/0025812 A1 | 2/2006 | Shelton, IV | |
| 2006/0025813 A1 | 2/2006 | Shelton et al. | |
| 2006/0047275 A1 | 3/2006 | Goble | |
| 2006/0049229 A1 | 3/2006 | Milliman et al. | |
| 2006/0052825 A1 | 3/2006 | Ransick et al. | |
| 2006/0064086 A1 | 3/2006 | Odom | |
| 2006/0079735 A1 | 4/2006 | Martone et al. | |
| 2006/0086032 A1 | 4/2006 | Valencic et al. | |
| 2006/0100643 A1 | 5/2006 | Laufer et al. | |
| 2006/0111711 A1 | 5/2006 | Goble | |
| 2006/0111723 A1 | 5/2006 | Chapolini et al. | |
| 2006/0142772 A1 | 6/2006 | Ralph et al. | |
| 2006/0161185 A1 | 7/2006 | Saadat et al. | |
| 2006/0173470 A1 | 8/2006 | Oray et al. | |
| 2006/0180634 A1 | 8/2006 | Shelton, IV et al. | |
| 2006/0217729 A1 | 9/2006 | Leskridge et al. | |
| 2006/0244460 A1 | 11/2006 | Weaver | |
| 2006/0258904 A1 | 11/2006 | Stefanchik et al. | |
| 2006/0259073 A1 | 11/2006 | Miyamoto et al. | |
| 2006/0264929 A1 | 11/2006 | Goble et al. | |
| 2006/0271042 A1 | 11/2006 | Latterell et al. | |
| 2006/0271102 A1 | 11/2006 | Bosshard et al. | |
| 2006/0289602 A1 | 12/2006 | Wales et al. | |
| 2006/0291981 A1 | 12/2006 | Viola et al. | |
| 2007/0027468 A1 | 2/2007 | Wales et al. | |
| 2007/0027472 A1 | 2/2007 | Hiles et al. | |
| 2007/0055219 A1 | 3/2007 | Whitman et al. | |
| 2007/0073341 A1 | 3/2007 | Smith | |
| 2007/0078484 A1 | 4/2007 | Talarico et al. | |
| 2007/0084897 A1 | 4/2007 | Shelton, IV et al. | |
| 2007/0102472 A1 | 5/2007 | Shelton, IV | |
| 2007/0106113 A1 | 5/2007 | Ravo | |
| 2007/0106317 A1 | 5/2007 | Shelton, IV et al. | |
| 2007/0118175 A1 | 5/2007 | Butler et al. | |
| 2007/0135803 A1 | 6/2007 | Belson | |
| 2007/0170225 A1 | 7/2007 | Shelton, IV et al. | |
| 2007/0173813 A1 | 7/2007 | Odom | |
| 2007/0175949 A1 | 8/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175955 A1 | 8/2007 | Shelton, IV et al. | |
| 2007/0194079 A1 | 8/2007 | Hueil et al. | |
| 2007/0194082 A1 | 8/2007 | Morgan et al. | |
| 2007/0203510 A1 | 8/2007 | Bettuchi | |
| 2007/0213750 A1 | 9/2007 | Weadock | |
| 2007/0221700 A1 | 9/2007 | Ortiz et al. | |
| 2007/0225562 A1 | 9/2007 | Spivey et al. | |
| 2007/0239028 A1 | 10/2007 | Houser et al. | |
| 2007/0243227 A1 | 10/2007 | Gertner | |
| 2007/0246505 A1 | 10/2007 | Pace-Floridia et al. | |
| 2007/0286892 A1 | 12/2007 | Herzberg et al. | |
| 2008/0015598 A1 | 1/2008 | Prommersberger | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0030170 A1 | 2/2008 | Dacquay et al. | |
| 2008/0078800 A1 | 4/2008 | Hess et al. | |
| 2008/0078802 A1 | 4/2008 | Hess et al. | |
| 2008/0082114 A1 | 4/2008 | McKenna et al. | |
| 2008/0082125 A1 | 4/2008 | Murray et al. | |
| 2008/0082126 A1 | 4/2008 | Murray et al. | |
| 2008/0083813 A1 | 4/2008 | Zemlok et al. | |
| 2008/0114385 A1 | 5/2008 | Byrum et al. | |
| 2008/0128469 A1 | 6/2008 | Dalessandro et al. | |
| 2008/0129253 A1 | 6/2008 | Shiue et al. | |
| 2008/0140115 A1 | 6/2008 | Stopek | |

(56) References Cited

U.S. PATENT DOCUMENTS

| | | |
|---|---|---|
| 2008/0169328 A1 | 7/2008 | Shelton, IV |
| 2008/0169329 A1 | 7/2008 | Shelton, IV et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0183193 A1 | 7/2008 | Omori et al. |
| 2008/0197167 A1 | 8/2008 | Viola et al. |
| 2008/0200835 A1 | 8/2008 | Monson et al. |
| 2008/0200949 A1 | 8/2008 | Hiles et al. |
| 2008/0228029 A1 | 9/2008 | Mikkaichi et al. |
| 2008/0255413 A1 | 10/2008 | Zemlok et al. |
| 2008/0262654 A1 | 10/2008 | Omori et al. |
| 2008/0287944 A1 | 11/2008 | Pearson et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012534 A1 | 1/2009 | Madhani et al. |
| 2009/0012556 A1 | 1/2009 | Boudreaux et al. |
| 2009/0020958 A1 | 1/2009 | Soul |
| 2009/0054908 A1 | 2/2009 | Zand et al. |
| 2009/0088774 A1 | 4/2009 | Swarup et al. |
| 2009/0090763 A1 | 4/2009 | Zemlok et al. |
| 2009/0112229 A1 | 4/2009 | Omori et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209946 A1 | 8/2009 | Swayze et al. |
| 2009/0213685 A1 | 8/2009 | Mak et al. |
| 2009/0242610 A1 | 10/2009 | Shelton, IV et al. |
| 2009/0255974 A1 | 10/2009 | Viola |
| 2009/0292283 A1 | 11/2009 | Odom |
| 2009/0308907 A1 | 12/2009 | Nalagatla et al. |
| 2010/0023024 A1 | 1/2010 | Zeiner et al. |
| 2010/0069942 A1 | 3/2010 | Shelton, IV |
| 2010/0076475 A1 | 3/2010 | Yates et al. |
| 2010/0133317 A1 | 6/2010 | Shelton, IV et al. |
| 2010/0145146 A1 | 6/2010 | Melder |
| 2010/0147922 A1 | 6/2010 | Olson |
| 2010/0163598 A1 | 7/2010 | Belzer |
| 2010/0179382 A1 | 7/2010 | Shelton, IV et al. |
| 2010/0193566 A1 | 8/2010 | Scheib et al. |
| 2010/0222901 A1 | 9/2010 | Swayze et al. |
| 2010/0230465 A1 | 9/2010 | Smith et al. |
| 2010/0258611 A1 | 10/2010 | Smith et al. |
| 2010/0294829 A1 | 11/2010 | Giordano et al. |
| 2010/0305552 A1 | 12/2010 | Shelton, IV et al. |
| 2010/0312261 A1 | 12/2010 | Suzuki et al. |
| 2010/0331880 A1 | 12/2010 | Stopek |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0060363 A1 | 3/2011 | Hess et al. |
| 2011/0068148 A1 | 3/2011 | Hall et al. |
| 2011/0084113 A1* | 4/2011 | Bedi .................. A61B 17/0644 227/178.1 |
| 2011/0087276 A1 | 4/2011 | Bedi et al. |
| 2011/0087279 A1 | 4/2011 | Shah et al. |
| 2011/0114697 A1 | 5/2011 | Baxter, III et al. |
| 2011/0114700 A1 | 5/2011 | Baxter, III et al. |
| 2011/0125176 A1 | 5/2011 | Yates et al. |
| 2011/0125177 A1 | 5/2011 | Yates et al. |
| 2011/0132964 A1 | 6/2011 | Weisenburgh, II et al. |
| 2011/0144430 A1 | 6/2011 | Spivey et al. |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0174861 A1 | 7/2011 | Shelton, IV et al. |
| 2011/0192882 A1 | 8/2011 | Hess et al. |
| 2011/0226837 A1* | 9/2011 | Baxter, III ......... A61B 17/0644 227/175.1 |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295295 A1 | 12/2011 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0071711 A1 | 3/2012 | Shelton, IV et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0138660 A1 | 6/2012 | Shelton, IV et al. |
| 2012/0160721 A1 | 6/2012 | Shelton, IV et al. |
| 2012/0175399 A1 | 6/2012 | Shelton et al. |
| 2012/0187179 A1 | 7/2012 | Gleiman |
| 2012/0199076 A1 | 8/2012 | Shelton, IV et al. |
| 2012/0199632 A1 | 8/2012 | Spivey et al. |
| 2012/0203247 A1 | 8/2012 | Shelton, IV et al. |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |

(56) References Cited

U.S. PATENT DOCUMENTS

| | | |
|---|---|---|
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0238823 A1 | 9/2012 | Hagerty et al. |
| 2012/0238824 A1 | 9/2012 | Widenhouse et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 9/2012 | Widenhouse et al. |
| 2012/0253298 A1 | 9/2012 | Henderson et al. |
| 2012/0283707 A1 | 11/2012 | Giordano et al. |
| 2012/0292367 A1 | 11/2012 | Morgan et al. |
| 2012/0298719 A1 | 11/2012 | Shelton, IV et al. |
| 2012/0298722 A1 | 11/2012 | Hess et al. |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0012931 A1 | 1/2013 | Spivey et al. |
| 2013/0012957 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0037596 A1 | 2/2013 | Bear et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0079814 A1 | 3/2013 | Hess et al. |
| 2013/0146642 A1 | 6/2013 | Shelton, IV et al. |
| 2013/0146643 A1 | 6/2013 | Schmid et al. |
| 2013/0172929 A1 | 7/2013 | Hess et al. |
| 2013/0175321 A1 | 7/2013 | Shelton, IV et al. |
| 2013/0181030 A1 | 7/2013 | Hess et al. |
| 2013/0214030 A1 | 8/2013 | Aronhalt et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0327809 A1 | 12/2013 | Shelton, IV et al. |
| 2014/0097227 A1 | 4/2014 | Aronhalt et al. |

FOREIGN PATENT DOCUMENTS

| | | |
|---|---|---|
| CA | 2514274 | 1/2006 |
| CN | 2488482 | 5/2002 |
| CN | 1634601 | 7/2005 |
| CN | 1868411 | 11/2006 |
| CN | 1915180 | 2/2007 |
| CN | 101011286 | 8/2007 |
| CN | 101095621 | 1/2008 |
| DE | 273689 | 5/1914 |
| DE | 1775926 | 1/1972 |
| DE | 3036217 | 4/1982 |
| DE | 3210466 | 9/1983 |
| DE | 9412228 | 9/1994 |
| DE | 19509116 | 9/1996 |
| DE | 19851291 | 1/2000 |
| DE | 19924311 | 11/2000 |
| DE | 69328576 | 1/2001 |
| DE | 10052679 | 5/2001 |
| DE | 20112837 | 10/2001 |
| DE | 20121753 | 4/2003 |
| DE | 10314072 | 10/2004 |
| DE | 202007003114 | 6/2007 |
| EP | 0122046 | 10/1984 |
| EP | 0070230 | 10/1985 |
| EP | 0156774 | 10/1985 |
| EP | 0387980 | 10/1985 |
| EP | 0033548 | 5/1986 |
| EP | 0129442 | 11/1987 |
| EP | 0276104 | 7/1988 |
| EP | 0178941 | 1/1991 |
| EP | 0248844 | 1/1993 |
| EP | 0545029 | 6/1993 |
| EP | 0277959 | 10/1993 |
| EP | 0233940 | 11/1993 |
| EP | 0261230 | 11/1993 |
| EP | 0639349 | 2/1994 |
| EP | 0324636 | 3/1994 |
| EP | 0593920 | 4/1994 |
| EP | 0594148 | 4/1994 |
| EP | 0427949 | 6/1994 |
| EP | 0523174 | 6/1994 |
| EP | 0600182 | 6/1994 |
| EP | 0310431 | 11/1994 |
| EP | 0375302 | 11/1994 |
| EP | 0376562 | 11/1994 |
| EP | 0630612 | 12/1994 |
| EP | 0634144 | 1/1995 |
| EP | 0646356 | 4/1995 |
| EP | 0646357 | 4/1995 |
| EP | 0653189 | 5/1995 |
| EP | 0669104 | 8/1995 |
| EP | 0511470 | 10/1995 |
| EP | 0679367 | 11/1995 |
| EP | 0392547 | 12/1995 |
| EP | 0685204 | 12/1995 |
| EP | 0364216 | 1/1996 |
| EP | 0699418 | 3/1996 |
| EP | 0702937 | 3/1996 |
| EP | 0705571 | 4/1996 |
| EP | 0711611 | 5/1996 |
| EP | 0484677 | 6/1996 |
| EP | 0541987 | 7/1996 |
| EP | 0667119 | 7/1996 |
| EP | 0708618 | 3/1997 |
| EP | 0770355 | 5/1997 |
| EP | 0503662 | 6/1997 |
| EP | 0447121 | 7/1997 |
| EP | 0625077 | 7/1997 |
| EP | 0633749 | 8/1997 |
| EP | 0710090 | 8/1997 |
| EP | 0578425 | 9/1997 |
| EP | 0625335 | 11/1997 |
| EP | 0552423 | 1/1998 |
| EP | 0592244 | 1/1998 |
| EP | 0648476 | 1/1998 |
| EP | 0649290 | 3/1998 |
| EP | 0599618 | 9/1998 |
| EP | 0676173 | 9/1998 |

(56) References Cited

FOREIGN PATENT DOCUMENTS

| | | |
|---|---|---|
| EP | 0678007 | 9/1998 |
| EP | 0603472 | 11/1998 |
| EP | 0605351 | 11/1998 |
| EP | 0878169 | 11/1998 |
| EP | 0879742 | 11/1998 |
| EP | 0695144 | 12/1998 |
| EP | 0722296 | 12/1998 |
| EP | 2765794 | 1/1999 |
| EP | 0760230 | 2/1999 |
| EP | 0623316 | 3/1999 |
| EP | 0650701 | 3/1999 |
| EP | 0537572 | 6/1999 |
| EP | 0923907 | 6/1999 |
| EP | 0843906 | 3/2000 |
| EP | 0552050 | 5/2000 |
| EP | 0833592 | 5/2000 |
| EP | 0830094 | 9/2000 |
| EP | 1034747 | 9/2000 |
| EP | 1034748 | 9/2000 |
| EP | 0694290 | 11/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1090592 | 4/2001 |
| EP | 1095627 | 5/2001 |
| EP | 1256318 | 5/2001 |
| EP | 0806914 | 9/2001 |
| EP | 0768840 | 12/2001 |
| EP | 0908152 | 1/2002 |
| EP | 0872213 | 5/2002 |
| EP | 0862386 | 6/2002 |
| EP | 0949886 | 9/2002 |
| EP | 1238634 | 9/2002 |
| EP | 0858295 | 12/2002 |
| EP | 0656188 | 1/2003 |
| EP | 1284120 | 2/2003 |
| EP | 1287788 | 3/2003 |
| EP | 0717966 | 4/2003 |
| EP | 0869742 | 5/2003 |
| EP | 0829235 | 6/2003 |
| EP | 0887046 | 7/2003 |
| EP | 0852480 | 8/2003 |
| EP | 0891154 | 9/2003 |
| EP | 0813843 | 10/2003 |
| EP | 0873089 | 10/2003 |
| EP | 0856326 | 11/2003 |
| EP | 1374788 | 1/2004 |
| EP | 0741996 | 2/2004 |
| EP | 0814712 | 2/2004 |
| EP | 1402837 | 3/2004 |
| EP | 0705570 | 4/2004 |
| EP | 0959784 | 4/2004 |
| EP | 1407719 | 4/2004 |
| EP | 1086713 | 5/2004 |
| EP | 0996378 | 6/2004 |
| EP | 1426012 | 6/2004 |
| EP | 0833593 | 7/2004 |
| EP | 1442694 | 8/2004 |
| EP | 0888749 | 9/2004 |
| EP | 0959786 | 9/2004 |
| EP | 1459695 | 9/2004 |
| EP | 1473819 | 11/2004 |
| EP | 1477119 | 11/2004 |
| EP | 1479345 | 11/2004 |
| EP | 1479347 | 11/2004 |
| EP | 1479348 | 11/2004 |
| EP | 0754437 | 12/2004 |
| EP | 1025807 | 12/2004 |
| EP | 1001710 | 1/2005 |
| EP | 1520521 | 4/2005 |
| EP | 1520523 | 4/2005 |
| EP | 1520525 | 4/2005 |
| EP | 1522264 | 4/2005 |
| EP | 1523942 | 4/2005 |
| EP | 1550408 | 7/2005 |
| EP | 1557129 | 7/2005 |
| EP | 1064883 | 8/2005 |
| EP | 1067876 | 8/2005 |
| EP | 0870473 | 9/2005 |
| EP | 1157666 | 9/2005 |
| EP | 0880338 | 10/2005 |
| EP | 1158917 | 11/2005 |
| EP | 1344498 | 11/2005 |
| EP | 1330989 | 12/2005 |
| EP | 0771176 | 1/2006 |
| EP | 1621138 | 2/2006 |
| EP | 1621139 | 2/2006 |
| EP | 1621141 | 2/2006 |
| EP | 1621145 | 2/2006 |
| EP | 1621151 | 2/2006 |
| EP | 1034746 | 3/2006 |
| EP | 1632191 | 3/2006 |
| EP | 1065981 | 5/2006 |
| EP | 1082944 | 5/2006 |
| EP | 1652481 | 5/2006 |
| EP | 1382303 | 6/2006 |
| EP | 1253866 | 7/2006 |
| EP | 1032318 | 8/2006 |
| EP | 1045672 | 8/2006 |
| EP | 1617768 | 8/2006 |
| EP | 1693015 | 8/2006 |
| EP | 1400214 | 9/2006 |
| EP | 1702567 | 9/2006 |
| EP | 1129665 | 11/2006 |
| EP | 1400206 | 11/2006 |
| EP | 1721568 | 11/2006 |
| EP | 1256317 | 12/2006 |
| EP | 1285633 | 12/2006 |
| EP | 1728473 | 12/2006 |
| EP | 1728475 | 12/2006 |
| EP | 1479346 | 1/2007 |
| EP | 1484024 | 1/2007 |
| EP | 1754445 | 2/2007 |
| EP | 1759812 | 3/2007 |
| EP | 1767163 | 3/2007 |
| EP | 1769756 | 4/2007 |
| EP | 1769758 | 4/2007 |
| EP | 1581128 | 5/2007 |
| EP | 1785097 | 5/2007 |
| EP | 1790293 | 5/2007 |
| EP | 1800610 | 6/2007 |
| EP | 1300117 | 8/2007 |
| EP | 1813199 | 8/2007 |
| EP | 1813201 | 8/2007 |
| EP | 1813202 | 8/2007 |
| EP | 1813203 | 8/2007 |
| EP | 1813207 | 8/2007 |
| EP | 1813209 | 8/2007 |
| EP | 1487359 | 10/2007 |
| EP | 1599146 | 10/2007 |
| EP | 2110083 | 10/2007 |
| EP | 1857057 | 11/2007 |
| EP | 1402821 | 12/2007 |
| EP | 1872727 | 1/2008 |
| EP | 1671593 | 2/2008 |
| EP | 1839596 | 2/2008 |
| EP | 1897502 | 3/2008 |
| EP | 1330201 | 6/2008 |
| EP | 1702568 | 7/2008 |
| EP | 1943955 | 7/2008 |
| EP | 1943957 | 7/2008 |
| EP | 1943964 | 7/2008 |
| EP | 1943976 | 7/2008 |
| EP | 1593337 | 8/2008 |
| EP | 1970014 | 9/2008 |
| EP | 1980213 | 10/2008 |
| EP | 1759645 | 11/2008 |
| EP | 1990014 | 11/2008 |
| EP | 1693008 | 12/2008 |
| EP | 1759640 | 12/2008 |
| EP | 2000102 | 12/2008 |

(56) References Cited

FOREIGN PATENT DOCUMENTS

| | | |
|---|---|---|
| EP | 2008595 | 12/2008 |
| EP | 1736104 | 3/2009 |
| EP | 1749486 | 3/2009 |
| EP | 2039316 | 3/2009 |
| EP | 1721576 | 4/2009 |
| EP | 1733686 | 4/2009 |
| EP | 2044890 | 4/2009 |
| EP | 1550409 | 6/2009 |
| EP | 1550413 | 6/2009 |
| EP | 1745748 | 8/2009 |
| EP | 2090237 | 8/2009 |
| EP | 2090244 | 8/2009 |
| EP | 2090245 | 8/2009 |
| EP | 2090256 | 8/2009 |
| EP | 2095777 | 9/2009 |
| EP | 2110082 | 10/2009 |
| EP | 1813208 | 11/2009 |
| EP | 2116195 | 11/2009 |
| EP | 1607050 | 12/2009 |
| EP | 1815804 | 12/2009 |
| EP | 1875870 | 12/2009 |
| EP | 1566150 | 4/2010 |
| EP | 1813206 | 4/2010 |
| EP | 1769754 | 6/2010 |
| EP | 1535565 | 10/2010 |
| EP | 1702570 | 10/2010 |
| EP | 1785098 | 10/2010 |
| EP | 2005896 | 10/2010 |
| EP | 2030578 | 11/2010 |
| EP | 1627605 | 12/2010 |
| EP | 1813205 | 6/2011 |
| EP | 2090243 | 6/2011 |
| EP | 1785102 | 1/2012 |
| FR | 999646 | 2/1952 |
| FR | 1112936 | 3/1956 |
| FR | 2598905 | 11/1987 |
| FR | 2765794 | 1/1999 |
| GB | 939929 | 10/1963 |
| GB | 1210522 | 10/1970 |
| GB | 1217159 | 12/1970 |
| GB | 1339394 | 12/1973 |
| GB | 2109241 | 6/1983 |
| GB | 2272159 | 5/1994 |
| GB | 2284242 | 5/1995 |
| GB | 2336214 | 10/1999 |
| GB | 2425903 | 11/2006 |
| JP | S 58500053 | 1/1983 |
| JP | 61-98249 | 5/1986 |
| JP | 63-203149 | 8/1988 |
| JP | 3-12126 | 1/1991 |
| JP | 5-212039 | 8/1993 |
| JP | H05-237126 A | 9/1993 |
| JP | 067357 | 1/1994 |
| JP | 0751273 | 2/1995 |
| JP | H07124166 | 5/1995 |
| JP | 8033641 | 2/1996 |
| JP | 8229050 | 9/1996 |
| JP | 2000033071 | 2/2000 |
| JP | 2000171730 | 6/2000 |
| JP | 2000287987 | 10/2000 |
| JP | 2000325303 | 11/2000 |
| JP | 2001-514541 | 9/2001 |
| JP | 2001286477 | 10/2001 |
| JP | 2002143078 | 5/2002 |
| JP | 2002369820 | 12/2002 |
| JP | 2003-500153 | 1/2003 |
| JP | 2004-344663 | 12/2004 |
| JP | 2005-028149 | 2/2005 |
| JP | 2005505322 | 2/2005 |
| JP | 2005103293 | 4/2005 |
| JP | 2005131164 | 5/2005 |
| JP | 2005131173 | 5/2005 |
| JP | 2005131211 | 5/2005 |
| JP | 2005131212 | 5/2005 |
| JP | 2005137423 | 6/2005 |
| JP | 2005152416 | 6/2005 |
| JP | 2005-523105 | 8/2005 |
| JP | 2005524474 | 8/2005 |
| JP | 2005131163 | 5/2006 |
| JP | 2006-281405 | 10/2006 |
| JP | 2006334412 | 12/2006 |
| JP | 2008283749 | 11/2008 |
| RU | 2008830 | 3/1994 |
| RU | 2141279 | 11/1999 |
| RU | 2187249 | 8/2002 |
| RU | 2225170 | 3/2004 |
| SU | 189517 | 1/1967 |
| SU | 328636 | 9/1972 |
| SU | 886900 | 12/1981 |
| SU | 1009439 | 4/1983 |
| SU | 1333319 | 8/1987 |
| SU | 1377053 | 2/1988 |
| SU | 1561964 | 5/1990 |
| SU | 1722476 | 3/1992 |
| SU | 1752361 | 8/1992 |
| WO | WO 82/02824 | 9/1982 |
| WO | WO 91/15157 | 10/1991 |
| WO | WO 92/20295 | 11/1992 |
| WO | WO 92/21300 | 12/1992 |
| WO | WO 93/08755 | 5/1993 |
| WO | WO 93/13718 | 7/1993 |
| WO | WO 93/14690 | 8/1993 |
| WO | WO 93/15648 | 8/1993 |
| WO | WO 93/15850 | 8/1993 |
| WO | WO 93/19681 | 10/1993 |
| WO | WO 94/00060 | 1/1994 |
| WO | WO 94/11057 | 5/1994 |
| WO | WO 94/12108 | 6/1994 |
| WO | WO 94/18893 | 9/1994 |
| WO | WO 94/22378 | 10/1994 |
| WO | WO 94/23659 | 10/1994 |
| WO | WO 95/02369 | 1/1995 |
| WO | WO 95/03743 | 2/1995 |
| WO | WO 95/06817 | 3/1995 |
| WO | WO 95/09576 | 4/1995 |
| WO | WO 95/09577 | 4/1995 |
| WO | WO 95/14436 | 6/1995 |
| WO | WO 95/17855 | 7/1995 |
| WO | WO 95/18383 | 7/1995 |
| WO | WO 95/18572 | 7/1995 |
| WO | WO 95/19739 | 7/1995 |
| WO | WO 95/20360 | 8/1995 |
| WO | WO 95/23557 | 9/1995 |
| WO | WO 95/24865 | 9/1995 |
| WO | WO 95/25471 | 9/1995 |
| WO | WO 95/26562 | 10/1995 |
| WO | WO 95/29639 | 11/1995 |
| WO | WO 96/04858 | 2/1996 |
| WO | WO 96/19151 | 6/1996 |
| WO | WO 96/19152 | 6/1996 |
| WO | WO 96/20652 | 7/1996 |
| WO | WO 96/21119 | 7/1996 |
| WO | WO 96/22055 | 7/1996 |
| WO | WO 96/23448 | 8/1996 |
| WO | WO 96/24301 | 8/1996 |
| WO | WO 96/27337 | 9/1996 |
| WO | WO 96/31155 | 10/1996 |
| WO | WO 96/35464 | 11/1996 |
| WO | WO 96/39085 | 12/1996 |
| WO | WO 96/39086 | 12/1996 |
| WO | WO 96/39087 | 12/1996 |
| WO | WO 96/39088 | 12/1996 |
| WO | WO 96/39089 | 12/1996 |
| WO | WO 97/00646 | 1/1997 |
| WO | WO 97/00647 | 1/1997 |
| WO | WO 97/06582 | 2/1997 |
| WO | WO 97/10763 | 3/1997 |
| WO | WO 97/10764 | 3/1997 |
| WO | WO 97/11648 | 4/1997 |
| WO | WO 97/11649 | 4/1997 |
| WO | WO 97/15237 | 5/1997 |
| WO | WO 97/24073 | 7/1997 |
| WO | WO 97/24993 | 7/1997 |
| WO | WO 97/30644 | 8/1997 |

(56) References Cited

FOREIGN PATENT DOCUMENTS

| | | |
|---|---|---|
| WO | WO 97/34533 | 9/1997 |
| WO | WO 97/37598 | 10/1997 |
| WO | WO 97/39688 | 10/1997 |
| WO | WO 98/17180 | 4/1998 |
| WO | WO 98/27880 | 7/1998 |
| WO | WO 98/30153 | 7/1998 |
| WO | WO 98/47436 | 10/1998 |
| WO | WO 99/03407 | 1/1999 |
| WO | WO 99/03408 | 1/1999 |
| WO | WO 99/03409 | 1/1999 |
| WO | WO 99/12483 | 3/1999 |
| WO | WO 99/12487 | 3/1999 |
| WO | WO 99/12488 | 3/1999 |
| WO | WO 99/15086 | 4/1999 |
| WO | WO 99/15091 | 4/1999 |
| WO | WO 99/23933 | 5/1999 |
| WO | WO 99/23959 | 5/1999 |
| WO | WO 99/25261 | 5/1999 |
| WO | WO 99/29244 | 6/1999 |
| WO | WO 99/34744 | 7/1999 |
| WO | WO 99/45849 | 9/1999 |
| WO | WO 99/48430 | 9/1999 |
| WO | WO 99/51158 | 10/1999 |
| WO | WO 00/24322 | 5/2000 |
| WO | WO 00/24330 | 5/2000 |
| WO | WO 00/41638 | 7/2000 |
| WO | WO 00/48506 | 8/2000 |
| WO | WO 00/53112 | 9/2000 |
| WO | WO 00/54653 | 9/2000 |
| WO | WO 00/57796 | 10/2000 |
| WO | WO 00/64365 | 11/2000 |
| WO | WO 00/72762 | 12/2000 |
| WO | WO 00/72765 | 12/2000 |
| WO | WO 01/03587 | 1/2001 |
| WO | WO 01/05702 | 1/2001 |
| WO | WO 01/10482 | 2/2001 |
| WO | WO 01/35845 | 5/2001 |
| WO | WO 01/54594 | 8/2001 |
| WO | WO 01/58371 | 8/2001 |
| WO | WO 01/62158 | 8/2001 |
| WO | WO 01/62161 | 8/2001 |
| WO | WO 01/62162 | 8/2001 |
| WO | WO 01/62164 | 8/2001 |
| WO | WO 01/62169 | 8/2001 |
| WO | WO 01/78605 | 10/2001 |
| WO | WO 01/91646 | 12/2001 |
| WO | WO 02/07608 | 1/2002 |
| WO | WO 02/07618 | 1/2002 |
| WO | WO 02/17799 | 3/2002 |
| WO | WO 02/19920 | 3/2002 |
| WO | WO 02/19932 | 3/2002 |
| WO | WO 02/30297 | 4/2002 |
| WO | WO 02/32322 | 4/2002 |
| WO | WO 02/36028 | 5/2002 |
| WO | WO 02/43571 | 6/2002 |
| WO | WO 02/058568 | 8/2002 |
| WO | WO 02/060328 | 8/2002 |
| WO | WO 02/067785 | 9/2002 |
| WO | WO 02/098302 | 12/2002 |
| WO | WO 03/000138 | 1/2003 |
| WO | WO 03/001329 | 1/2003 |
| WO | WO 03/013363 | 2/2003 |
| WO | WO 03/015604 | 2/2003 |
| WO | WO 03/020106 | 3/2003 |
| WO | WO 03/020139 | 3/2003 |
| WO | WO 03/024339 | 3/2003 |
| WO | WO 03/079909 | 3/2003 |
| WO | WO 03/030743 | 4/2003 |
| WO | WO 03/037193 | 5/2003 |
| WO | WO 03/047436 | 6/2003 |
| WO | WO 03/055402 | 7/2003 |
| WO | WO 03/057048 | 7/2003 |
| WO | WO 03/057058 | 7/2003 |
| WO | WO 03/063694 | 8/2003 |
| WO | WO 03/077769 | 9/2003 |
| WO | WO 03/079911 | 10/2003 |
| WO | WO 03/082126 | 10/2003 |
| WO | WO 03/088845 | 10/2003 |
| WO | WO 03/090630 | 11/2003 |
| WO | WO 03/094743 | 11/2003 |
| WO | WO 03/094745 | 11/2003 |
| WO | WO 03/094746 | 11/2003 |
| WO | WO 03/094747 | 11/2003 |
| WO | WO 03/101313 | 12/2003 |
| WO | WO 03/105698 | 12/2003 |
| WO | WO 03/105702 | 12/2003 |
| WO | WO 2004/006980 | 1/2004 |
| WO | WO 2004/011037 | 2/2004 |
| WO | WO 2004/019769 | 3/2004 |
| WO | WO 2004/021868 | 3/2004 |
| WO | WO 2004/028585 | 4/2004 |
| WO | WO 2004/032754 | 4/2004 |
| WO | WO 2004/032760 | 4/2004 |
| WO | WO 2004/032762 | 4/2004 |
| WO | WO 2004/032763 | 4/2004 |
| WO | WO 2004/034875 | 4/2004 |
| WO | WO 2004/047626 | 6/2004 |
| WO | WO 2004/047653 | 6/2004 |
| WO | WO 2004/049956 | 6/2004 |
| WO | WO 2004/052426 | 6/2004 |
| WO | WO 2004/056276 | 7/2004 |
| WO | WO 2004/056277 | 7/2004 |
| WO | WO 2004/062516 | 7/2004 |
| WO | WO 2004/078050 | 9/2004 |
| WO | WO 2004/078051 | 9/2004 |
| WO | WO 2004/086987 | 10/2004 |
| WO | WO 2004/096015 | 11/2004 |
| WO | WO 2004/096057 | 11/2004 |
| WO | WO 2004/103157 | 12/2004 |
| WO | WO 2004/105593 | 12/2004 |
| WO | WO 2004/105621 | 12/2004 |
| WO | WO 2004/112618 | 12/2004 |
| WO | WO 2004/112652 | 12/2004 |
| WO | WO 2005/027983 | 3/2005 |
| WO | WO 2005/037329 | 4/2005 |
| WO | WO 2005/044078 | 5/2005 |
| WO | WO 2005/055846 | 6/2005 |
| WO | WO 2005/072634 | 8/2005 |
| WO | WO 2005/078892 | 8/2005 |
| WO | WO 2005/079675 | 9/2005 |
| WO | WO 2005/096954 | 10/2005 |
| WO | WO 2005/112806 | 12/2005 |
| WO | WO 2005/112808 | 12/2005 |
| WO | WO 2005/115251 | 12/2005 |
| WO | WO 2005/115253 | 12/2005 |
| WO | WO 2005/117735 | 12/2005 |
| WO | WO 2005/122936 | 12/2005 |
| WO | WO 2006/027014 | 3/2006 |
| WO | WO 2006/044490 | 4/2006 |
| WO | WO 2006/044581 | 4/2006 |
| WO | WO 2006/044810 | 4/2006 |
| WO | WO 2006/051252 | 5/2006 |
| WO | WO 2006/059067 | 6/2006 |
| WO | WO 2006/083748 | 8/2006 |
| WO | WO 2006/092563 | 9/2006 |
| WO | WO 2006/092565 | 9/2006 |
| WO | WO 2006/115958 | 11/2006 |
| WO | WO 2006/125940 | 11/2006 |
| WO | WO 2006/132992 | 12/2006 |
| WO | WO 2007/002180 | 1/2007 |
| WO | WO 2007/016290 | 2/2007 |
| WO | WO 2007/018898 | 2/2007 |
| WO | WO 2007/098220 | 8/2007 |
| WO | WO 2007/121579 | 11/2007 |
| WO | WO 2007/131110 | 11/2007 |
| WO | WO 2007/137304 | 11/2007 |
| WO | WO 2007/139734 | 12/2007 |
| WO | WO 2007/142625 | 12/2007 |
| WO | WO 2007/147439 | 12/2007 |
| WO | WO 2008/021969 | 2/2008 |
| WO | WO 2008/039249 | 4/2008 |
| WO | WO 2008/039270 | 4/2008 |
| WO | WO 2008/045383 | 4/2008 |
| WO | WO 2008/070763 | 6/2008 |

(56) References Cited

FOREIGN PATENT DOCUMENTS

| WO | WO 2008/089404 | | 7/2008 |
|----|----------------|----|--------|
| WO | WO 2008/109125 | | 9/2008 |
| WO | WO 2010/063795 | | 6/2010 |
| WO | WO 2010/098871 | | 9/2010 |
| WO | WO 2012/021671 | | 2/2012 |
| WO | WO 2012/044844 | | 4/2012 |
| WO | WO 2012/171423 | A1 | 12/2012 |

OTHER PUBLICATIONS

U.S. Appl. No. 13/780,082, filed Feb. 28, 2013.
U.S. Appl. No. 13/780,106, filed Feb. 28, 2013.
U.S. Appl. No. 13/780,120, filed Feb. 28, 2013.
U.S. Appl. No. 13/780,402, filed Feb. 28, 2013.
U.S. Appl. No. 13/780,417, filed Feb. 28, 2013.
Disclosed Anonymously, "Motor-Driven Surgical Stapler Improvements," Research Disclosure Database No. 526041, Published: Feb. 2008.
Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet- =1&journalCode=vsu which redirects to http://www3.interscience.wiley.com/journal/119040681/abstract?CRETRY=1 &SR- ETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Steerable Endoscope," IEEE Engineering in Medicine and Biology Magazine (Nov./Dec. 2005).
Tuite, "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Chinese Office Action dated Jul. 12, 2010 for Application No. CN 200780041953.0.
Chinese Office Action dated Jun. 9, 2011 for Application No. CN 200780041953.0.
European Search Report for 11191409.9, dated Aug. 1, 2012 (8 pages).
International Search Report, Application No. PCT/US2007/017587, dated Dec. 12, 2007 (7 pages).
Restriction Requirement dated Apr. 10, 2009 for U.S. Appl. No. 11/541,123.
Office Action Non-Final dated Aug. 14, 2009 for U.S. Appl. No. 11/541,123.
Notice of Allowance dated Apr. 26, 2010 for U.S. Appl. No. 11/541,123.
Restriction Requirement dated Apr. 24, 2012 for U.S. Appl. No. 12/880,414.
Office Action Non-Final dated Oct. 18, 2012 for U.S. Appl. No. 12/880,414.
Office Action Final dated May 24, 2013 for U.S. Appl. No. 12/880,414.
U.S. Appl. No. 12/031,573, filed Feb. 14, 2008.
Japanese Office Action, Notification of Reasons for Refusal, dated Jan. 9, 2018 for Application No. JP 2015-560217, 5 pgs.
European Search Report, Extended, and Written Opinion dated Jul. 7, 2017 for Application No. EP 17162158.4, 8 pgs.
Chinese Office Action, Notification of First Office Action, dated Mar. 22, 2017 for Application No. CN 201480010837.2, 12 pgs.
European Search Report, Partial, and Written Opinion dated Oct. 16, 2014 for Application No. EP 14157364.2, 10 pgs.
International Search Report and Written Opinion dated Jun. 4, 2014 for Application No. PCT/US2014/017304, 12 pgs.

\* cited by examiner

STAPLE FORMING FEATURES FOR SURGICAL STAPLING INSTRUMENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued Apr. 2, 2013 as U.S. Pat. No. 8,408,439; and U.S. Pub. No. 2012/0239012, entitled "Motor-Driven Surgical Cutting Instrument with Electric Actuator Directional Control Assembly," published Sep. 20, 2012, issued Jun. 4, 2013 as U.S. Pat. No. 8,453,914. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
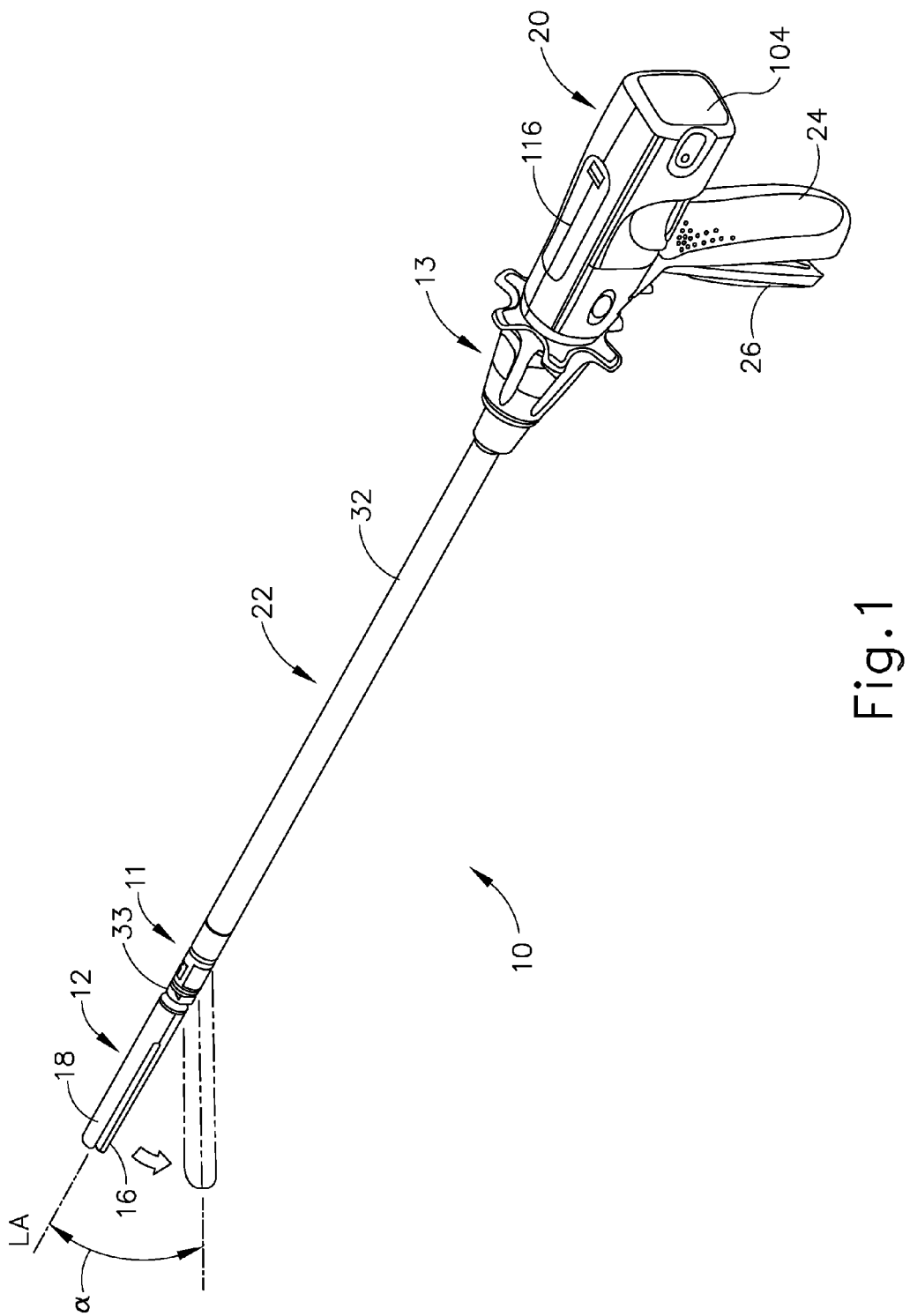
FIG. 1 depicts a perspective view of an exemplary articulating surgical stapling instrument.
Figure 2:
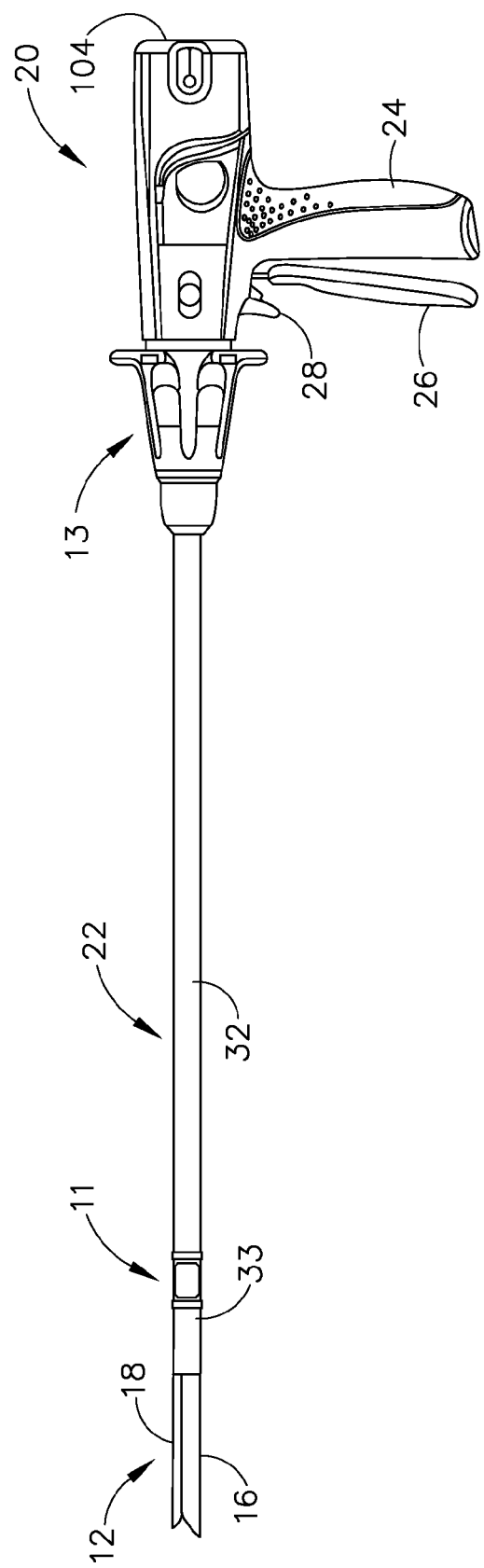
FIG. 2 depicts a side elevational view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. patent application Ser. No. 13/780,402, entitled "Surgical Instrument with Multi-Diameter Shaft," filed on even date herewith, now U.S. Pat. No. 9,795,379, issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (α). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. patent application Ser. No. 13/780,067, entitled "Surgical Instrument End Effector Articulation Drive with Pinion and Opposing Racks," filed on even date herewith, now U.S. Pat. No. 9,186,142, issued Nov. 17, 2015, the disclosure of which is incorporated by reference herein. Articulation joint (11) may also be constructed and operable in accordance with at least some of the teachings of U.S. patent application Ser. No. 13/780,402, now U.S. Pat. No. 9,795,379, issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. patent application Ser. No. 13/780,417, entitled "Installation Features for Surgical Instrument End Effector Cartridge," filed on even date herewith, now U.S. Pat. No. 9,808,248, issued Nov. 7, 2017, the disclosure of which is incorporated by reference herein. Anvil (18) may be constructed in accordance with at least some of the teachings of U.S. patent application Ser. No. 13/780,106, now U.S. Pat. No. 9,517,065, issued Dec. 13, 2016, entitled "Integrated Tissue Positioning and Jaw Alignment Features for Surgical Stapler," filed on even date herewith, the disclosure of which is incorporated by reference herein; at least some of the teachings of U.S. patent application Ser. No. 13/780,120, entitled "Jaw Closure Feature for End Effector of Surgical Instrument," filed on even date herewith, now U.S. Pat. No. 9,839,421, issued Dec. 12, 2017, the disclosure of which is incorporated by reference herein; and/or at least some of the teachings below. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (136) (shown in FIG. 11) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. patent application Ser. No. 13/780,082, entitled "Lockout Feature for Movable Cutting Member of Surgical Instrument," filed on even date herewith, now U.S. Pat. No. 9,717,497, issued Aug. 1, 2017, the disclosure of which is incorporated by reference herein. Other suitable forms that firing beam (14) may take will be apparent to those of ordinary skill in the art in view of the teachings herein.

Figure 3:
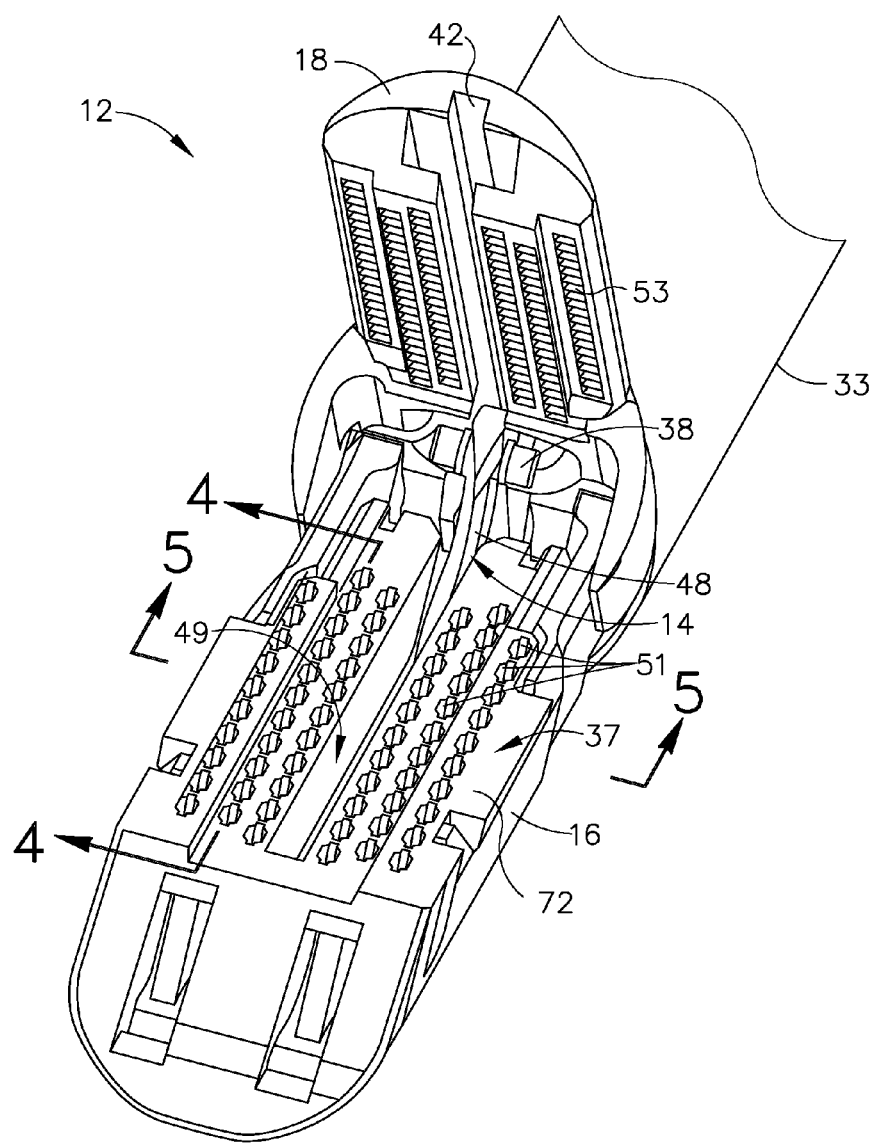
FIG. 3 depicts a perspective view of an opened end effector of the instrument of FIG. 1.
Figure 4A:
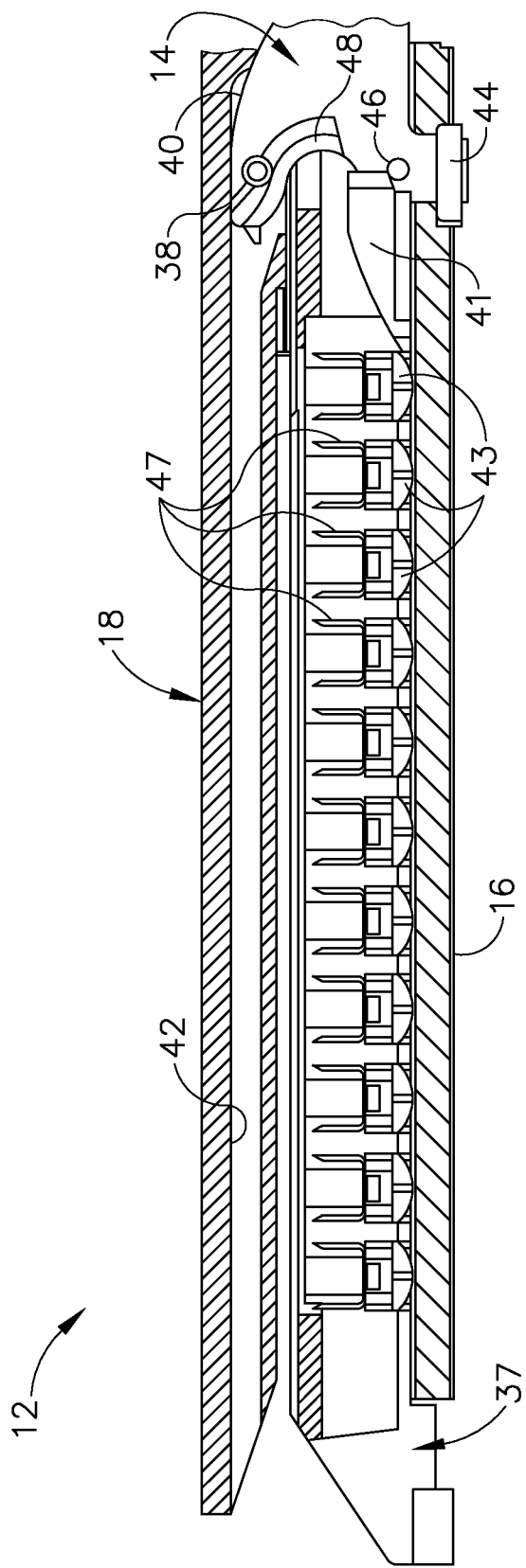
FIG. 4A depicts a side cross-sectional view of the end effector of FIG. 3, taken along line 4-4 of FIG. 3, with the firing beam in a proximal position.
Figure 4B:
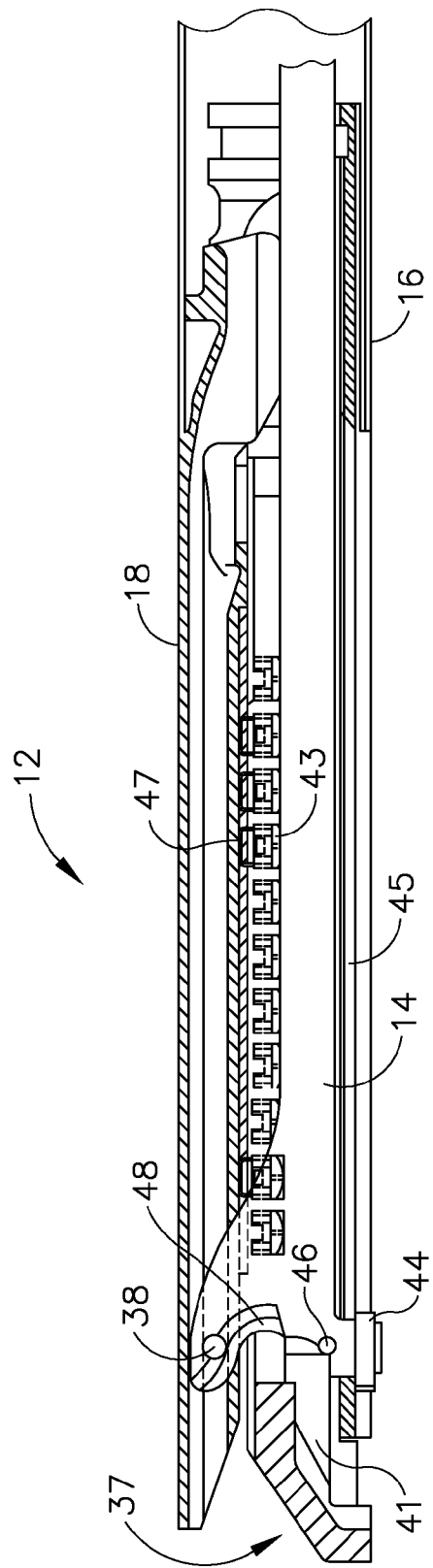
FIG. 4B depicts a side cross-sectional view of the end effector of FIG. 3, taken along line 4-4 of FIG. 3, with the firing beam in a distal position.
Figure 5:
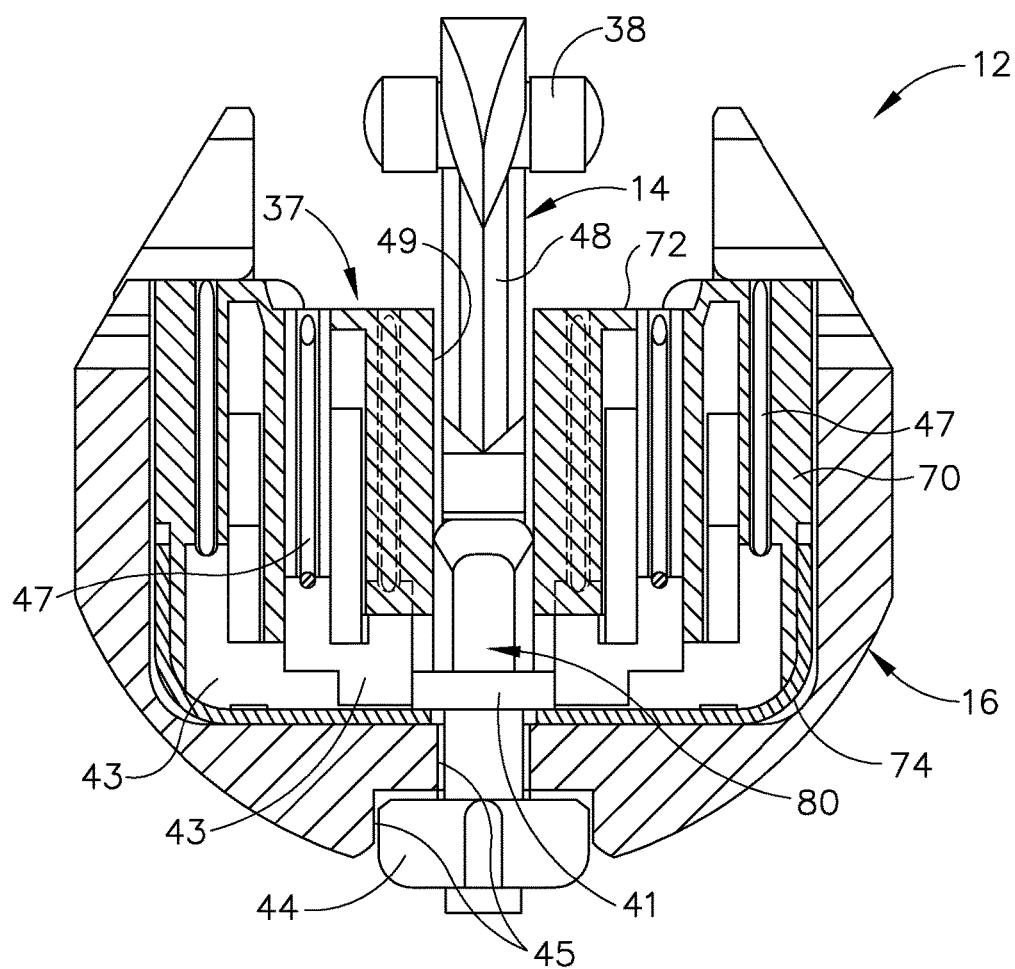
FIG. 5 depicts an end cross-sectional view of the end effector of FIG. 3, taken along line 5-5 of FIG. 3.
Figure 6:
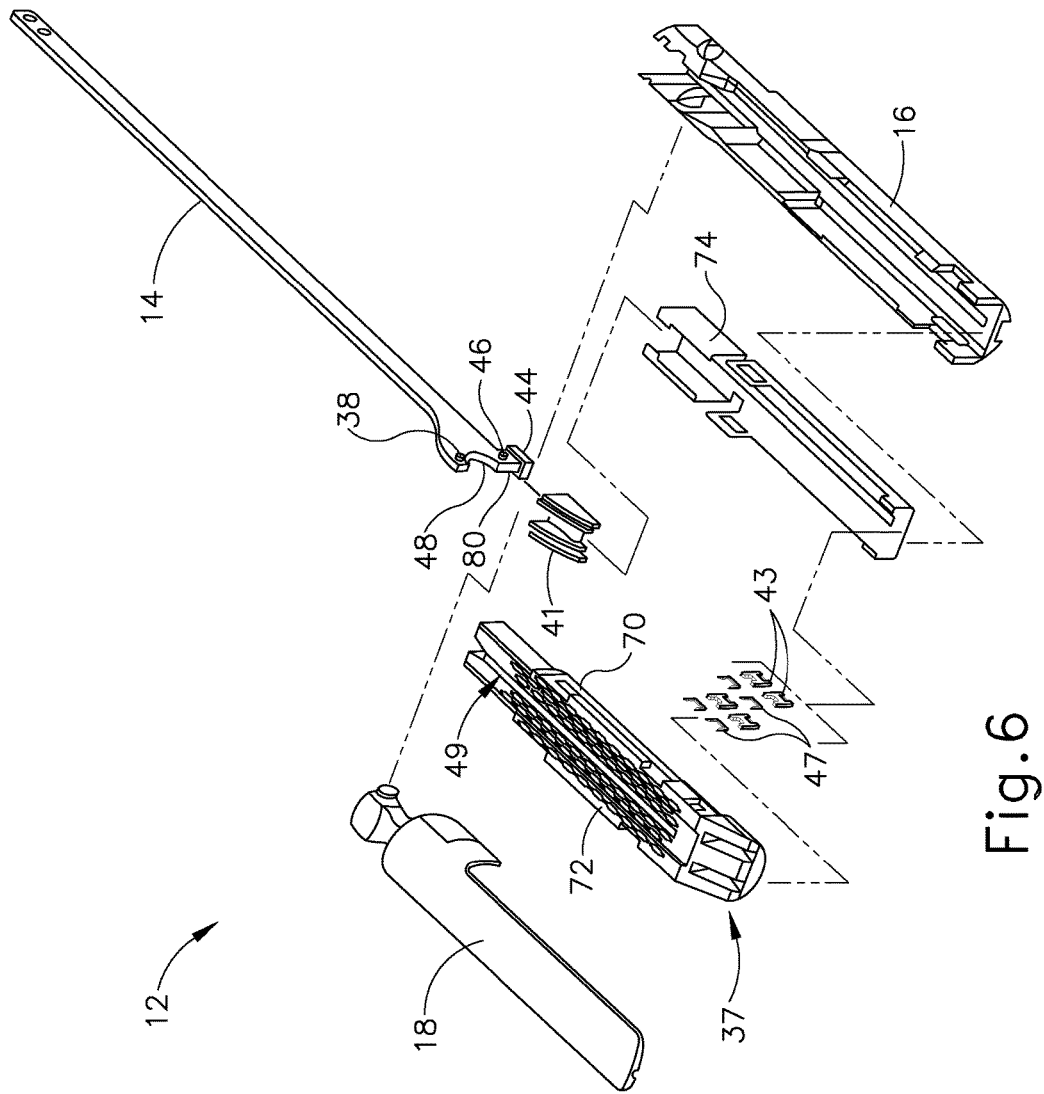
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. patent application Ser. No. 13/780,106, now U.S. Pat. No. 9,517,065, issued Dec. 13, 2016, the disclosure of which is incorporated by reference herein. In addition or in the alternative, staple cartridge (37) may be constructed and operable in accordance with at least some of the teachings of U.S. patent application Ser. No. 13/780,417, now U.S. Pat. No. 9,808,248, issued Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
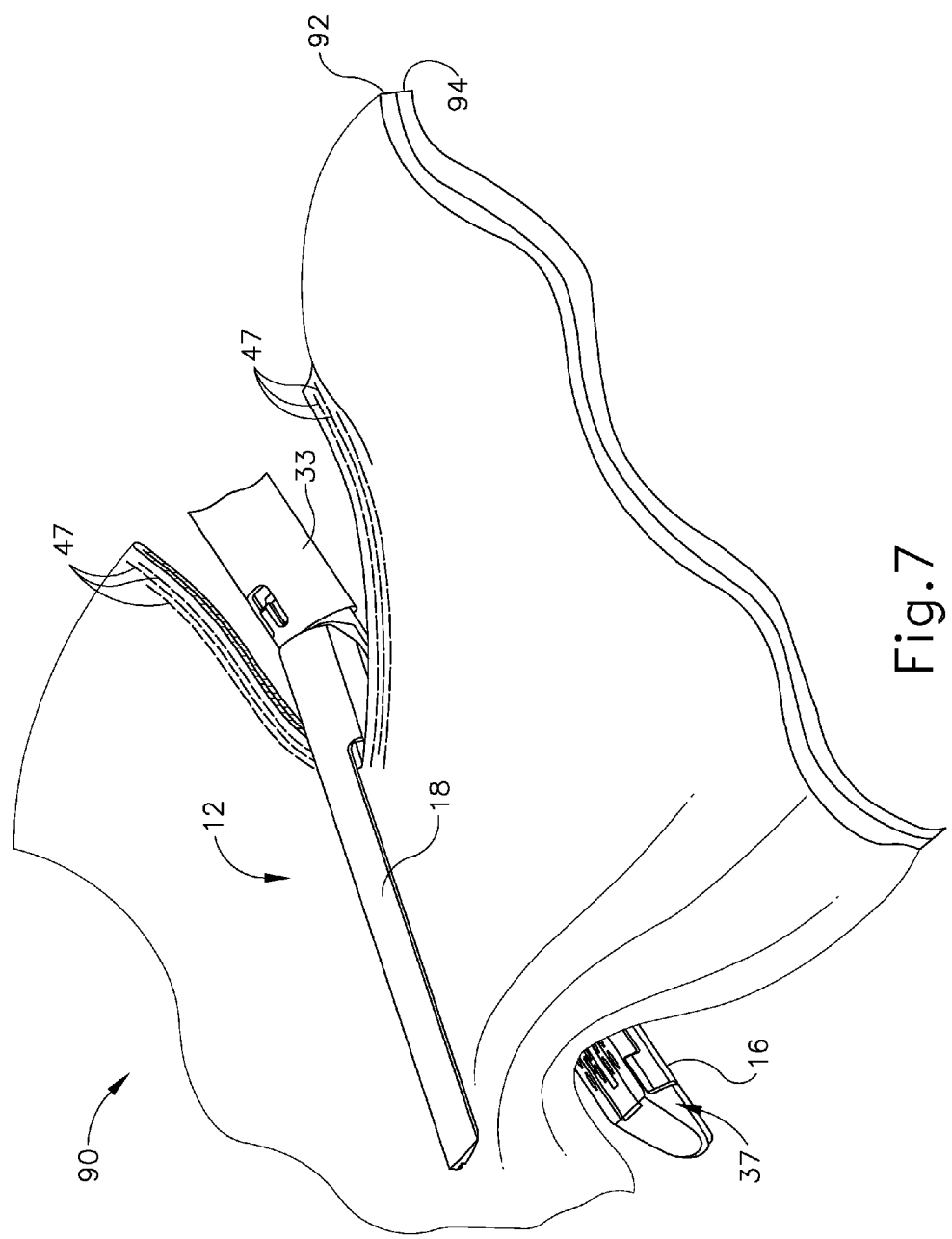
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat.

No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; U.S. Pat. No. 7,721,930; U.S. Pub. No. 2010/0264193, issued as U.S. Pat. No. 8,408,439; and/or 2012/0239012, issued as U.S. Pat. No. 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Motorized Drive Features

Figure 8:
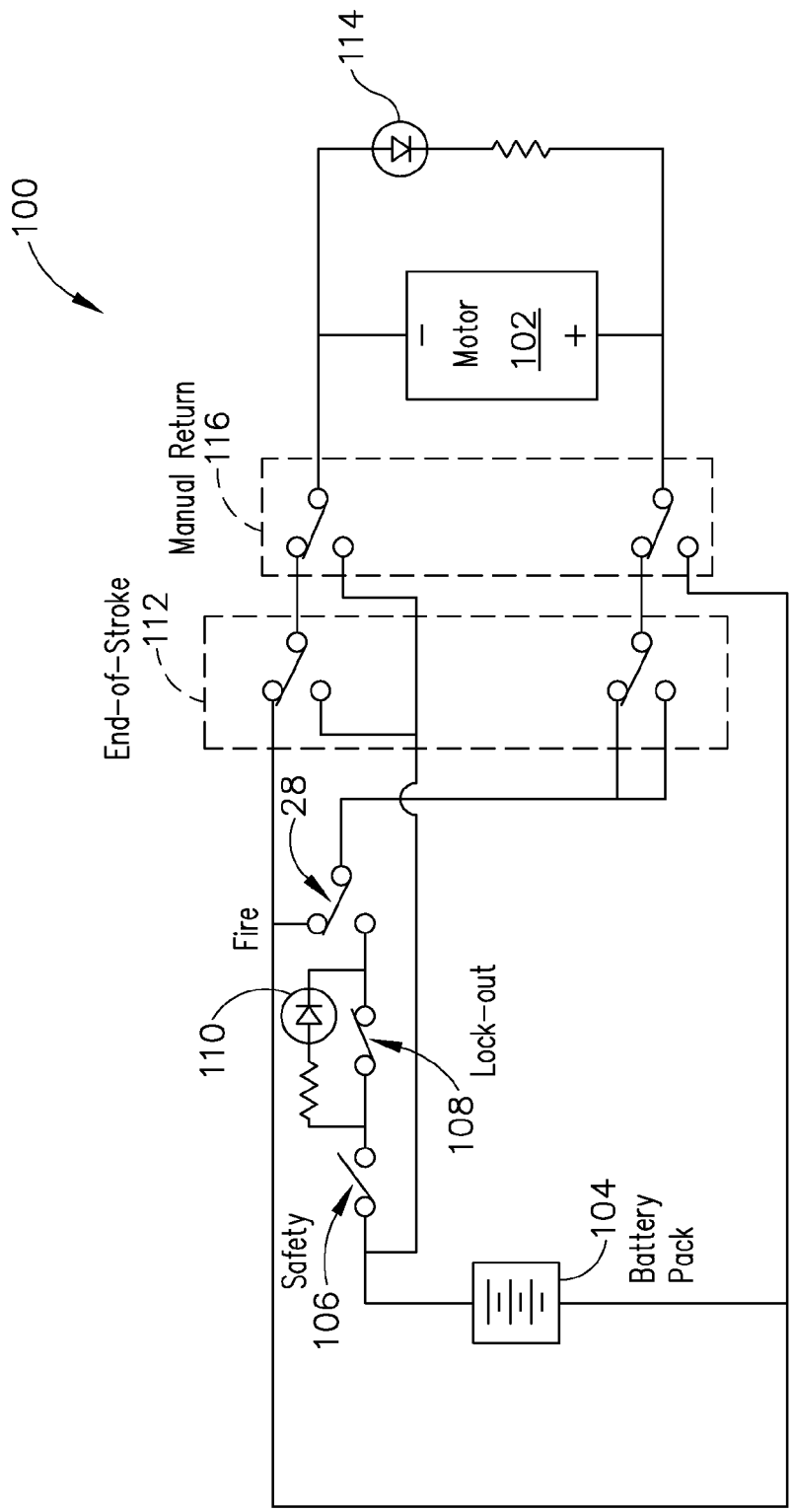
FIG. 8 depicts a schematic view of an exemplary control circuit for use in the instrument of FIG. 1.

In the present example, instrument (10) provides motorized control of firing beam (14). FIGS. 8-11 show exemplary components that may be used to provide motorized control of firing beam (14). In particular, FIG. 8 shows an exemplary control circuit (100) that may be used to power an electric motor (102) with electric power from a battery pack (104) (also shown in FIGS. 1-2). Electric motor (102) is operable to translate firing beam (14) longitudinally as will be described in greater detail below. It should be understood that the entire control circuit (100), including motor (102) and battery pack (104), may be housed within handle portion (20). FIG. 8 shows firing trigger (28) as an open switch, though it should be understood that this switch is closed when firing trigger (28) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle portion (20).

Circuit (100) of the present example also includes a lockout switch (108), which is configured to be closed by default but is automatically opened in response to a lockout condition. By way of example only, a lockout condition may include one or more of the following: the absence of a cartridge (37) in lower jaw (16), the presence of a spent (e.g., previously fired) cartridge (37) in lower jaw (16), an insufficiently closed anvil (18), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Once firing beam (14) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (28) at this stage of operation. In this operational state, current flows through a reverse direction indicator (114) (e.g., an LED, etc.) to provide a visual indication to the operator that motor (102) rotation has been reversed. Various suitable ways in which end-of-stroke switch (112) may be automatically switched to a closed position when firing beam (14) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle portion (20) of the present example also includes a manual return switch (116), which is also shown in circuit (100). Manual return switch (116) is configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114).

In some versions, one or more of switches (28, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 9:
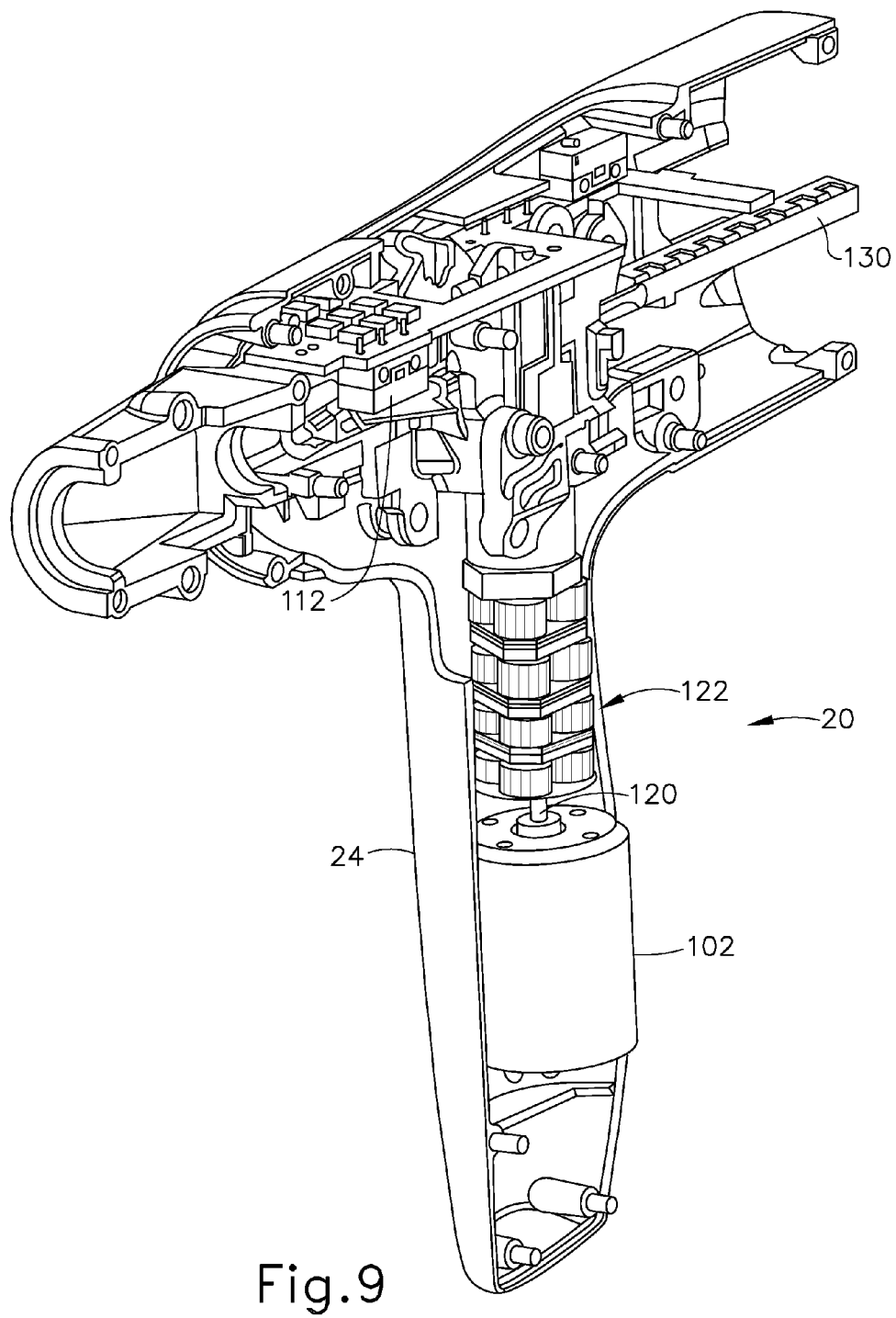
FIG. 9 depicts a perspective view of the handle assembly of the instrument of FIG. 1, with a housing half removed.
Figure 10:
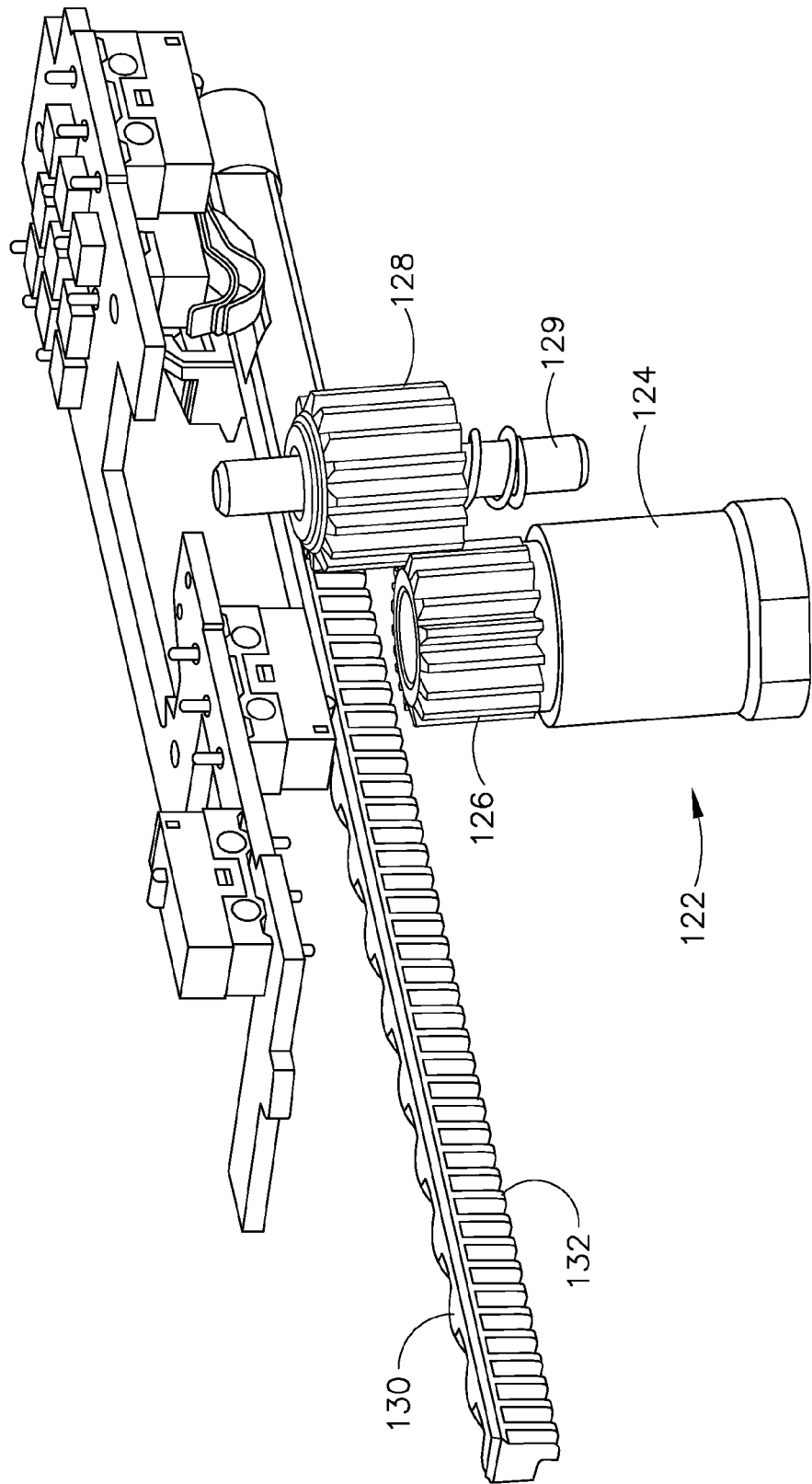
FIG. 10 depicts a perspective view of drive assembly components from the handle assembly of FIG. 9.
Figure 11:
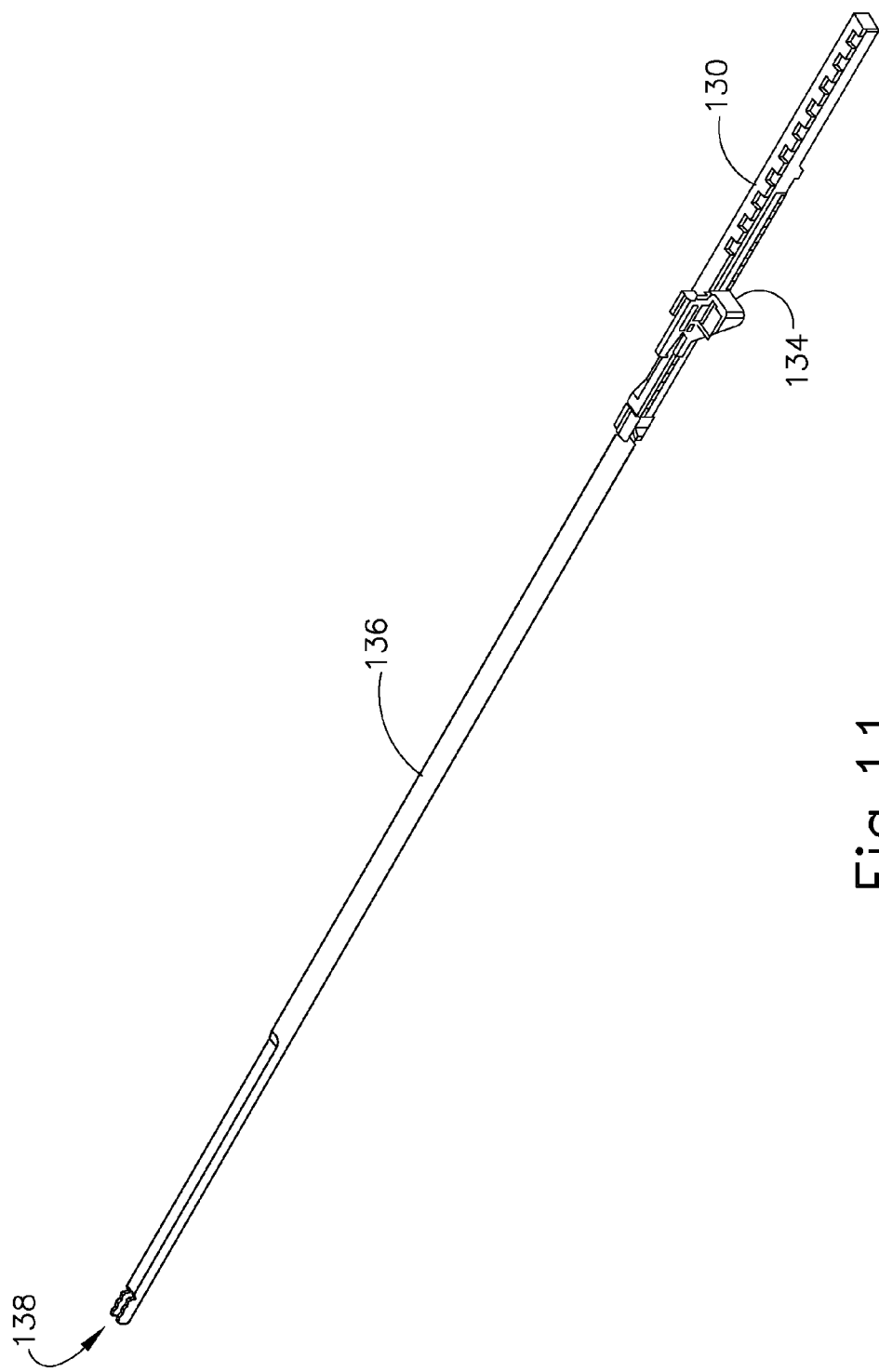
FIG. 11 depicts a perspective view of an elongate member from the drive assembly of FIG. 10.

FIGS. 9-11 show various mechanical components that may be used to provide motorized translation of firing beam (14). In particular, FIG. 9 shows motor (102) housed in pistol grip (24) of handle portion (20). It should be understood that battery pack (104) (shown in FIGS. 1-2) may also be located in pistol grip (24) (e.g., below motor (102)) and/or elsewhere within handle portion (20). Motor (102) has a drive shaft (120) that is coupled with a gear assembly (122). Gear assembly (122) has an external casing (not shown) and is operable to drive an upper gear (126), which is shown in FIG. 10. Upper gear (126) meshes with a pinion (128), which is rotatably supported by a pin (129) secured in handle portion (20). It should therefore be understood that activation of motor (102) will ultimately rotate pinion (128) within handle portion (20).

As also shown in FIGS. 9-10, a translating rack (130) includes teeth (132) that mesh with pinion (128), such that rack (130) translates longitudinally when pinion (128) rotates. As shown in FIG. 11, rack (130) is coupled with an elongate member (136), which extends through shaft (22) and includes a distal end (138) that couples with the proximal end of firing beam (14). Elongate member (136) translates within shaft (22), such that elongate member (136) communicates longitudinal motion of rack (130) to firing beam (14). It should therefore be understood that activation of motor (102) will ultimately translate firing beam (14)

within end effector (12). In particular, motor (102) may drive firing beam (14) distally to sever tissue (90) and drive staples (47) into tissue (90). A switch actuation arm (134) extends laterally from rack (130), and is positioned to engage end-of-stroke switch (112) when firing beam (14) reaches a distal-most position (e.g., after tissue (90) has been severed and staples (47) have been driven into tissue (90)). As noted above, this engagement of end-of-stroke switch (112) automatically reverses motor (102) to return firing beam (14) from the distal-most position to the proximal position, enabling anvil (18) to be pivoted away from lower jaw (16) to release tissue (90).

Use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

In addition to or in lieu of the foregoing, the features operable to drive firing beam (14) may be configured in accordance with at least some of the teachings of U.S. Pub. No. 2012/0239012, issued as U.S. Pat. No. 8,453,914, the disclosure of which is incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

III. Exemplary Anvil Configurations

As noted above, wedge sled (41) provides a camming action to drive staple drivers (43) upwardly within staple cartridge (37) when wedge sled (41) is driven distally. This upward movement of staple drivers (43) pushes staples (47) upwardly and out through staple apertures (51). This forces each staple (47) into an associated staple forming pocket (53) of anvil (18), ultimately resulting in bent/formed staples (47). The legs of the staples (47) penetrate layers (90, 92) of tissue as they are driven toward anvil (18), such that the formed staples (47) secure the layers (90, 92) of tissue (as shown in FIG. 7).

It should be understood that the configuration of staple forming pockets (53) may have a significant impact on the configuration of formed staples (47), such that varying the configuration of a staple forming pocket (53) may significantly vary the configuration of a staple (47) formed by staple forming pocket (53). Furthermore, it will be understood that varying the configuration of a staple (47) formed by staple forming pocket (53) may have a significant impact on how that formed staple (47) interacts with layers (90, 92) of tissue. For instance, some formed staple (47) configurations may provide greater hemostasis in layers (90, 92) of tissue than other formed staple (47) configurations. As another merely illustrative example, some formed staple (47) configurations may secure apposition of layers (90, 92) of tissue better than other formed staple (47) configurations. As yet another merely illustrative example, some formed staple (47) configurations may impose more trauma on layers (90, 92) of tissue (e.g., by tearing the tissue more) than other formed staple (47) configurations, which may affect the ability of the formed staples (47) to provide hemostasis and/or secure apposition of layers (90, 92), etc. Several exemplary configurations for staple forming pockets (53) will be described in greater detail below; while others will be apparent to those of ordinary skill in the art in view of the teachings herein.

A. Exemplary Staple Forming Pockets with Aligned Channels

Figure 12:
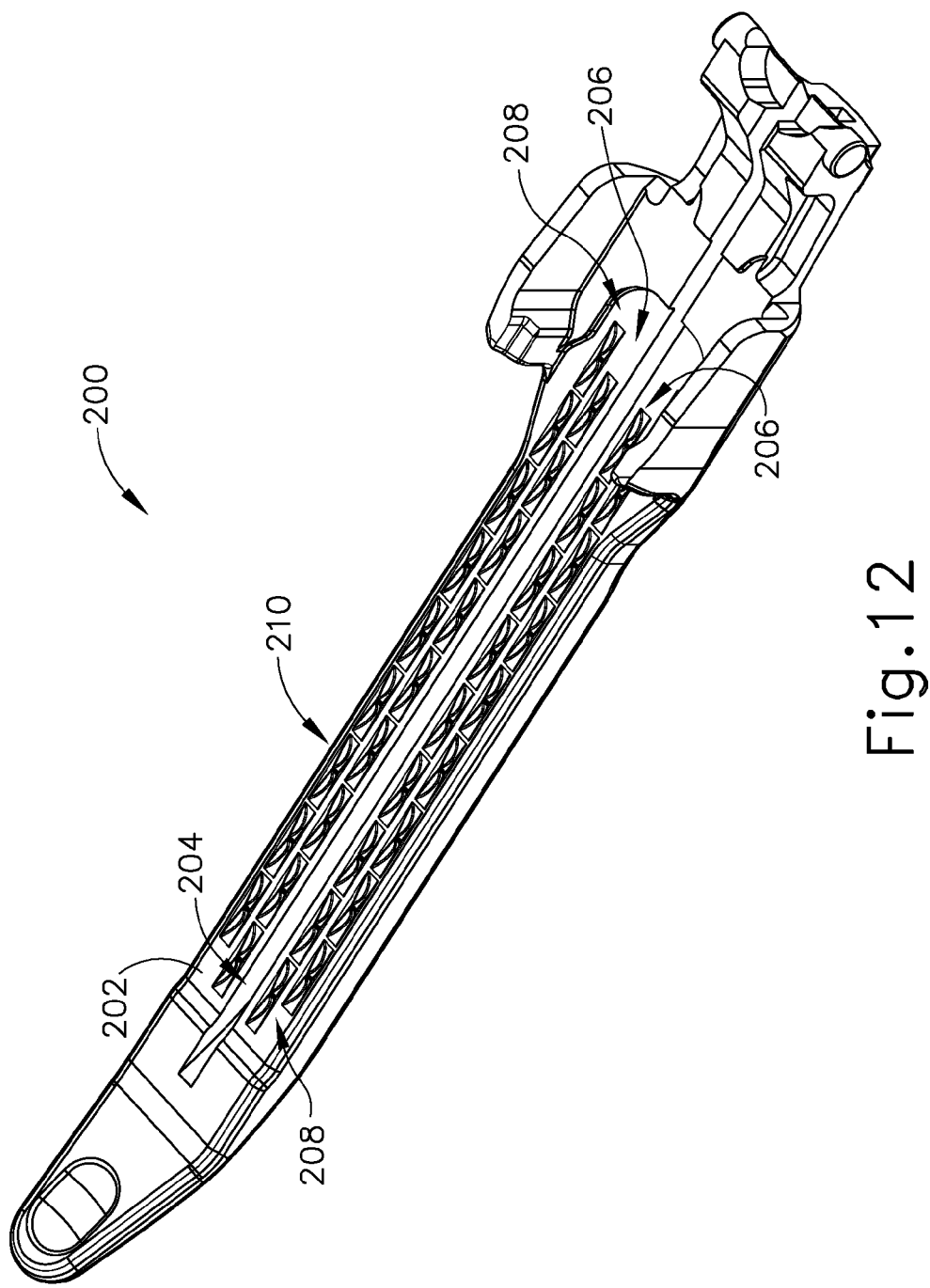
FIG. 12 depicts a perspective view of an exemplary alternative anvil that may be incorporated into the instrument of FIG. 1.
Figure 13:
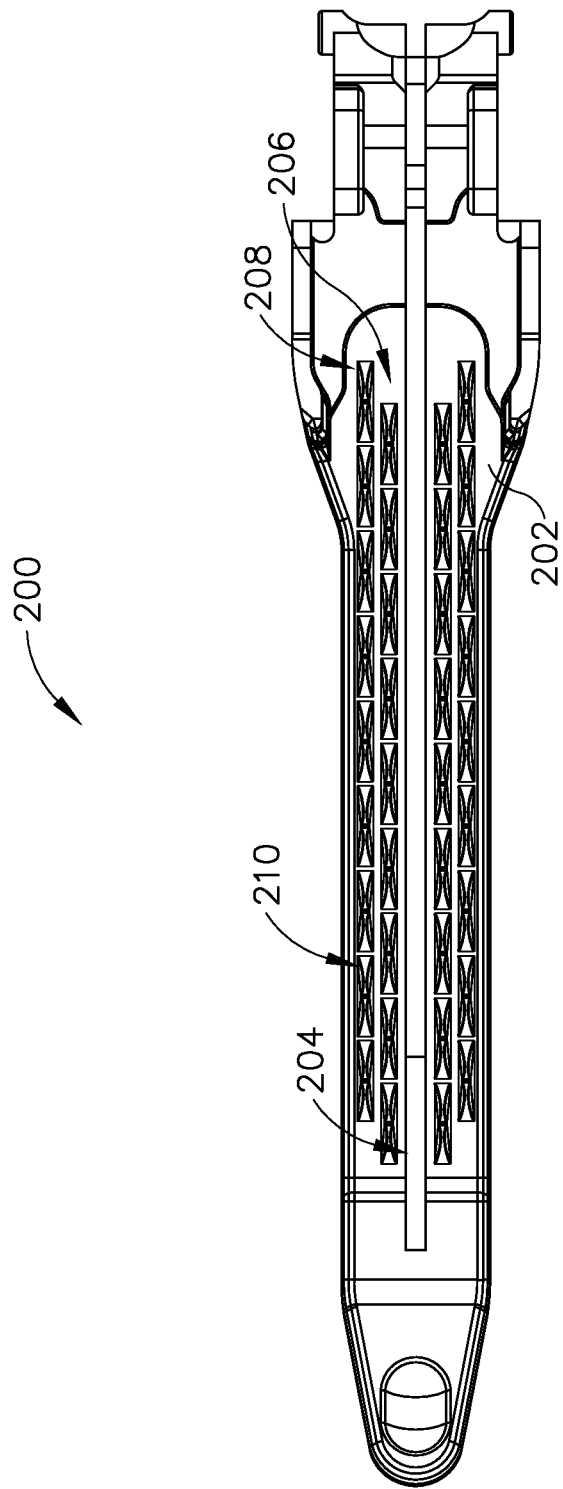
FIG. 13 depicts a bottom plan view of the anvil of FIG. 12.

FIGS. 12-13 show an exemplary anvil (200) that may be used in place of anvil (18) described above. Anvil (200) of this example defines a longitudinally extending slot (204), which is similar to anvil slot (42) described above. An upper portion of firing beam (14) translates through anvil slot (42) during a cutting/stapling stroke of instrument (10). Anvil (200) also includes a tissue contacting surface (202) that presses against tissue when the tissue is clamped between anvil (200) and upper deck (72) of staple cartridge (37). A series of staple forming pockets (210) are recessed relative to tissue contacting surface (202). In the present example, anvil (200) has two rows (206, 208) of staple forming pockets (210) on each side of slot (204). However, it should be understood that any other suitable number of rows of staple forming pockets (210) may be provided on each side of slot (204). By way of example only, some other versions may include three rows of staple forming pockets (210) on each side of slot (204). It should also be noted that, on each side of slot (204), inner row (206) is longitudinally offset relative to an outer row (208). The results of such an offset would be similar to what is shown in FIG. 7, where formed staples (47) are longitudinally offset among adjacent rows. Of course, staple forming pockets (210) may have any other suitable arrangements relationships with each other.

Figure 14:
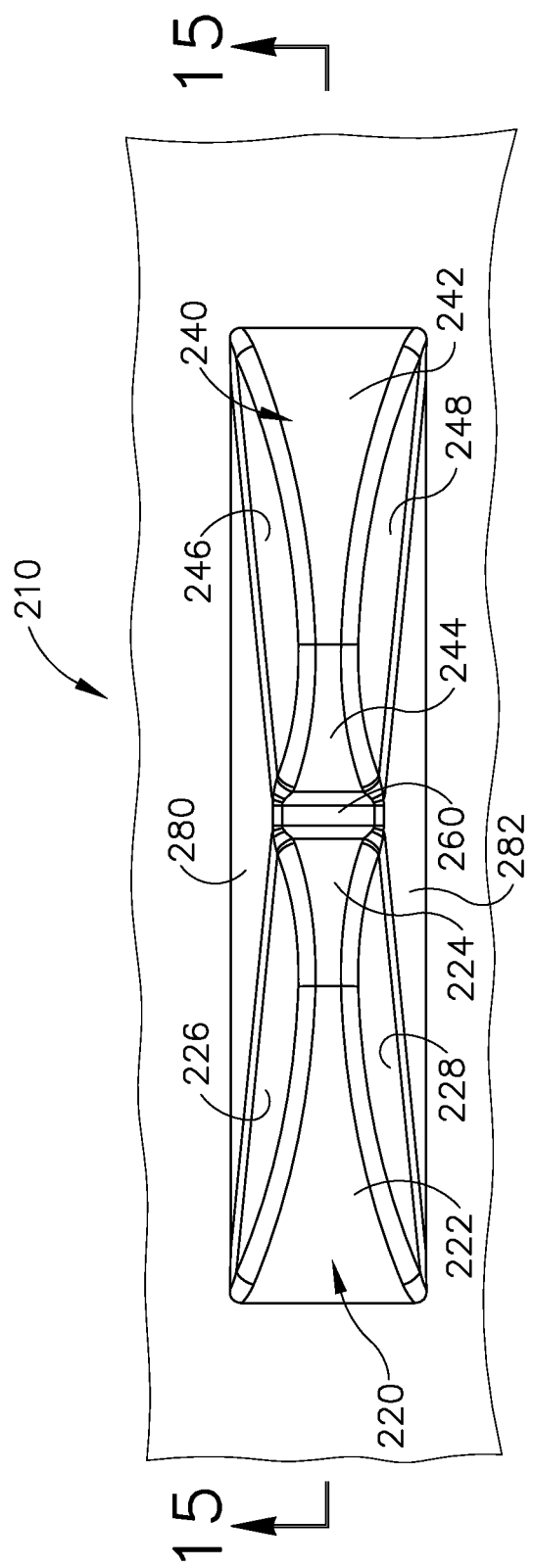
FIG. 14 depicts an enlarged plan view of a staple forming pocket of the anvil of FIG. 12.
Figure 15:
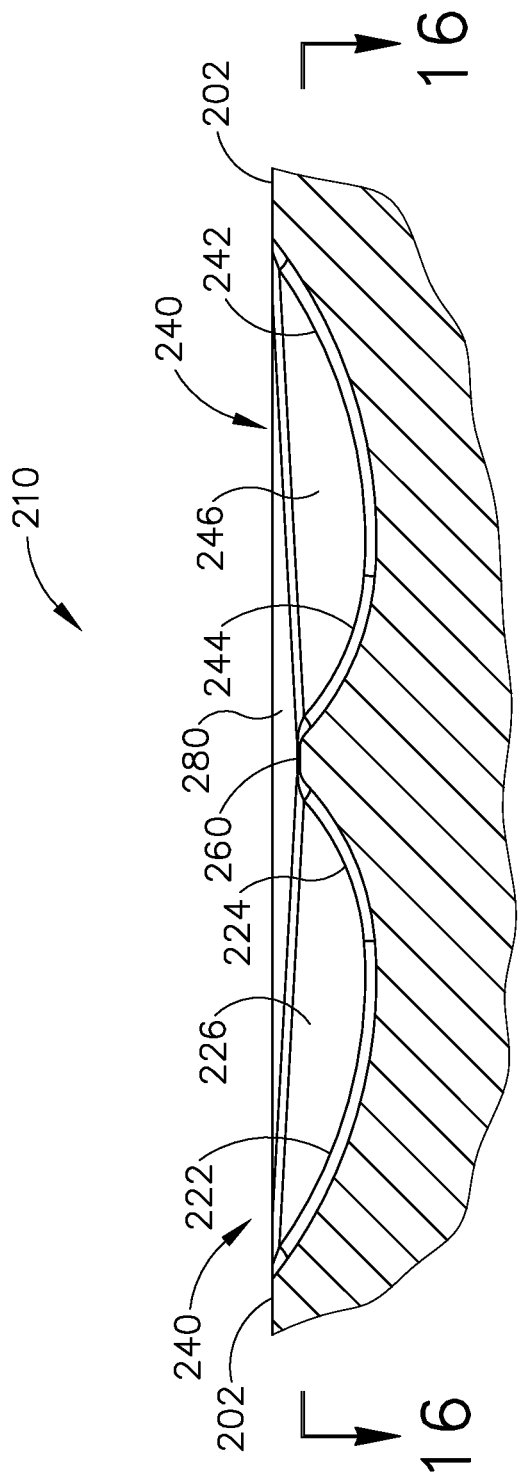
FIG. 15 depicts a cross-sectional view of the staple forming pocket of FIG. 14, taken along line 15-15 of FIG. 14.
Figure 16:
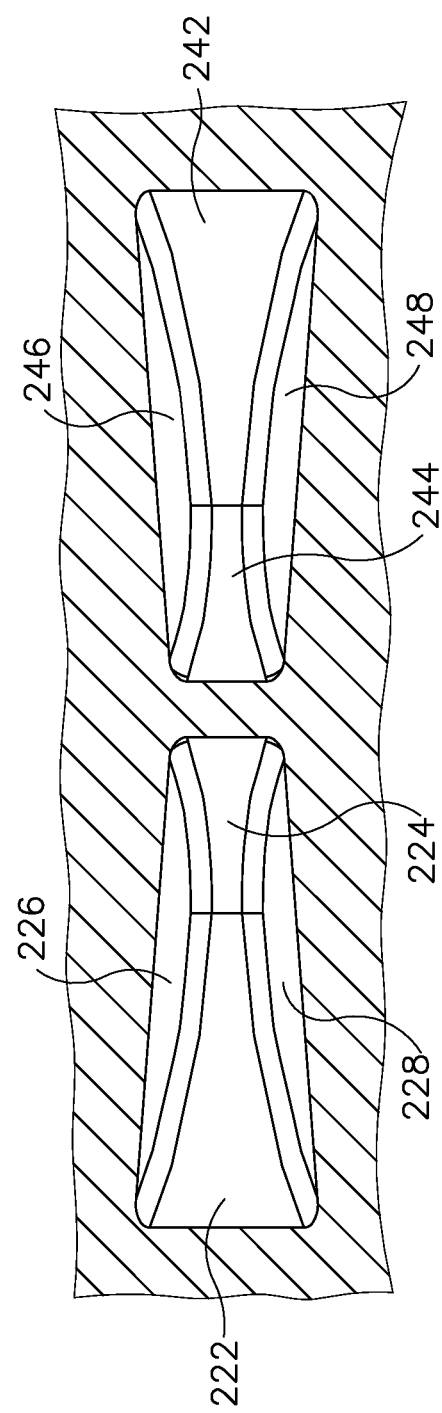
FIG. 16 depicts a cross-sectional view of the staple forming pocket of FIG. 14, taken along line 16-16 of FIG. 15.

FIGS. 14-16 show a single staple forming pocket (210) in greater detail. It should be understood that all staple forming pockets (210) of anvil (200) may be similarly configured. Staple forming pocket (210) of this example provides a first channel (220) and a second channel (240). Second channel (240) is aligned with first channel (220). A dividing wall surface (260) separates channels (220, 240). Channels (220, 240) are symmetric about a vertical plane that passes through wall along and that extends transversely relative to staple forming pocket (210).

Channel (220) is longitudinally defined by a downwardly sloping concave surface (222), which smoothly transitions into an upwardly sloping concave surface (224), which terminates at dividing wall surface (260). Channel (220) is laterally defined by a pair of sidewalls (226, 228), which are vertically angled such that the lower regions of sidewalls (226, 228) are closer to each other than the upper regions of sidewalls (226, 228). Sidewalls (226, 228) are also laterally angled such that the ends of sidewalls (226, 228) adjacent to dividing wall surface (260) are closer to each other than the ends of sidewalls (226, 228) further away from dividing wall surface (260).

Channel (240) is longitudinally defined by a downwardly sloping concave surface (242), which smoothly transitions into an upwardly sloping concave surface (244), which terminates at dividing wall surface (260). Channel (240) is laterally defined by a pair of sidewalls (246, 248), which are vertically angled such that the lower regions of sidewalls (246, 248) are closer to each other than the upper regions of sidewalls (246, 248). Sidewalls (246, 248) are also laterally angled such that the ends of sidewalls (246, 248) adjacent to dividing wall surface (260) are closer to each other than the ends of sidewalls (246, 248) further away from dividing wall surface (260).

Staple forming pocket (210) also includes lead-in surfaces (280, 282) that extend along the length of staple forming pocket (210). Lead-in surface (280) is adjacent to sidewalls (226, 246) and dividing wall surface (260). Lead-in surface (282) is adjacent to sidewalls (228, 248) and dividing wall surface (260). Lead-in surfaces (280, 282) are vertically angled to assist in guiding the tips of staple legs into channels (220, 240) as the staple is being driven toward staple forming pocket (210). However, the angle defined between each lead-in surface (280, 282) and the horizontal plane (along which tissue contacting surface (202) lies) is less than the angle defined between each sidewall (226, 246, 228, 248) and the same horizontal plane. It should be understood that lead-in surfaces (280, 282) may also alleviate very localized tissue compression at staple forming pocket (210) during the final stages of staple formation.

Figure 17:
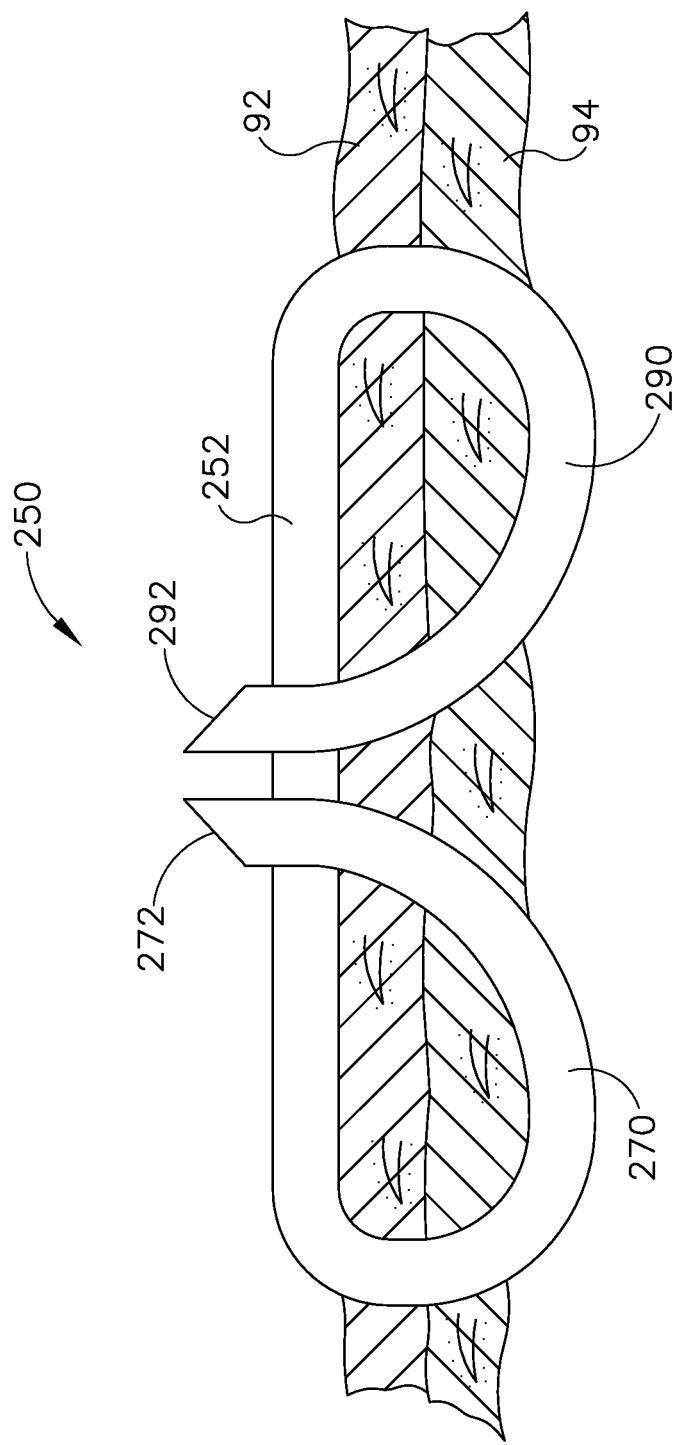
FIG. 17 depicts a side elevational view of an exemplary staple formed by the staple forming pocket of FIG. 14, disposed in tissue.
Figure 18A:
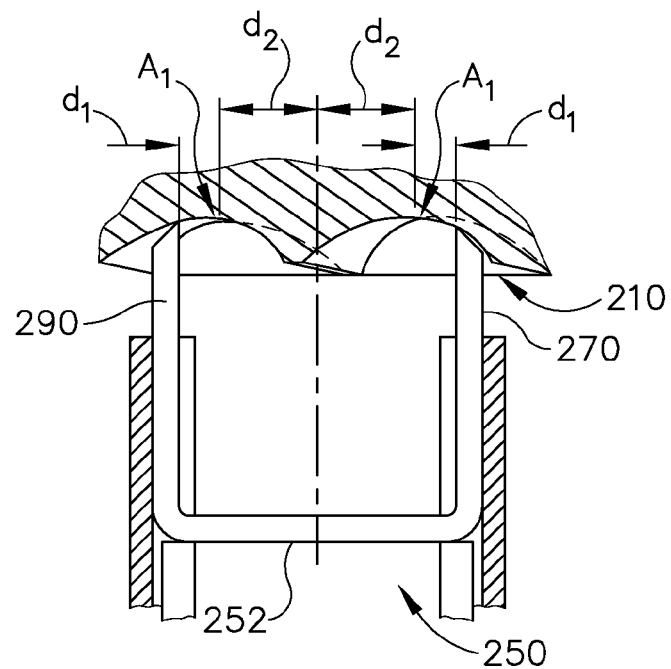
FIG. 18A depicts a side elevational view of the staple of FIG. 17 in an unformed state, initially contacting the staple forming pocket of FIG. 14 in a first stage of staple formation.
Figure 18B:
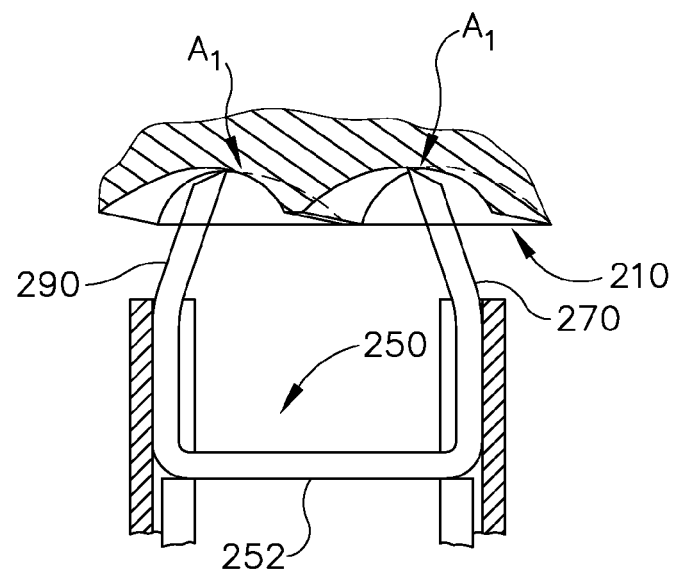
FIG. 18B depicts a side elevational view of the staple of FIG. 17 being driven into the staple forming pocket of FIG. 14 in a second stage of staple formation.
Figure 18C:
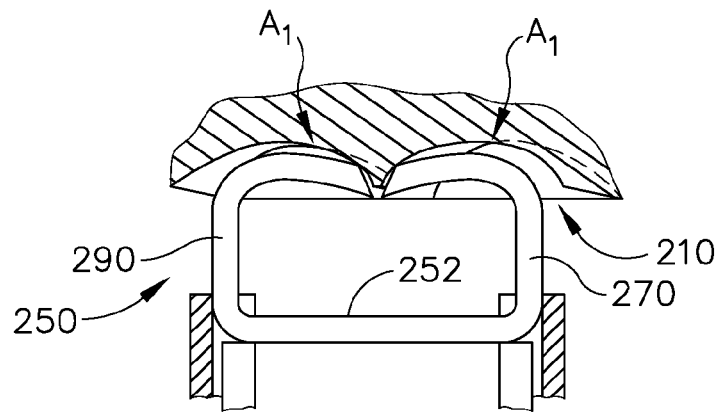
FIG. 18C depicts a side elevational view of the staple of FIG. 17 being driven further into the staple forming pocket of FIG. 14 in a third stage of staple formation.
Figure 18D:
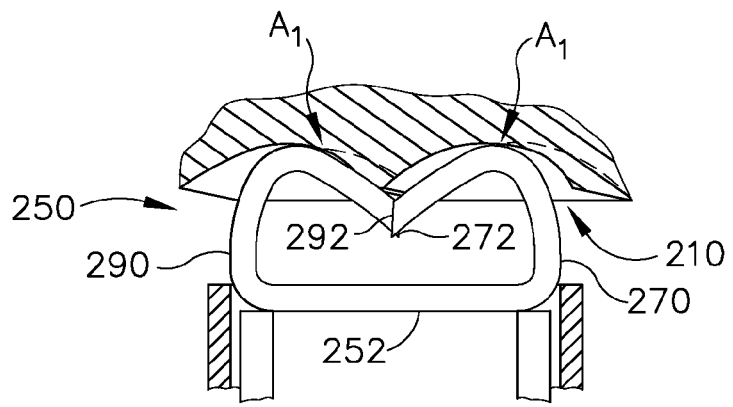
FIG. 18D depicts a side elevational view of the staple of FIG. 17 being driven further into the staple forming pocket of FIG. 14 in a fourth stage of staple formation.
Figure 18E:
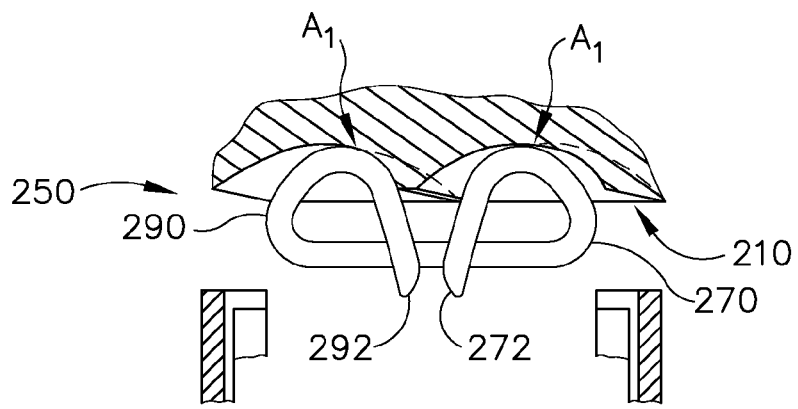
FIG. 18E depicts a side elevational view of the staple of FIG. 17 being fully driven into the staple forming pocket of FIG. 14 at a final stage of staple formation.

FIG. 17 shows an exemplary staple (250) that has been formed by staple forming pocket (210), securing two layers (92, 94) of tissue in apposition. Staple (250) includes a crown (252), a first leg (270) having a tissue piercing tip (272), and a second leg (290) having a tissue piercing tip (292). As shown, legs (270, 290) are bent toward each other, with tips (272, 292) passing through a plane along which crown (252) lies. The formation of staple (250) is illustrated in FIGS. 18A-18E. When tips (272, 292) initially contact surfaces (222, 242), legs (270, 290) are substantially straight and perpendicular to crown (252). As staple (250) is driven further toward staple forming pocket (210), to the point where each tip (272, 292) reaches the apex ($A_1$) of each respective channel (220, 240), surfaces (222, 242) cammingly drive tips (272, 292) toward each other, which results in legs (270, 290) bending toward each other as shown in FIG. 18B. As staple (250) is driven further toward staple forming pocket (210), surfaces (224, 244) cammingly drive tips (272, 292) toward crown (252) as shown in FIG. 18C. As staple (250) is driven further toward staple forming pocket (210), surfaces (222, 224, 242, 244) continue to deform legs (270, 290) such that tips (272, 292) clear dividing wall surface (260) as shown in FIG. 18D. Once staple (250) is fully driven into staple forming pocket (210), tips (272, 292) pass crown (252), as shown in FIG. 18E and in FIG. 17. Thus, tips (272, 292) are driven through both layers (92, 94) of tissue twice, with tips (272, 292) being positioned past the same side of layer (92) as crown (252). It should be noted that formed staple (250) has a "B" shape in this example. It should also be noted that tips (272, 292) are positioned on the same lateral side of crown (252) after staple (250) is formed in this example. In some instances, tips (272, 292) do not pass crown (252), but nevertheless pass through at least layer (94) and perhaps layer (92) twice.

Referring back to FIG. 18A, it should be noted that staple forming pocket (210) provides a distance ($d_1$) between a longitudinal axis of each leg (270, 290) and a parallel axis passing through the apex ($A_1$) of each corresponding channel (220, 240). In addition, staple forming pocket (210) provides a distance ($d_2$) between a vertical axis passing through the center of crown (252) and a parallel axis passing through the apex ($A_1$) of each channel (220, 240). As will be described in greater detail below, it may be desirable in some instances to shift apexes ($A_1$) closer toward the vertical axis passing through the center of crown (252), thereby increasing distance ($d_1$) and reducing distance ($d_2$). In either case, it should be understood that it may be desirable in some instances to have the distance ($d_1$) on one side of pocket (210) be greater than the corresponding distance ($d_1$) on the other side of pocket (210). Similarly, it may be desirable in some instances to have the distance ($d_2$) be greater on one side of pocket than the corresponding distance ($d_2$) on the other side of pocket (210). It is thus contemplated that a pocket may be asymmetric about a vertical plane that passes through dividing wall surface (260).

Figure 19:
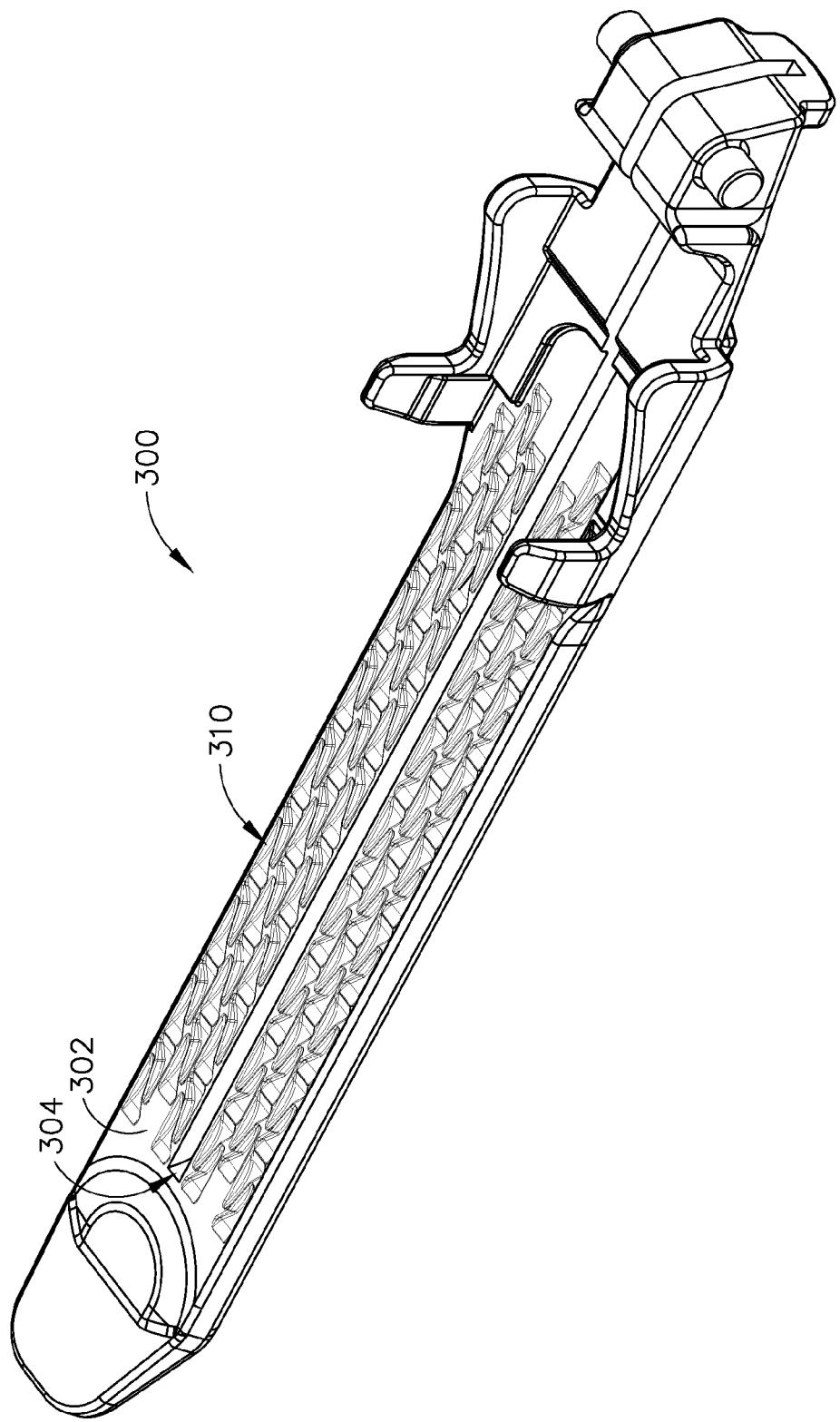
FIG. 19 depicts a perspective view of another exemplary alternative anvil that may be incorporated into the instrument of FIG. 1.
Figure 20:
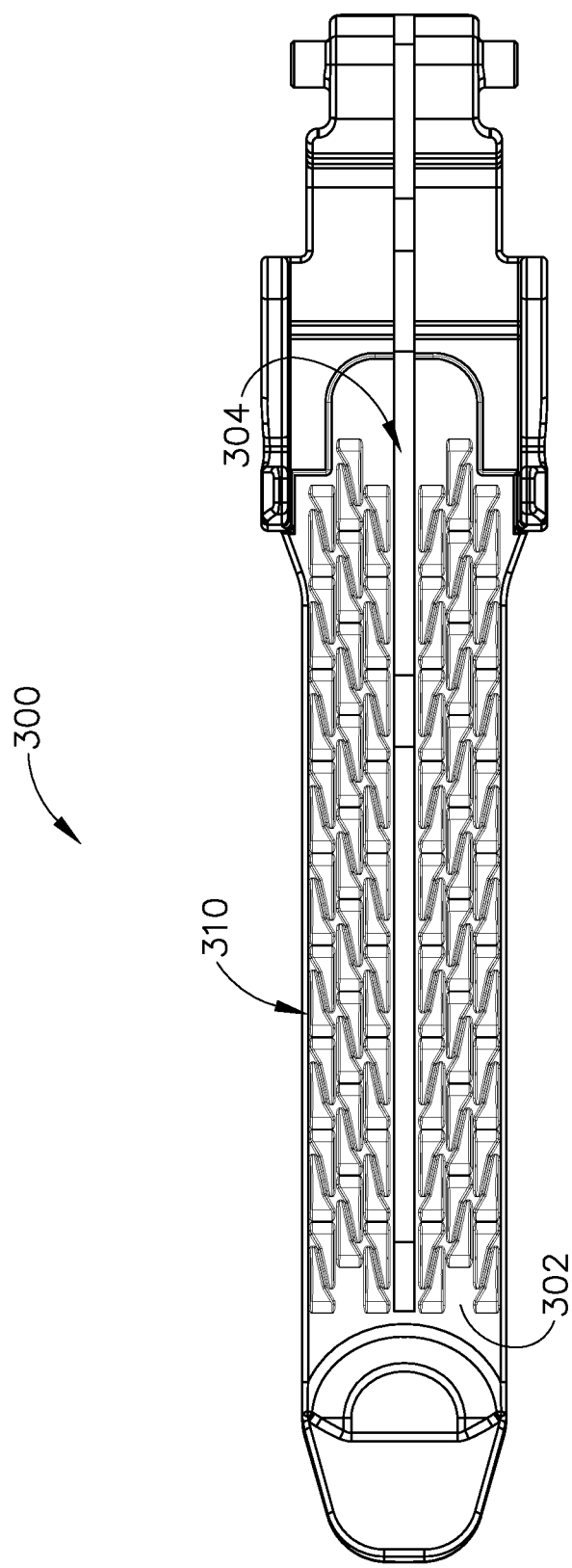
FIG. 20 depicts a bottom plan view of the anvil of FIG. 19.
Figure 21:
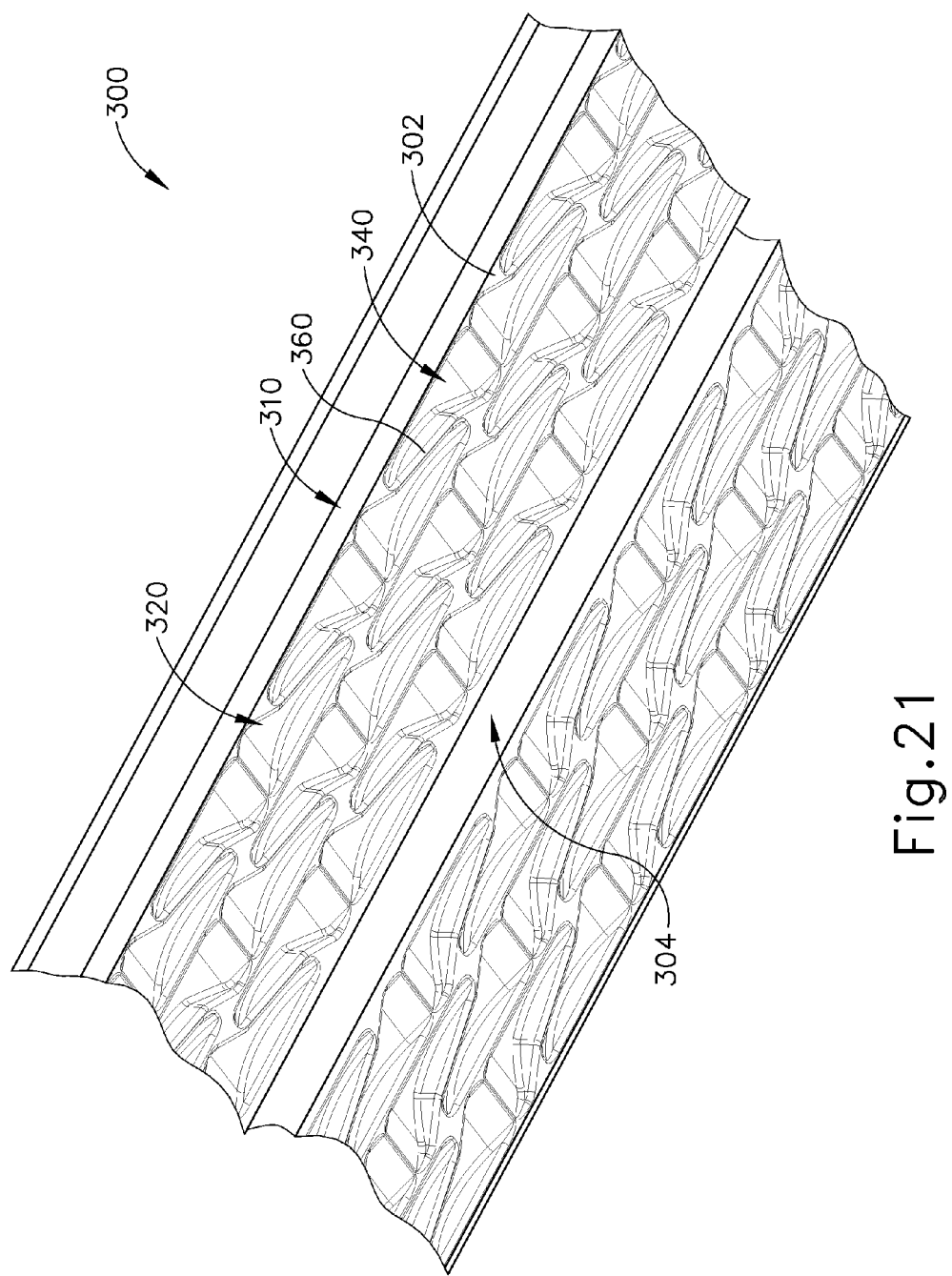
FIG. 21 depicts an enlarged perspective view of staple forming pockets of the anvil of FIG. 19.

B. Exemplary Staple Forming Pockets with Channels Separated by Full Oblique Wall FIGS. 19-21 show an exemplary anvil (300) that may be used in place of anvil (18) described above. Anvil (300) of this example defines a longitudinally extending slot (304), which is similar to anvil slot (42) described above. An upper portion of firing beam (14) translates through anvil slot (42) during a cutting/stapling stroke of instrument (10). Anvil (300) also includes a tissue contacting surface (302) that presses against tissue when the tissue is clamped between anvil (300) and upper deck (72) of staple cartridge (37). A series of staple forming pockets (310) are recessed relative to tissue contacting surface (302). In the present example, anvil (300) has three rows of staple forming pockets (310) on each side of slot (304). However, it should be understood that any other suitable number of rows of staple forming pockets (310) may be provided on each side of slot (304). By way of example only, some other versions may include two rows or more than three rows of staple forming pockets (310) on each side of slot (304). It should also be noted that, on each side of slot (304), each row of staple forming pockets (310) is longitudinally offset relative to the adjacent row of staple forming pockets (310). The results of such an offset would be similar to what is shown in FIG. 7, where formed staples (47) are longitudinally offset among adjacent rows. Of course, staple forming pockets (310) may have any other suitable arrangements relationships with each other.

Figure 22:
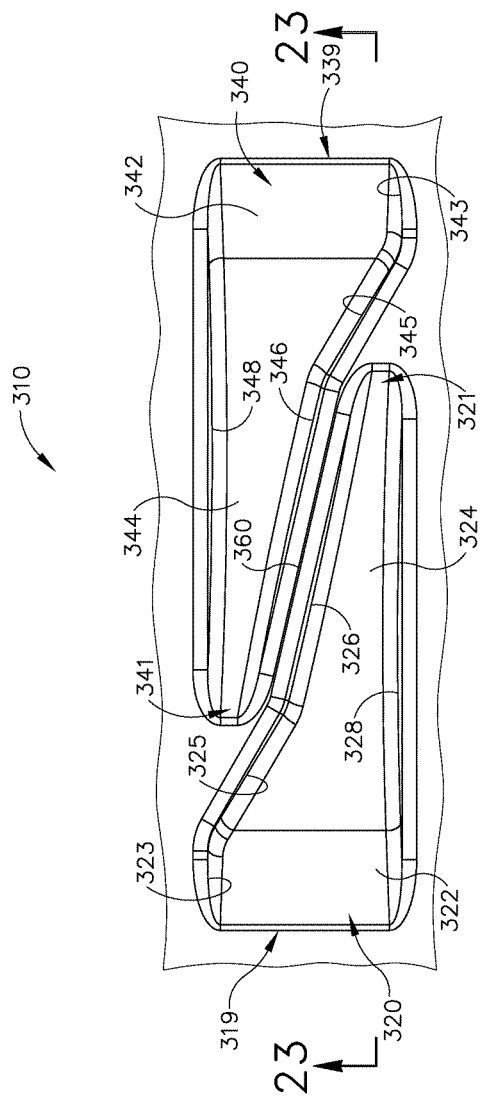
FIG. 22 depicts an enlarged plan view of a staple forming pocket of the anvil of FIG. 19.
Figure 23:
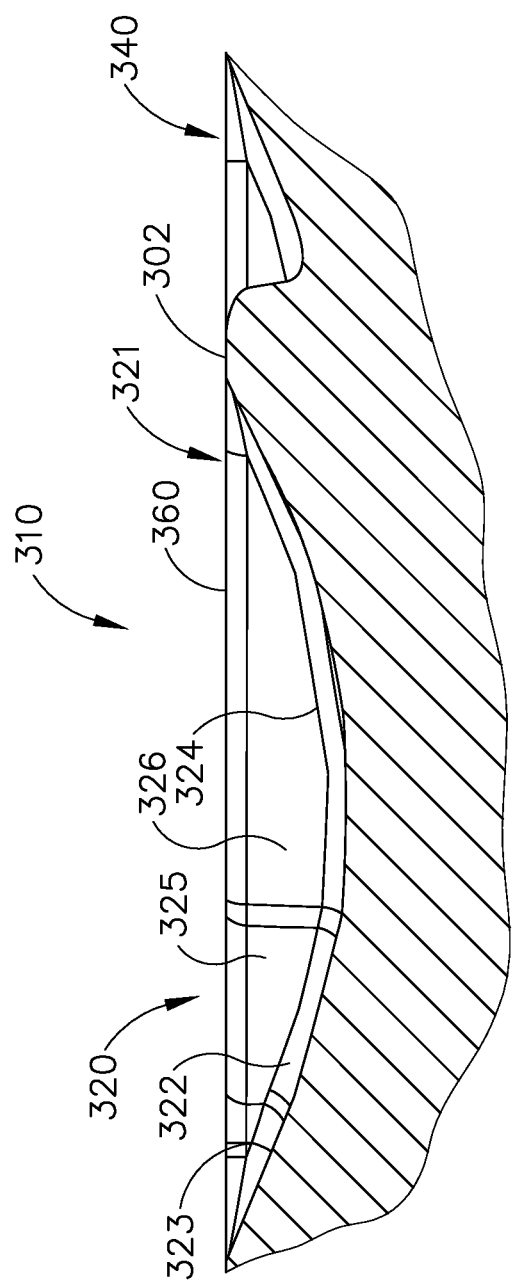
FIG. 23 depicts a perspective cross-sectional view of the staple forming pocket of FIG. 22, taken along line 23-23 of FIG. 22.

FIGS. 22-23 show staple forming pocket (310) in greater detail. It should be understood that all staple forming pockets (310) of anvil (300) may be similarly configured. Staple forming pocket (310) of this example provides a first channel (320) and a second channel (340). While channels (320, 340) are generally parallel with each other, channels (320, 340) are not aligned with each other in this example. A dividing wall (360) separates channels (320, 340). Wall (360) is obliquely oriented relative to slot (304) of anvil (300). Channels (320, 340) are asymmetric in this example, though there are substantial similarities between the configuration of channel (340) and the configuration of channel (320).

Channel (320) is longitudinally defined by a downwardly sloping concave surface (322), which smoothly transitions into an upwardly sloping concave surface (324), which terminates at tissue contacting surface (302) at a terminal end (321) of channel (320). In some instances, surface (322) is defined by a single radius. In some other instances, surface (322) is defined by more than one radius. In addition or in the alternative, surface (322) may include a combination of one or more surfaces defined by one or more radii and one or more flat surfaces that are vertical, horizontal, or otherwise angled.

Channel (320) is laterally defined on one side by a first sidewall (323), a second sidewall, (325), and a third sidewall (326). Channel (320) is laterally defined on the other side by a fourth sidewall (328). It should be understood that any other suitable number of sidewalls may be used to define channel (320). First sidewall (323) is generally parallel with fourth sidewall (328) in the present example, though it should be understood that other suitable relationships may be provided. Second sidewall (325) defines a first oblique angle relative to fourth sidewall (328). Third sidewall (326) defines a second oblique angle relative to fourth sidewall (328). The first oblique angle is greater than the second oblique angle. Thus, when viewing the width across the length of channel (320), channel (320) is widest at the staple leg entry end (319) and along the short length defined between first sidewall (323) and fourth sidewall (328). The width of channel (320) then drastically narrows along the part of the length defined between second sidewall (325) and fourth sidewall (328). The width of channel (320) continues to narrow (but less drastically) along the part of the length defined between third sidewall (326) and fourth sidewall (328). Channel (320) is at its narrowest width at terminal end (321).

In the present example, the transition between first sidewall (323) and second sidewall (325) is smooth, with a generally concave curvature. The transition between second sidewall (325) and third sidewall (326) is also smooth, with a generally convex curvature. In addition, the transitions between the upper boundaries of sidewalls (323, 325, 326, 328) and tissue contacting surface (302) are smooth, with a generally convex curvature. In some other versions, the edges between the upper boundaries of sidewalls (323, 325, 326, 328) and tissue contacting surface (302) are chamfered, providing a flat but angled lead-in from tissue contacting surface (302) to sidewalls (323, 325, 326, 328). Alternatively any other suitable types of transitions may be used. It should also be understood that all of sidewalls (323, 325, 326, 328) extend up to tissue contacting surface (302) in this example, excepting a relatively short and uniform rounded/chamfered transition about the upper perimeter defined by sidewalls (323, 325, 326, 328).

Channel (340) is longitudinally defined by a downwardly sloping concave surface (342), which smoothly transitions into an upwardly sloping concave surface (344), which terminates at tissue contacting surface (302) at a terminal end (341) of channel (340). In some instances, surface (342) is defined by a single radius. In some other instances, surface (342) is defined by more than one radius. In addition or in the alternative, surface (342) may include a combination of one or more surfaces defined by one or more radii and one or more flat surfaces that are vertical, horizontal, or otherwise angled.

Channel (340) is laterally defined on one side by a first sidewall (343), a second sidewall, (345), and a third sidewall (346). Channel (340) is laterally defined on the other side by a fourth sidewall (348). It should be understood that any other suitable number of sidewalls may be used to define channel (340). First sidewall (343) is generally parallel with fourth sidewall (348) in the present example, though it should be understood that other suitable relationships may be provided. Second sidewall (345) defines a first oblique angle relative to fourth sidewall (348). Third sidewall (346) defines a second oblique angle relative to fourth sidewall. The first oblique angle is greater than the second oblique angle. Thus, when viewing the width across the length of channel (340), channel (340) is widest at the staple leg entry end (339) and along the short length defined between first sidewall (343) and fourth sidewall (348). The width of channel (340) then drastically narrows along the part of the length defined between second sidewall (345) and fourth sidewall (348). The width of channel (340) continues to narrow (but less drastically) along the part of the length defined between third sidewall (346) and fourth sidewall (348). Channel (340) is at its narrowest width at terminal end (341).

In the present example, the transition between first sidewall (343) and second sidewall (345) is smooth, with a generally concave curvature. The transition between second sidewall (345) and third sidewall (346) is also smooth, with a generally convex curvature. In addition, the transitions between the upper boundaries of sidewalls (343, 345, 346, 348) and tissue contacting surface (302) are smooth, with a generally convex curvature. In some other versions, the edges between the upper boundaries of sidewalls (343, 345, 346, 348) and tissue contacting surface (302) are chamfered, providing a flat but angled lead-in from tissue contacting surface (302) to sidewalls (343, 345, 346, 348). Alternatively any other suitable types of transitions may be used. It should also be understood that all of sidewalls (343, 345, 346, 348) extend up to tissue contacting surface (302) in this example, excepting a relatively short and uniform rounded/chamfered transition about the upper perimeter defined by sidewalls (343, 345, 346, 348).

As can be seen in FIG. 22, sidewalls (326, 346) together define dividing wall (360). Dividing wall (360) extends to a height where the top of dividing wall (360) is substantially flush with tissue contacting surface (302). As can also be seen in FIG. 22, the transition from second sidewall (325) of channel (320) to third sidewall (326) of channel (320) is located within the same longitudinal region of staple forming pocket (310) as terminal end (341) of channel (340). In other words, the transition from second sidewall (325) of channel (320) to third sidewall (326) of channel (320) is located directly lateral to terminal end (341) of channel (340). Likewise, the transition from second sidewall (345) of channel (340) to third sidewall (346) of channel (340) is located within the same longitudinal region of staple forming pocket (310) as terminal end (321) of channel (320). In other words, the transition from second sidewall (345) of channel (340) to third sidewall (346) of channel (340) is located directly lateral to terminal end (321) of channel (320). It should be understood that staple forming pocket (310) generally defines a longitudinal axis extending from the left side of FIG. 22 to the right side of FIG. 22 (with FIG. 22 being viewed in a landscape orientation). The full length of staple forming pocket (310) extends along this longitudinal axis; while the full width of staple forming pocket (310) spans laterally relative to this longitudinal axis. A portion of staple forming pocket (310) that is associated with a particular point or range along the longitudinal axis may be regarded as a "longitudinal region" of staple forming pocket (310). A "longitudinal region" may thus include the full width of staple forming pocket (310) at a particular point or particular range of length along the longitudinal axis.

Figure 24:
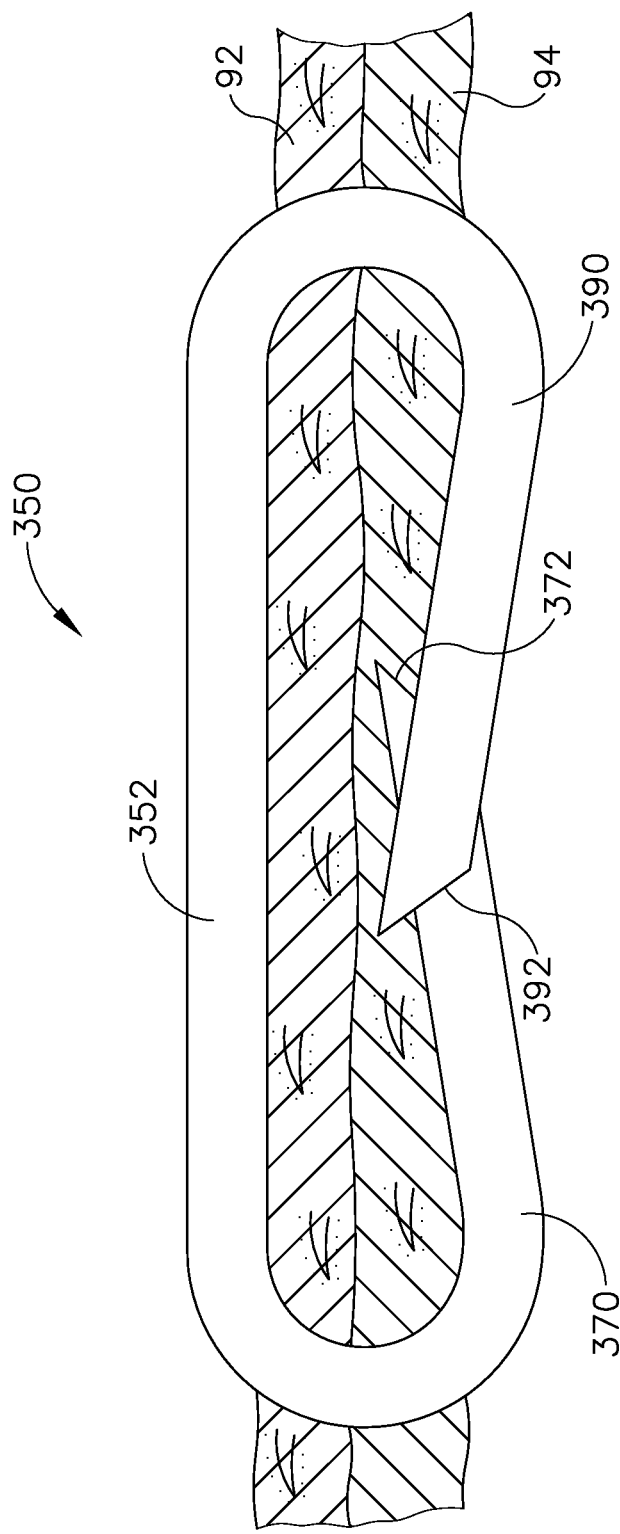
FIG. 24 depicts a side elevational view of an exemplary staple formed by the staple forming pocket of FIG. 19, disposed in tissue.
Figure 25A:
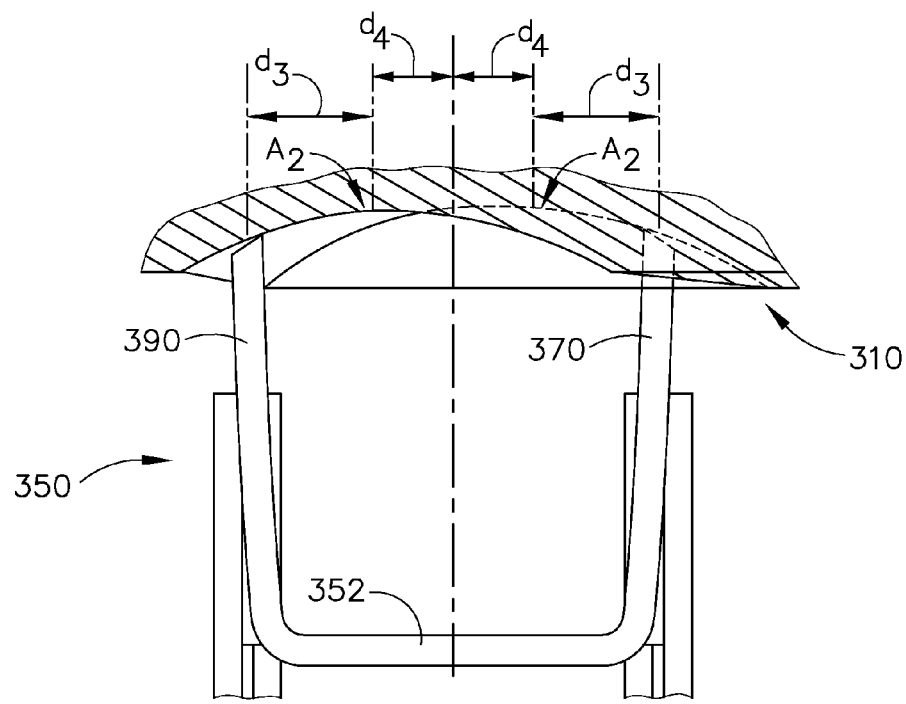
FIG. 25A depicts a side elevational view of the staple of FIG. 24 in an unformed state, initially contacting the staple forming pocket of FIG. 19 in a first stage of staple formation.
Figure 25B:
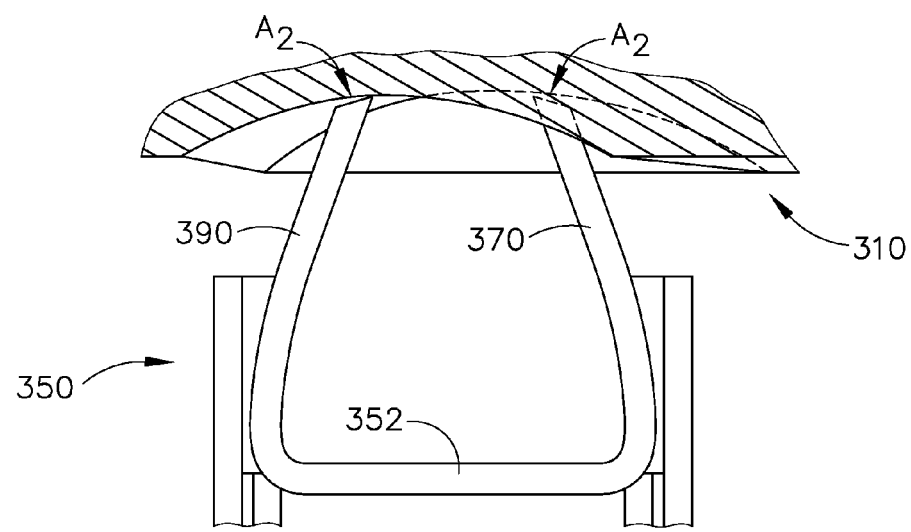
FIG. 25B depicts a side elevational view of the staple of FIG. 24 being driven into the staple forming pocket of FIG. 19 in a second stage of staple formation.
Figure 25C:
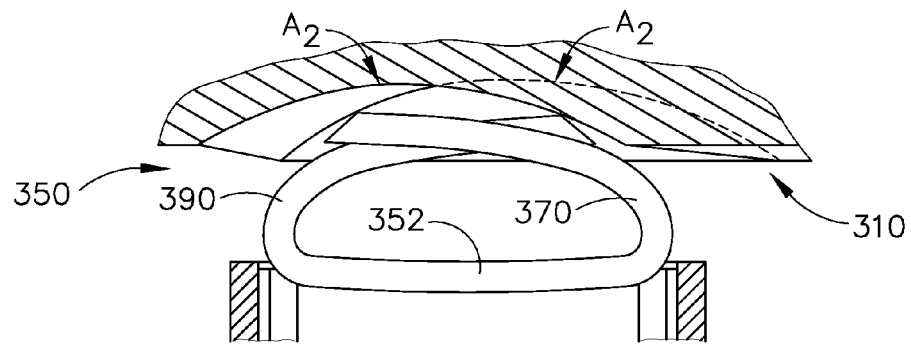
FIG. 25C depicts a side elevational view of the staple of FIG. 24 being driven into the staple forming pocket of FIG. 19 in a third stage of staple formation.

FIG. 24 shows an exemplary staple (350) that has been formed by staple forming pocket (310), securing two layers (92, 94) of tissue in apposition. Staple (350) includes a crown (352), a first leg (370) having a tissue piercing tip (372), and a second leg (390) having a tissue piercing tip (392). As shown, legs (370, 390) are bent toward each other, but legs (370, 390) do not pass through a plane along which crown (352) lies. The formation of staple (350) is illustrated in FIGS. 25A-25D. When tips (372, 392) initially contact surfaces (322, 342), legs (370, 390) are substantially straight and perpendicular to crown (352). In addition, legs (370, 390) and crown (352) all lie along a common vertical plane. As staple (350) is driven further toward staple forming pocket (310), to the point where each tip (372, 392) reaches the apex ($A_2$) of each respective channel (320, 340), surfaces (322, 342) cammingly drive tips (372, 392) toward each other, which results in legs (370, 390) bending toward each other as shown in FIG. 25B. As staple (350) is driven further toward staple forming pocket (310), sidewalls (324, 344) cammingly drive tips (372, 392) toward crown (352) as shown in FIG. 25C. In addition, sidewalls (325, 326) drive tip (372) laterally away from the vertical plane referred to above; while surfaces (345, 346) drive tip (392) laterally away from the vertical plane referred to above. Legs (370, 390) and crown (352) thus no longer lie along a common vertical plane at this stage. In particular, legs (370, 390) and tips (372, 392) have been driven laterally in opposite directions relative to crown (352).

Figure 25D:
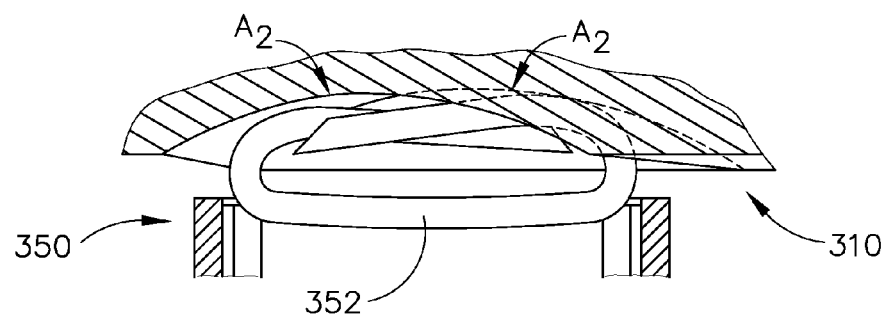
FIG. 25D depicts a side elevational view of the staple of FIG. 24 being fully driven into the staple forming pocket of FIG. 19 at a final stage of staple formation.
Figure 26:
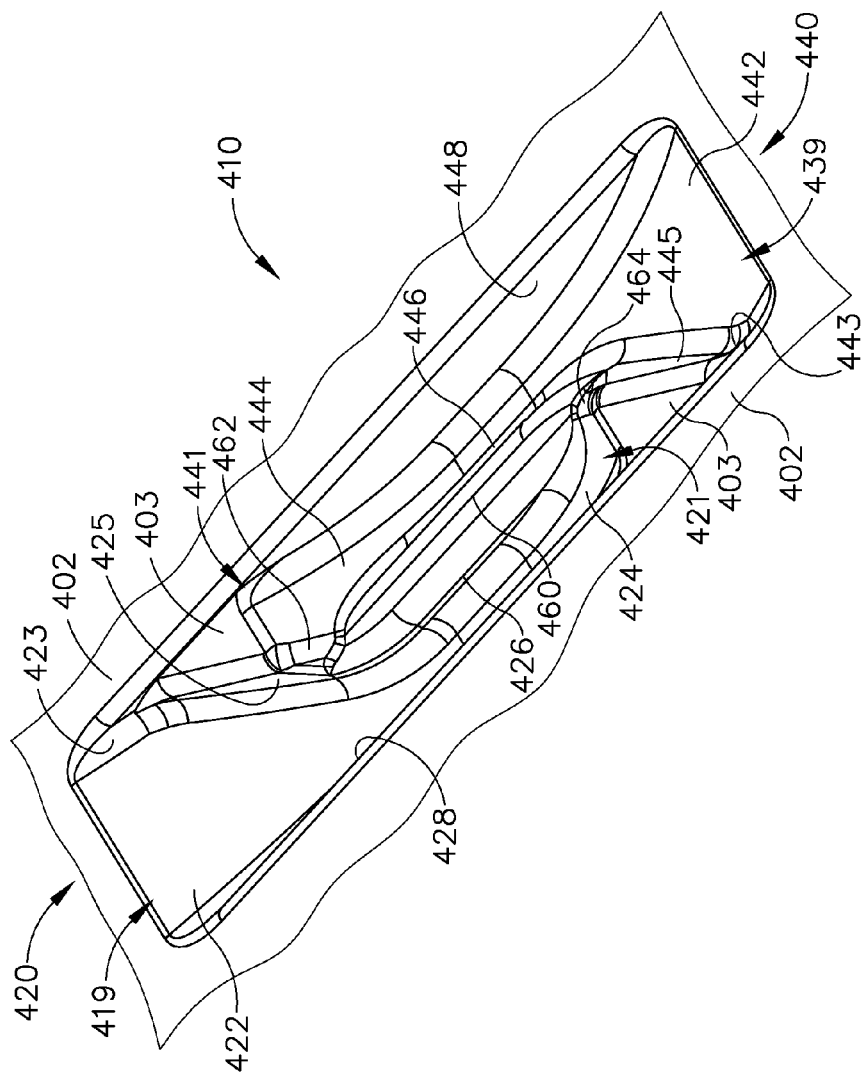
FIG. 26 depicts a perspective view of another exemplary alternative staple forming pocket that may be incorporated in to the anvil of the instrument of FIG. 1.

As staple (350) is driven further toward staple forming pocket (310), surfaces (322, 324, 342, 344) and sidewalls (324, 324, 325, 326) continue to deform legs (370, 390) such that tips (372, 392) are eventually positioned at the respective terminal ends (321, 341) of staple forming pockets (320, 340) as shown in FIG. 25D. Thus, tips (372, 392) only pass through layer (92) of tissue once in this example. In some instances, however, tips (372, 392) are driven to the point where they pass back into layer (94) of tissue as shown in FIG. 24. In some other instances, tips (372, 392) do not pass back into layer (94), such that tips (372, 392) only pass through layer (94) of tissue once. Regardless of whether tips (372, 392) pass back through layer (94) of tissue a second time, it should be understood that tips (372, 392) may be laterally offset relative to a vertical plane passing along the length of crown (352). In particular, tip (372) may be positioned on one lateral side of such a plane while tip (392) is positioned on the other lateral side of such a plane. The resulting lateral offset form may have an appearance similar to that shown in FIG. 34, which will be described in greater detail below.

Referring back to FIG. 25A, it should be noted that staple forming pocket (310) provides a distance ($d_3$) between a longitudinal axis of each leg (370, 390) and a parallel axis passing through the apex ($A_2$) of each corresponding channel (320, 340). In addition, staple forming pocket (310) provides a distance ($d_4$) between a vertical axis passing through the center of crown (352) and a parallel axis passing through the apex ($A_2$) of each channel (320, 340). As can be seen by comparing FIG. 25A with FIG. 18A, the distance ($d_3$) is greater than the distance ($d_1$), with the distance ($d_4$) being less than the distance ($d_2$). Thus, the apexes ($A_2$) in staple forming pocket (310) are closer to the vertical axis passing through the center of crown (352) than the apexes ($A_1$) of staple forming pocket (210) are to the vertical axis passing through the center of crown (252). Such a difference in configuration may promote inward bending of legs (370, 390) better, may minimize the elongation of the entry hole ultimately created by each leg (370, 390) in tissue, and/or may provide other results. In addition, it should be noted that channels (320, 340) have a greater length than channels (220, 240), which may reduce the likelihood of legs (370, 390) undesirably exiting channels (320, 340) before staple formation is complete. In some versions, channels (320, 340) are also deeper than channels (220, 240), which may assist in preventing tips (372, 392) from passing through at least layer (92) if not both layers (92, 94) a second time during staple formation.

In some settings, a staple (350) formed by staple forming pocket (310) may provide greater hemostasis of apposed tissue layers (92, 94), may provide greater structural integrity with respect to the apposition of tissue layers (92, 94), may have a reduced likelihood to undesirably pull through tissue layers (92, 94), may provide a reduced likelihood of tissue later tearing at the staple line, and/or may otherwise minimize trauma to tissue layers (92, 94), particularly when compared to staple (250) formed by staple forming pocket (210). When sealing certain tissue structures (e.g., a fragile artery, etc.), it may be desirable to minimize the amount of tissue puncturing by a staple. Formed staple (350) may minimize such puncturing (e.g., as compared to formed staple (250)) by not passing back trough layer (92) a second time; and in some instances not passing back through layer (94) a second time. By minimizing the fold-back motion of staple legs (370, 390) formed by staple forming pocket (310), the resulting formed staple (350) may bear more resemblance and functional similarity to a secure tissue clip than a conventional staple. Such a clip-like configuration may result in more tissue being captured between legs (370, 390) and crown (352) than might otherwise be captured between legs (270, 290) and crown (252); which may in turn result in better tissue integrity and a reduced tendency for the tissue to tear near staple (350). Minimizing the fold-back motion of staple legs (370, 390) during the process of staple formation may also reduce the total force required to form staple (350); as compared to the forces required to form a staple using a conventional staple forming pocket. This may reduce the force required to advance firing beam (14) distally during a firing stroke.

C. Exemplary Staple Forming Pockets with Channels Separated by Partial Wall

FIGS. 26-29 show another merely exemplary staple forming pocket (410) that may be readily incorporated into any of the anvils (18, 200, 300) referred to herein, among others. Staple forming pocket (410) of this example provides a first channel (420) and a second channel (440). While channels (420, 440) are generally parallel with each other, channels (420, 440) are not aligned with each other in this example. A dividing wall (460) separates channels (420, 440). Wall (460) is parallel with the slot (42, 204, 304) of anvil (18, 200, 300). Channels (420, 440) are asymmetric in this example, though there are substantial similarities between the configuration of channel (440) and the configuration of channel (420).

Channel (420) is longitudinally defined by a downwardly sloping concave surface (422), which smoothly transitions into an upwardly sloping concave surface (424), which terminates at recessed surface (403) at a terminal end (421) of channel (420). In some instances, surface (422) is defined by a single radius. In some other instances, surface (422) is defined by more than one radius. In addition or in the alternative, surface (422) may include a combination of one or more surfaces defined by one or more radii and one or more flat surfaces that are vertical, horizontal, or otherwise angled. Recessed surface (403) is recessed below tissue contacting surface (402) in the present example. In some instances, this may reduce localized pressure on tissue during a stapling sequence.

Channel (420) is laterally defined on one side by a first sidewall (423), a second sidewall, (425), and a third sidewall (426). Channel (420) is laterally defined on the other side by a fourth sidewall (428). It should be understood that any other suitable number of sidewalls may be used to define channel (420). First sidewall (423) is generally parallel with fourth sidewall (428) in the present example, though it should be understood that other suitable relationships may be provided. Second sidewall (425) defines an oblique angle relative to fourth sidewall (428). Third sidewall (426) is generally parallel with fourth sidewall (428). Thus, when viewing the width across the length of channel (420), channel (420) is widest at the staple leg entry end (419) and along the short length defined between first sidewall (423) and fourth sidewall (428). The width of channel (420) then drastically narrows along the part of the length defined between second sidewall (425) and fourth sidewall (428). The width of channel (420) remains substantially consistently narrow along the remaining length of channel (420), defined between third sidewall (426) and fourth sidewall (428) until channel (420) reaches its terminal end (421).

In the present example, the transition between first sidewall (423) and second sidewall (425) is smooth, with a generally concave curvature. The transition between second sidewall (425) and third sidewall (426) is also smooth, as is the transition between second sidewall (425) and recessed surface (403), with a generally convex curvature. In addition, the transitions between the upper boundaries of sidewalls (423, 426, 428) and tissue contacting surface (402) are smooth, with a generally convex curvature. In some other versions, the edges between the upper boundaries of sidewalls (423, 426, 428) and tissue contacting surface (402) are chamfered, providing a flat but angled lead-in from tissue contacting surface (402) to sidewalls (423, 426, 428). Alternatively any other suitable types of transitions may be used. It should also be understood that all of sidewalls (423, 426, 428) extend up to tissue contacting surface (402) in this example, excepting a relatively short and uniform rounded/chamfered transition about the upper perimeter defined by sidewalls (423, 426, 428).

Channel (440) is longitudinally defined by a downwardly sloping concave surface (442), which smoothly transitions into an upwardly sloping concave surface (444), which terminates at tissue contacting surface (402) at a terminal end (441) of channel (440). Channel (440) is laterally defined on one side by a first sidewall (443), a second sidewall, (445), and a third sidewall (446). In some instances, surface (442) is defined by a single radius. In some other instances, surface (442) is defined by more than one radius. In addition or in the alternative, surface (442) may include a combination of one or more surfaces defined by one or more radii and one or more flat surfaces that are vertical, horizontal, or otherwise angled.

Channel (440) is laterally defined on the other side by a fourth sidewall (448). First sidewall (443) is generally parallel with fourth sidewall (448). Second sidewall (445) defines an oblique angle relative to fourth sidewall (448). It should be understood that any other suitable number of sidewalls may be used to define channel (440). Third sidewall (446) is generally parallel with fourth sidewall (448), though it should be understood that other suitable relationships may be provided. Thus, when viewing the width across the length of channel (440), channel (440) is widest at the staple leg entry end (439) and along the short length defined between first sidewall (443) and fourth sidewall (448). The width of channel (440) then drastically narrows along the part of the length defined between second sidewall (445) and fourth sidewall (448). The width of channel (440) remains substantially consistently narrow along the remaining length of channel (440), defined between third sidewall (446) and fourth sidewall (448) until channel (440) reaches its terminal end (441).

In the present example, the transition between first sidewall (443) and second sidewall (445) is smooth, with a generally concave curvature. The transition between second sidewall (445) and third sidewall (446) is also smooth, as is the transition between second sidewall (445) and recessed surface (403), with a generally convex curvature. In addition, the transitions between the upper boundaries of sidewalls (443, 446, 448) and tissue contacting surface (402) are smooth, with a generally convex curvature. In some other versions, the edges between the upper boundaries of sidewalls (443, 446, 448) and tissue contacting surface (402) are chamfered, providing a flat but angled lead-in from tissue contacting surface (402) to sidewalls (443, 446, 448). Alternatively any other suitable types of transitions may be used. It should also be understood that all of sidewalls (443, 446, 448) extend up to tissue contacting surface (402) in this example, excepting a relatively short and uniform rounded/chamfered transition about the upper perimeter defined by sidewalls (443, 446, 448).

Figure 27:
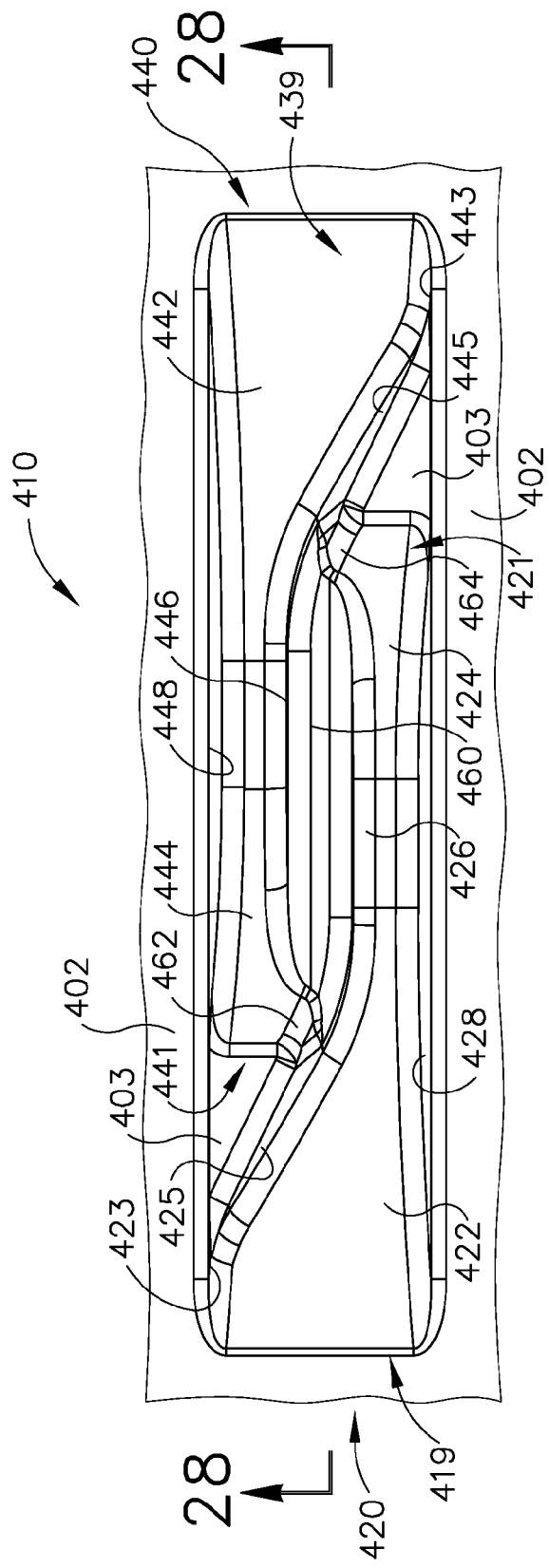
FIG. 27 depicts an enlarged plan view of the staple forming pocket of FIG. 26.
Figure 28:
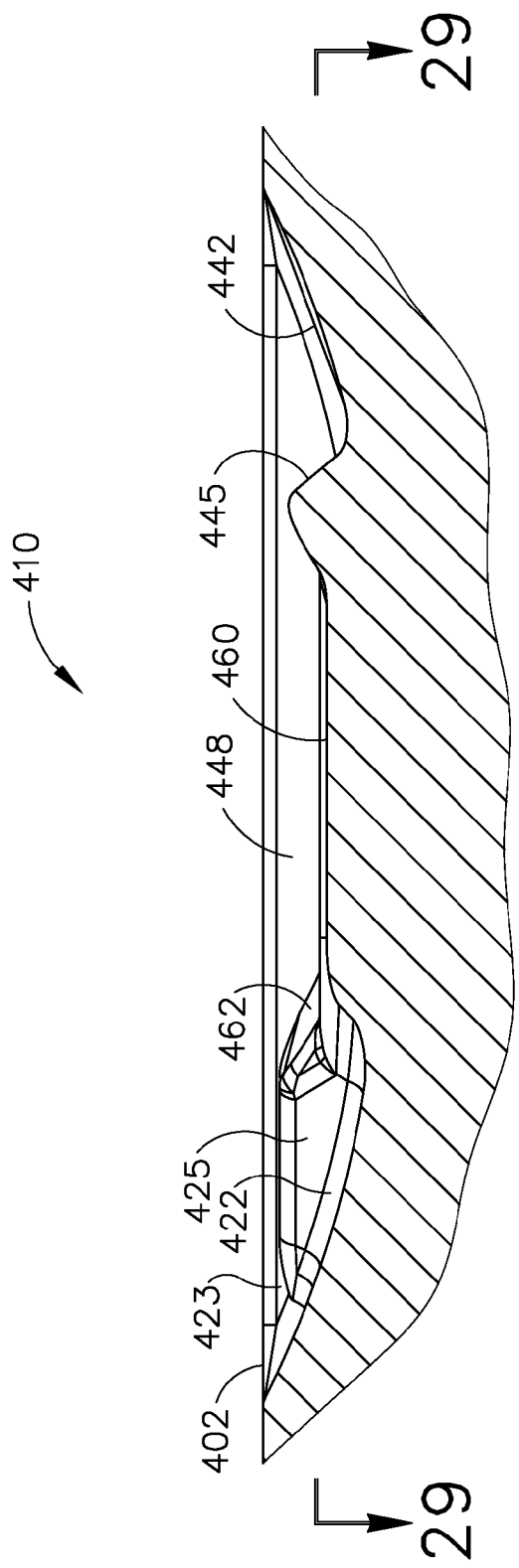
FIG. 28 depicts a cross-sectional view of the staple forming pocket of FIG. 26, taken along line 28-28 of FIG. 27.
Figure 29:
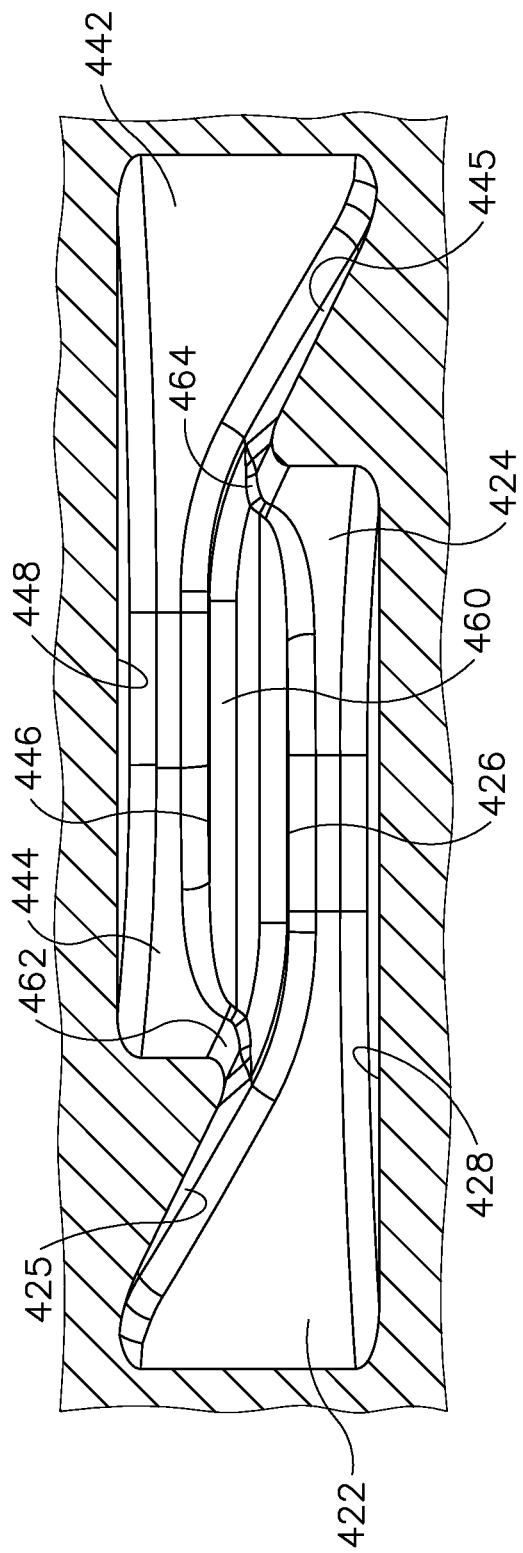
FIG. 29 depicts a cross-sectional view of the staple forming pocket of FIG. 26, taken along line 29-29 of FIG. 28.
Figure 30:
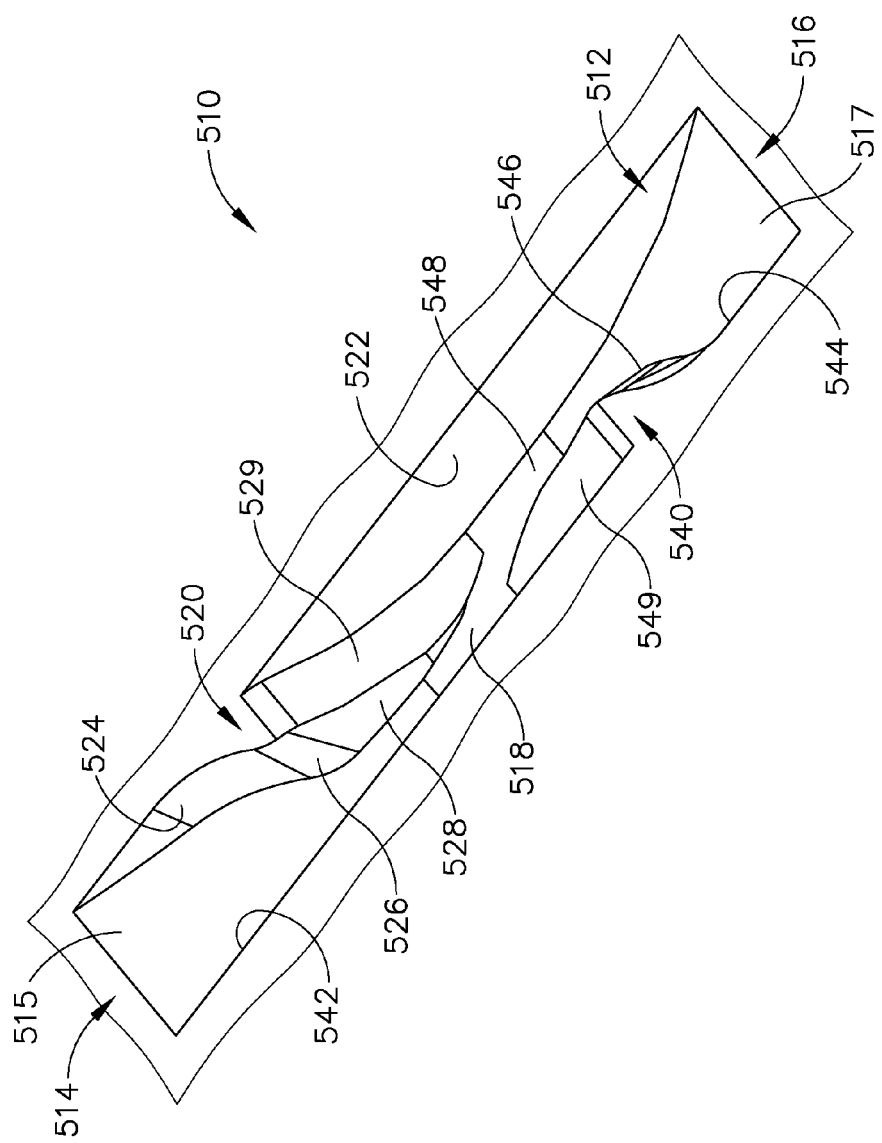
FIG. 30 depicts a perspective view of another exemplary alternative staple forming pocket that may be incorporated in to the anvil of the instrument of FIG. 1.
Figure 31:
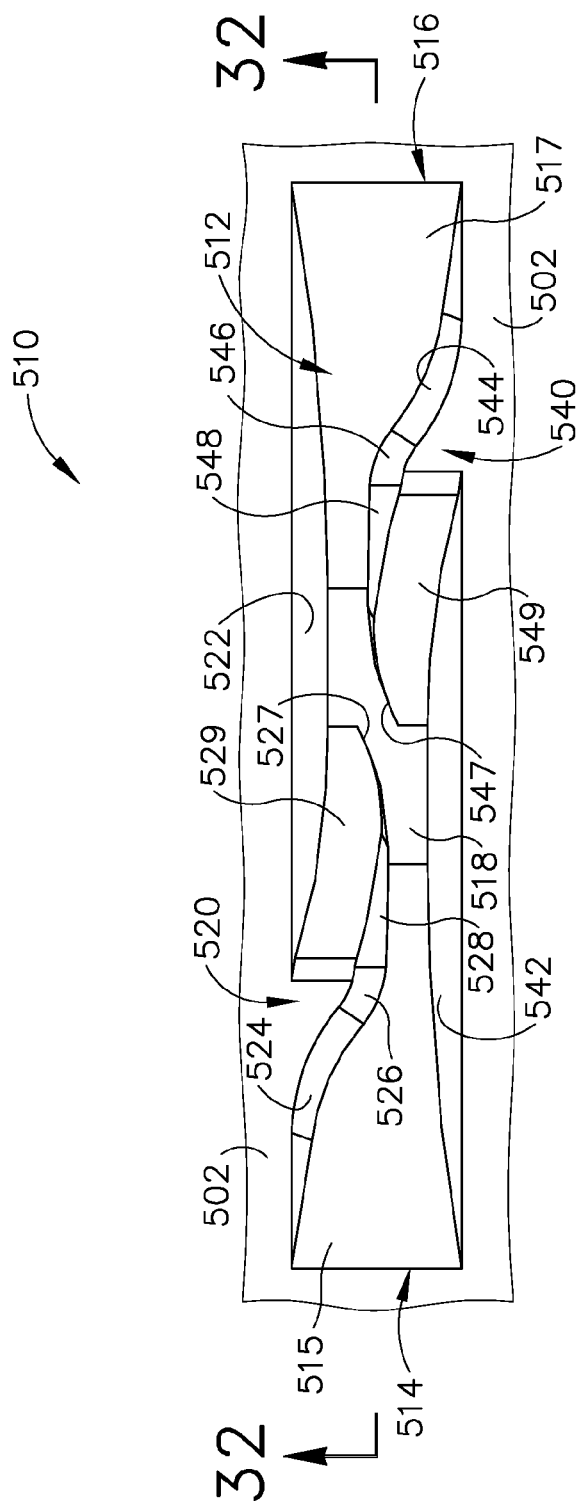
FIG. 31 depicts an enlarged plan view of the staple forming pocket of FIG. 30.

As can be seen in FIGS. 27 and 29, sidewalls (426, 446) together define dividing wall (460). Unlike dividing wall (360) described above, dividing wall (460) of this example is not flush with tissue contacting surface (402); and is instead recessed relative to tissue contacting surface (402) as best seen in FIG. 28. A pair of edges (462, 464) provide a transition from tissue contacting surface (402) to dividing wall (460). Edges (462, 464) are obliquely oriented relative to slot (42, 204, 304) of anvil (18, 200, 300) and further provide a vertically angled transition down to dividing wall (460).

As best seen in FIG. 27, edge (462) is located within the same longitudinal region of staple forming pocket (410) as the transition from second sidewall (425) of channel (420) to third sidewall (426) of channel (420); and terminal end (441) of channel (440). In other words, edge (462) is located generally lateral to the transition from second sidewall (425) of channel (420) to third sidewall (426) of channel (420); and generally lateral to terminal end (441) of channel (440). Likewise, edge (464) is located within the same longitudinal region of staple forming pocket (410) as the transition from second sidewall (445) of channel (440) to third sidewall (446) of channel (440); and terminal end (421) of channel (420). In other words, edge (464) is located generally lateral to the transition from second sidewall (445) of channel (440) to third sidewall (446) of channel (440); and generally lateral to terminal end (421) of channel (420).

Figure 34:
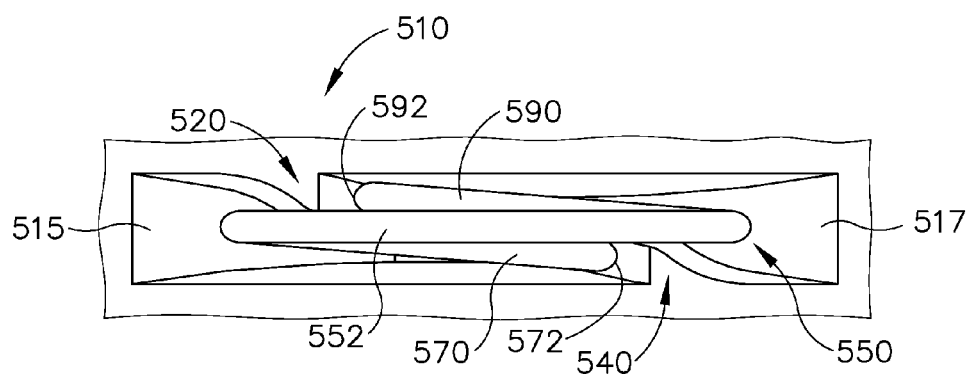
FIG. 34 depicts a top plan view of the staple of FIG. 33A having been fully driven into the staple forming pocket of FIG. 30.

A staple formed by staple forming pocket (410) may look similar to staple (350) shown in FIG. 24. In particular, surfaces (422, 442) may drive tips (372, 374) toward each other as legs (370, 390) are initially driven into respective channels (420, 440). As staple (350) is further driven into staple forming pocket (410), surfaces (424, 444) may drive tips toward crown (352). In addition, sidewall (425) may drive tip (372) in one direction laterally away from a vertical plane passing through dividing wall (460) and crown (352); while sidewall (445) drives tip (392) in the opposite direction laterally away from the same vertical plane passing through dividing wall (460) and crown (352). Surfaces (422, 424, 442, 444) and sidewalls (425, 426, 428, 445, 446, 448) may ultimately deform legs (370, 390) to the point where they are configured similar to what is shown in FIGS. 24 and 34. For instance, staple forming pocket (410) may form a staple (350) where tips (372, 392) only pass back into layer (94) (if at all), without also passing back into layer (92) a second time; and where tips (372, 392) are laterally offset relative to a vertical plane passing along the length of crown (352).

It should be understood that each channel (420, 440) may have a respective apex, and that the spacing of these apexes may be similar to the spacing of apexes ($A_2$) of channels (320, 340) described above. In other words, the apexes in staple forming pocket (410) may be closer to a vertical axis passing through the center of an associated staple crown than the apexes ($A_1$) of staple forming pocket (210) are to the vertical axis passing through the center of crown (252).

Such a difference in configuration may promote inward bending of the legs better, may minimize the elongation of the entry hole ultimately created by each staple leg in tissue, and/or may provide other results. In addition, it should be noted that channels (420, 440) have a greater length than channels (220, 240), which may reduce the likelihood of associated staple legs undesirably exiting channels (420, 440) before staple formation is complete. In some versions, channels (420, 440) are also deeper than channels (220, 240), which may assist in preventing associated staple leg tips from passing through at least layer (92) if not both layers (92, 94) a second time during staple formation.

In some settings, a staple formed by staple forming pocket (410) may provide greater hemostasis of apposed tissue layers (92, 94), may provide greater structural integrity with respect to the apposition of tissue layers (92, 94), may have a reduced likelihood to undesirably pull through tissue layers (92, 94), may provide a reduced likelihood of tissue later tearing at the staple line, and/or may otherwise minimize trauma to tissue layers (92, 94), particularly when compared to staple (250) formed by staple forming pocket (210). When sealing certain tissue structures (e.g., a fragile artery, etc.), it may be desirable to minimize the amount of tissue puncturing by a staple. A staple formed by pocket (410) may minimize such puncturing (e.g., as compared to formed staple (250)) by not passing back trough layer (92) a second time; and in some instances not passing back through layer (94) a second time. By minimizing the fold-back motion of the staple legs formed by staple forming pocket (410), the resulting formed staple may bear more resemblance and functional similarity to a secure tissue clip than a conventional staple. Such a clip-like configuration may result in more tissue being captured between the legs and the crown of the formed staple than might otherwise be captured between legs (270, 290) and crown (252); which may in turn result in better tissue integrity and a reduced tendency for the tissue to tear near the staple. Minimizing the fold-back motion of the staple legs during the process of staple formation may also reduce the total force required to form the staple using staple forming pocket (410); as compared to the forces required to form a staple using a conventional staple forming pocket. This may reduce the force required to advance firing beam (14) distally during a firing stroke.

Figure 32:
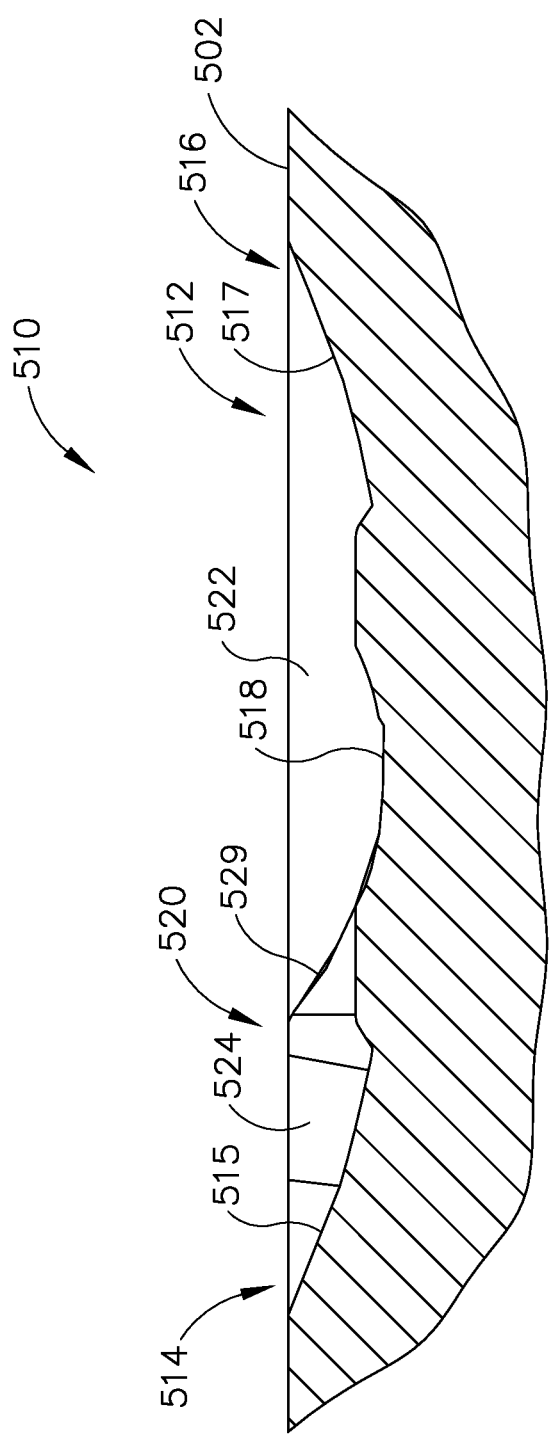
FIG. 32 depicts a cross-sectional view of the staple forming pocket of FIG. 30, taken along line 32-32 of FIG. 31.

D. Exemplary Staple Forming Pockets with Single Channel and Oblique Deflection Walls FIGS. 30-34 show another merely exemplary staple forming pocket (510) that may be readily incorporated into any of the anvils (18, 200, 300) referred to herein, among others. Staple forming pocket (510) of this example provides a single continuous channel (512) having a first cam feature (520) projecting laterally into channel (512) and a second cam feature (540) projecting laterally into channel (512). Channel (512) includes a first terminal end (514) for receiving a first staple leg and a second terminal end (516) for receiving a second staple leg. Channel (512) includes a concave entry surface (515) at end (514), a concave entry surface (517) at end (516), and a flat floor surface (518) that joins surfaces (515, 517) and provides a lowest point in the longitudinal mid region of channel (512). It should be understood that terms such as "downwardly" and "lowest" are used here in reference to pocket (510) being oriented as shown in FIG. 32, with tissue contacting surface (502) being presented upwardly. In actual use, tissue contacting surface (502) may in fact be presented downwardly, such that the orientation of pocket (510) would be flipped from the orientation shown in FIG. 32. Thus, terms such as "downwardly," "upwardly," "lowest," "top," "bottom," and the like should not be read as limiting how the inventors contemplate any of the devices herein being necessarily oriented during actual use of the devices.

A first outer sidewall (542) extends from first terminal end (514) to second cam feature (540). A second outer sidewall (522) extends from second terminal end (516) to first cam feature (520). Outer sidewalls (522, 542) are angled relative to a vertical plane passing longitudinally along the center of staple forming pocket (510), such that sidewalls (522, 542) provide a lead-in to surfaces (515, 514) and floor (518). In other words, the lateral spacing between sidewalls (522, 542) is greater at the top of sidewalls (522, 542) (i.e., at tissue contact surface (502)) than the lateral spacing between sidewalls (522, 542) at the bottom of sidewalls (522, 542).

First cam feature (520) includes a laterally concave sidewall (524), a convex transition region (526), and a longitudinal sidewall (528). It should be understood that the distance between laterally concave sidewall (524) and outer sidewall (542) is greater than the distance between longitudinal sidewall (528) and outer sidewall (542). A terminal convex sidewall (527) is located at the opposite end of longitudinal sidewall (528). First cam feature (520) also includes a ramp (529). As best seen in FIG. 32, ramp (529) is concave and is defined by a radius of curvature that is less than the radius of curvature defining surface (517). Ramp (529) thus presents a curve that is steeper than the curve presented by surface (517). Second cam feature (540) includes a laterally concave sidewall (544), a convex transition region (546), and a longitudinal sidewall (548). It should be understood that the distance between laterally concave sidewall (544) and outer sidewall (522) is greater than the distance between longitudinal sidewall (548) and outer sidewall (522). A terminal convex sidewall (547) is located at the opposite end of longitudinal sidewall (548). First cam feature (540) also includes a ramp (549). Ramp (549) is concave and is defined by a radius of curvature that is less than the radius of curvature defining surface (515). Ramp (549) thus presents a curve that is steeper than the curve presented by surface (515).

Figure 33A:
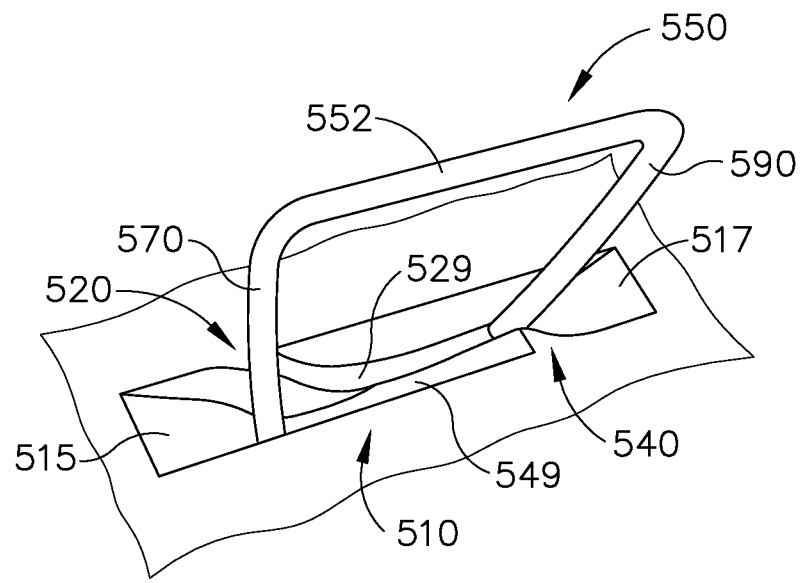
FIG. 33A depicts a perspective view of a staple being driven into the staple forming pocket of FIG. 30 in a first stage of staple formation.
Figure 33B:
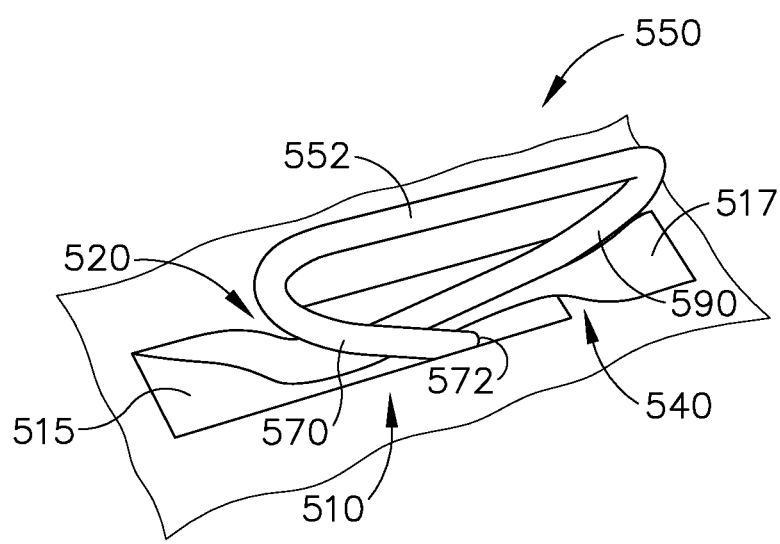
FIG. 33B depicts a perspective view of the staple of FIG. 33A being further driven into the staple forming pocket of FIG. 30 in a second stage of staple formation.
Figure 33C:
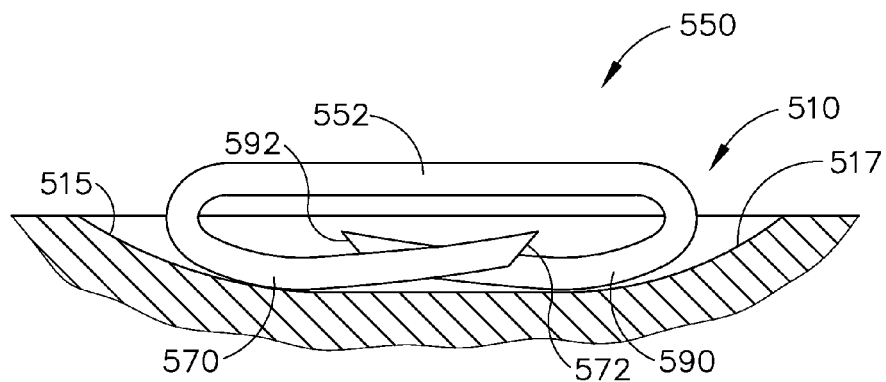
FIG. 33C depicts a side cross-sectional view of the staple of FIG. 33A being fully driven into the staple forming pocket of FIG. 30 at a final stage of staple formation.

FIGS. 33A-34 show an example of how a staple (550) may be formed by staple forming pocket (510). In particular, FIG. 33A shows how surfaces (515, 517) drive legs (570, 590) of staple (550) toward each other as staple (550) is initially driven into staple forming pocket (510). As staple (550) is driven further into staple forming pocket (510), floor surface (518) guides legs (570, 590) and sidewalls (524, 526, 528) cooperate to drive leg (570) in one direction laterally away from a vertical plane passing through crown (552); while sidewalls (544, 546, 548) cooperate to drive leg (590) in the opposite direction laterally away from the same vertical plane passing through crown (552). This lateral deflection of legs (570, 590) is shown in FIG. 33B. This lateral deflection of legs (570, 590) prevents legs (570, 590) from colliding with each other during formation of staple (550). It should be understood that this lateral deflection of legs (570, 590) also steers tip (572) into ramp (549) while also steering tip (592) into ramp (529). Ramps (529, 549) thus drive the corresponding tips (592, 572) upwardly toward a horizontal plane passing through crown (552), as shown in FIG. 33C. The lateral deflection of legs (570, 590) after staple (550) has been formed by staple forming pocket (510) can be best seen in FIG. 34. It should be understood that formed staple (550) may engage layers (92, 94) of tissue similar to the manner shown in FIG. 24. For instance, staple forming pocket (510) may form a staple (550) where tips (572, 592) only pass back into layer (94) (if at all), without also passing back into layer (92) a second time.

While staple forming pocket (510) of the present example defines just one single continuous channel (512), it should be understood that the combination of surface (517), floor (518), and ramp (529) may effectively define one sub-channel while the combination of surface (515), floor (518), and ramp (549) effectively define another sub-channel. It should further be understood that each sub-channel of staple forming pocket (510) may have an associated effective apex, and that the spacing of these effective apexes may be similar to the spacing of apexes ($A_2$) of channels (320, 340) described above. In other words, the effective apexes in staple forming pocket (510) may be closer to a vertical axis passing through the center of staple crown (552) than the apexes ($A_1$) of staple forming pocket (210) are to the vertical axis passing through the center of crown (252). Such a difference in configuration may promote inward bending of legs (570, 590) better, may minimize the elongation of the entry hole ultimately created by each staple leg (570, 590) in tissue, and/or may provide other results. In addition, it should be noted that the effective sub-channels of staple forming pocket (510) have a greater length than channels (220, 240), which may reduce the likelihood of associated staple legs undesirably exiting channels (420, 440) before staple formation is complete. In some versions, the effective sub-channels of staple forming pocket (510) are also deeper than channels (220, 240), which may assist in preventing associated staple leg tips from passing through at least layer (92) if not both layers (92, 94) a second time during staple formation.

In some settings, a staple (550) formed by staple forming pocket (510) may provide greater hemostasis of apposed tissue layers (92, 94), may provide greater structural integrity with respect to the apposition of tissue layers (92, 94), may have a reduced likelihood to undesirably pull through tissue layers (92, 94), may provide a reduced likelihood of tissue later tearing at the staple line, and/or may otherwise minimize trauma to tissue layers (92, 94), particularly when compared to staple (250) formed by staple forming pocket (210). When sealing certain tissue structures (e.g., a fragile artery, etc.), it may be desirable to minimize the amount of tissue puncturing by a staple. Formed staple (550) may minimize such puncturing (e.g., as compared to formed staple (250)) by not passing back trough layer (92) a second time; and in some instances not passing back through layer (94) a second time. By minimizing the fold-back motion of staple legs (570, 590) formed by staple forming pocket (510), the resulting formed staple (550) may bear more resemblance and functional similarity to a secure tissue clip than a conventional staple. Such a clip-like configuration may result in more tissue being captured between legs (570, 590) and crown (552) than might otherwise be captured between legs (270, 290) and crown (252); which may in turn result in better tissue integrity and a reduced tendency for the tissue to tear near staple (550). Minimizing the fold-back motion of staple legs (570, 590) during the process of staple formation may also reduce the total force required to form staple (550); as compared to the forces required to form a staple using a conventional staple forming pocket. This may reduce the force required to advance firing beam (14) distally during a firing stroke.

Figure 35:
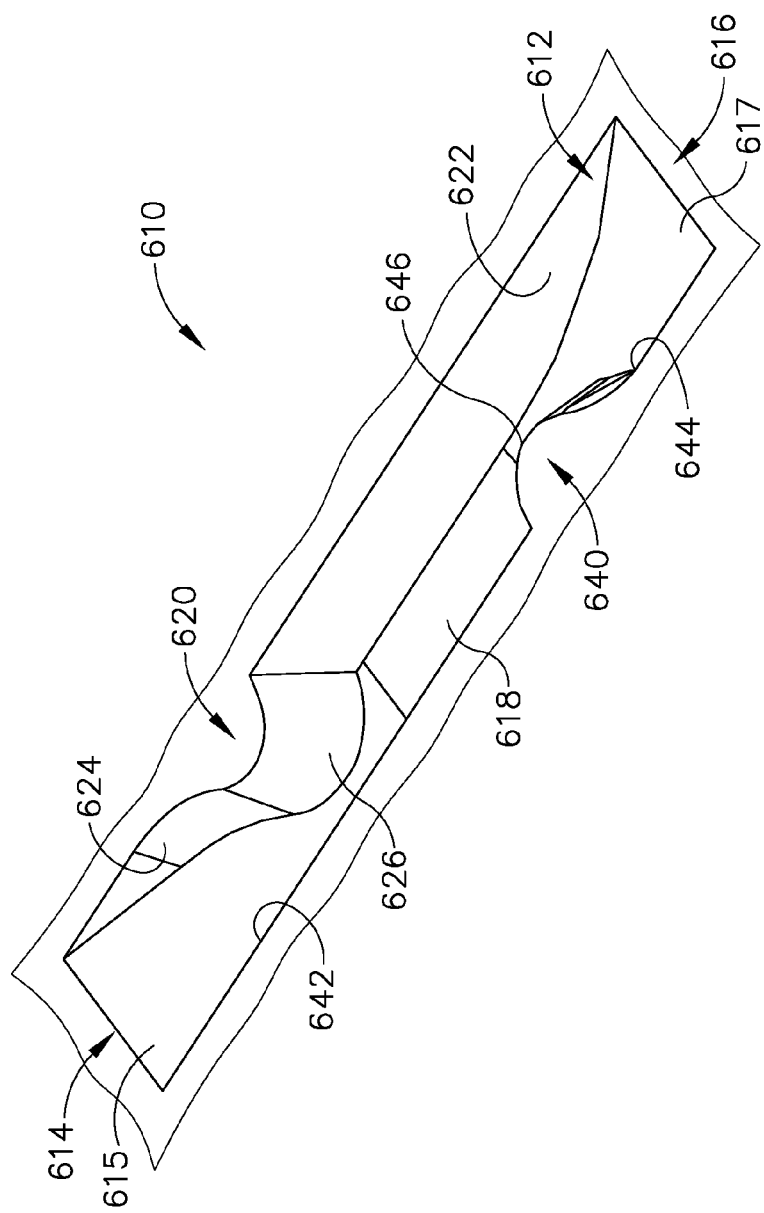
FIG. 35 depicts a perspective view of another exemplary alternative staple forming pocket that may be incorporated in to the anvil of the instrument of FIG. 1.
Figure 36:
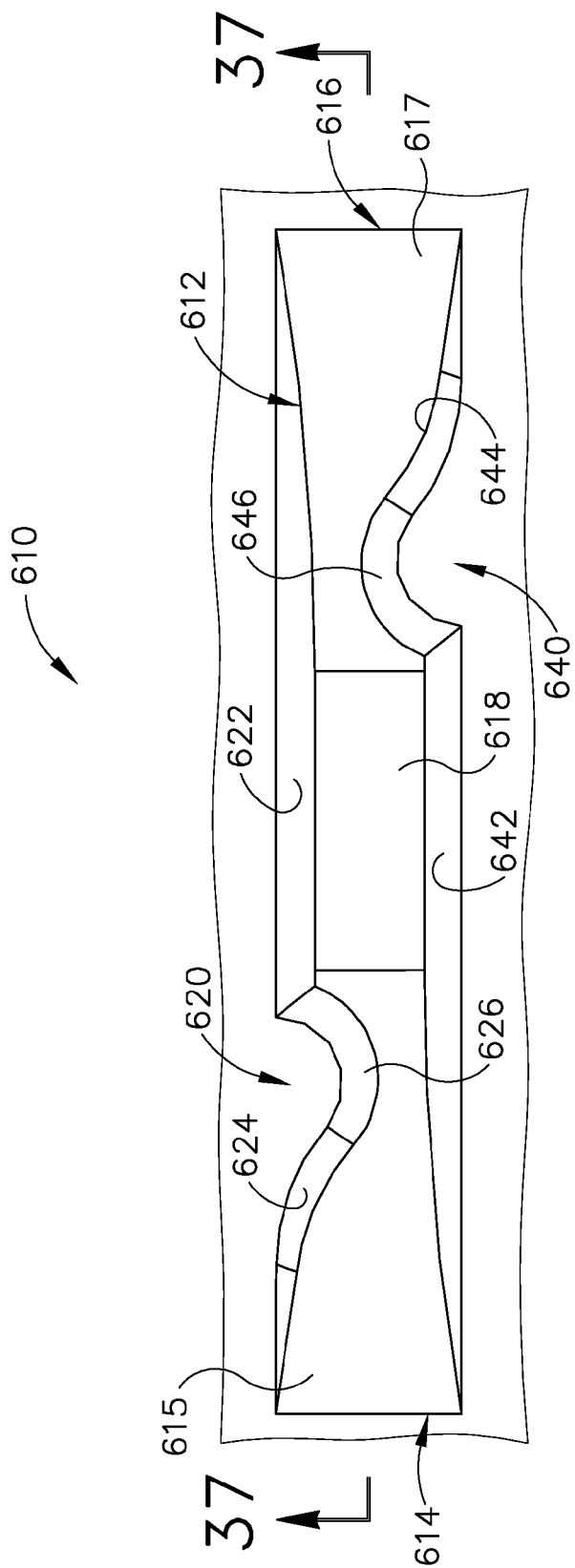
FIG. 36 depicts an enlarged plan view of the staple forming pocket of FIG. 35.
Figure 37:
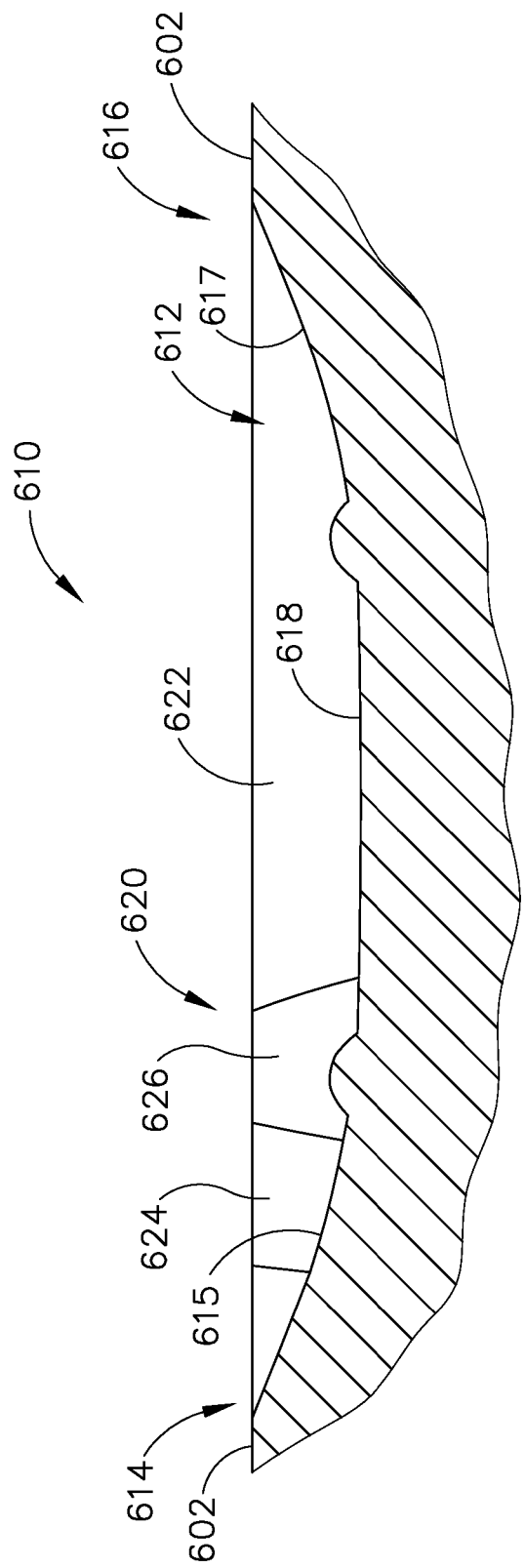
FIG. 37 depicts a cross-sectional view of the staple forming pocket of FIG. 35, taken along line 37-37 of FIG. 36.

E. Exemplary Staple Forming Pockets with Single Channel and Full Deflection Protrusions FIGS. 35-37 show another merely exemplary staple forming pocket (610) that may be readily incorporated into any of the anvils (18, 200, 300) referred to herein, among others. Staple forming pocket (610) of this example provides a single continuous channel (612) having a first deflection protrusion (620) projecting laterally into channel (612) and a second deflection protrusion (640) projecting laterally into channel (612). Channel (612) includes a first terminal end (614) for receiving a first staple leg and a second terminal end (616) for receiving a second staple leg. Channel (612) includes a concave entry surface (615) at end (614), a concave entry surface (617) at end (616), and a flat floor surface (618) that joins surfaces (615, 617) and provides a lowest point in the longitudinal mid region of channel (612).

A first outer sidewall (642) extends from first terminal end (614) to second deflection protrusion (640). A second outer sidewall (622) extends from second terminal end (616) to first deflection protrusion (620). Outer sidewalls (622, 642) are angled relative to a vertical plane passing longitudinally along the center of staple forming pocket (610), such that sidewalls (622, 642) provide a lead-in to surfaces (615, 617) and floor (618). In other words, the lateral spacing between sidewalls (622, 642) is greater at the top of sidewalls (622, 642) (i.e., at tissue contact surface (602)) than the lateral spacing between sidewalls (622, 642) at the bottom of sidewalls (622, 642).

First deflection protrusion (620) includes a laterally concave sidewall (624) leading to a convex sidewall (626), which terminates in second outer sidewall (622). Like sidewall (622), sidewalls (624, 626) are sloped relative to a vertical plane passing longitudinally along the center of staple forming pocket (610), such that sidewalls (624, 626) provide a lead-in to surfaces (615, 617) and floor (618). It should also be understood that sidewalls (624, 626) vertically extend all the way to the top of channel (612), such that the tops of sidewalls (624, 626) terminate at tissue contact surface (602).

Second deflection protrusion (640) includes a laterally concave sidewall (644) leading to a convex sidewall (646), which terminates in first outer sidewall (642). Like sidewall (642), sidewalls (644, 646) are sloped relative to a vertical plane passing longitudinally along the center of staple forming pocket (610), such that sidewalls (644, 646) provide a lead-in to surfaces (615, 617) and floor (618). It should also be understood that sidewalls (644, 646) vertically extend all the way to the top of channel (612), such that the tops of sidewalls (644, 646) terminate at tissue contact surface (602).

When a staple is driven into staple forming pocket (610), the result may be similar to the result shown in FIGS. 24 and 34. In particular, surfaces (615, 617) may drive the legs of the staple toward each other as the staple is initially driven into staple forming pocket (610). Protrusions (620, 640) may eventually deflect the legs of the staple laterally in opposite directions, such that the legs do not collide with each other during formation of the staple and such that the legs are ultimately positioned on opposite sides of a vertical plane passing through the crown of the staple (e.g., as shown in FIG. 34). The tips of the staple legs may ultimately pass through layers (92, 94) of tissue just once, without even passing back through layer (94). In some versions, the tips of the staple legs may at least pass back through layer (94) a second time (e.g., as shown in FIG. 24).

It should be understood that a staple formed by staple forming pocket (610) may provide greater hemostasis of apposed tissue layers (92, 94), may provide greater structural integrity with respect to the apposition of tissue layers (92, 94), may have a reduced likelihood to undesirably pull through tissue layers (92, 94), may provide a reduced likelihood of tissue later tearing at the staple line, and/or may otherwise minimize trauma to tissue layers (92, 94), particularly when compared to staple (250) formed by staple forming pocket (210). When sealing certain tissue structures (e.g., a fragile artery, etc.), it may be desirable to minimize the amount of tissue puncturing by a staple. A staple formed by pocket (610) may minimize such puncturing (e.g., as compared to formed staple (250)) by not passing back trough layer (92) a second time; and in some instances not passing back through layer (94) a second time. By minimizing the fold-back motion of the staple legs formed by staple forming pocket (610), the resulting formed staple may bear more resemblance and functional similarity to a secure tissue clip than a conventional staple. Such a clip-like configuration may result in more tissue being captured between the legs and the crown of the formed staple than might otherwise be captured between legs (270, 290) and crown (252); which may in turn result in better tissue integrity and a reduced tendency for the tissue to tear near the staple. Minimizing the fold-back motion of the staple legs during the process of staple formation may also reduce the total force required to form the staple using staple forming pocket (610); as compared to the forces required to form a staple using a conventional staple forming pocket. This may reduce the force required to advance firing beam (14) distally during a firing stroke.

Figure 38:
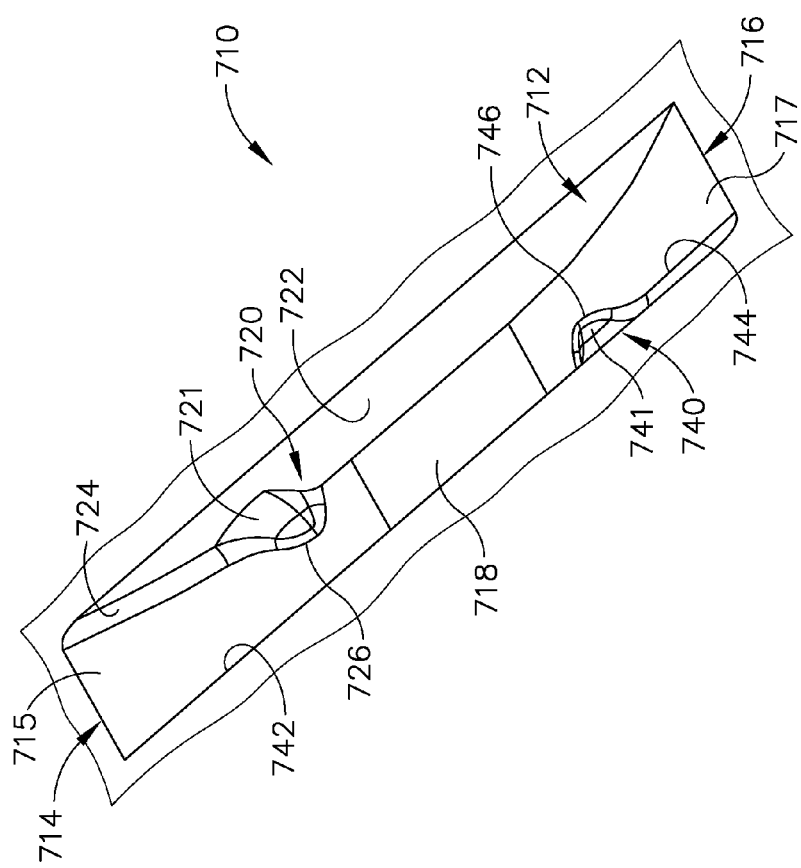
FIG. 38 depicts a perspective view of another exemplary alternative staple forming pocket that may be incorporated in to the anvil of the instrument of FIG. 1.
Figure 39:
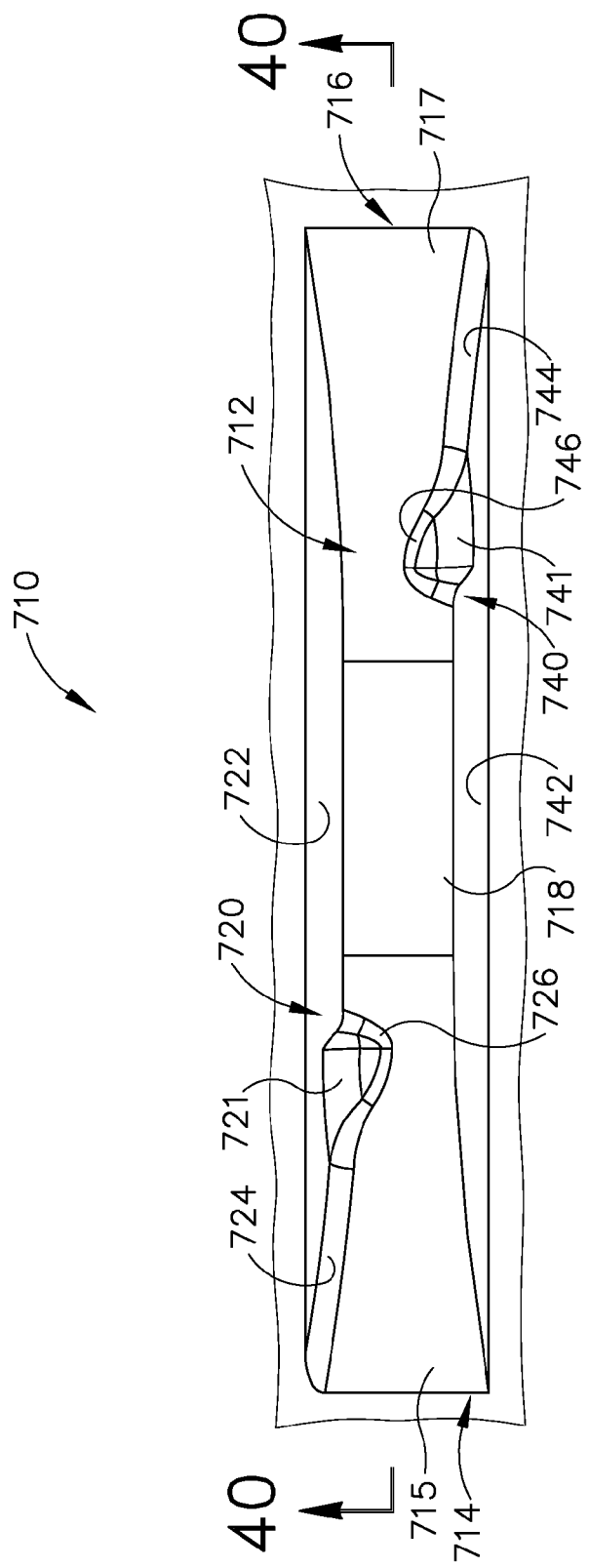
FIG. 39 depicts an enlarged plan view of the staple forming pocket of FIG. 38.
Figure 40:
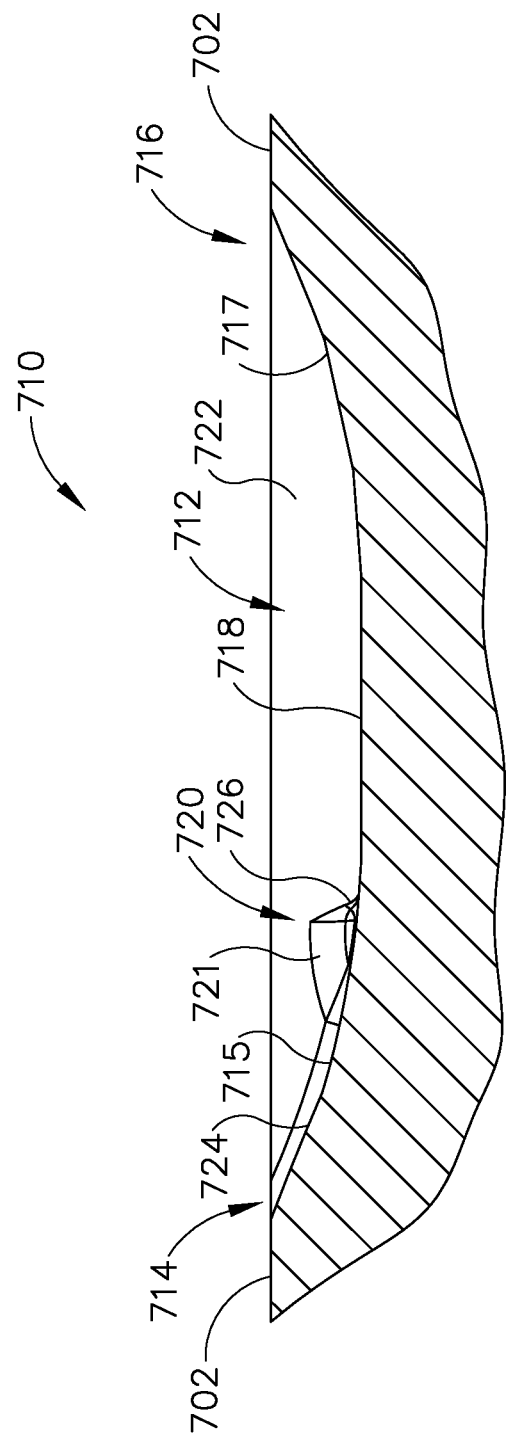
FIG. 40 depicts a cross-sectional view of the staple forming pocket of FIG. 38, taken along line 40-40 of FIG. 39.

F. Exemplary Staple Forming Pockets with Single Channel and Partial Deflection Protrusions FIGS. 38-40 show another merely exemplary staple forming pocket (710) that may be readily incorporated into any of the anvils (18, 200, 300) referred to herein, among others. Staple forming pocket (710) of this example provides a single continuous channel (712) having a first deflection protrusion (720) projecting laterally into channel (712) and a second deflection protrusion (740) projecting laterally into channel (712). Channel (712) includes a first terminal end (714) for receiving a first staple leg and a second terminal end (716) for receiving a second staple leg. Channel (712) includes a concave entry surface (715) at end (714), a concave entry surface (717) at end (716), and a flat floor surface (618) that joins surfaces (715, 717) and provides a lowest point in the longitudinal mid region of channel (712).

Channel (712) is further defined by a first outer sidewall (722) and a second outer sidewall (742). Sidewalls (722, 742) are angled relative to a vertical plane passing longitudinally along the center of staple forming pocket (710), such that sidewalls (722, 742) provide a lead-in to surfaces (715, 717) and floor (718). In other words, the lateral spacing between sidewalls (722, 742) is greater at the top of sidewalls (722, 742) (i.e., at tissue contact surface (702)) than the lateral spacing between sidewalls (722, 742) at the bottom of sidewalls (722, 742).

First deflection protrusion (720) includes an angled upper wall (721), and a laterally angled sidewall (724) leading to a convex sidewall (726), which terminates in first outer sidewall (722) Like sidewall (722), sidewalls (724, 726) are sloped relative to a vertical plane passing longitudinally along the center of staple forming pocket (710), such that sidewalls (724, 726) provide a lead-in to surfaces (715, 717) and floor (718). Upper wall (721) is also sloped relative to a vertical plane passing longitudinally along the center of staple forming pocket (710), though with an angle that is less steep than the angle provided by sidewalls (724, 726). As best seen in FIG. 40, upper wall (721) is positioned below tissue contact surface (702), such that protrusion (720) is entirely recessed in channel (712) in this example.

Second deflection protrusion (740) includes an angled upper wall (741), and a laterally angled sidewall (744) leading to a convex sidewall (746), which terminates in second outer sidewall (742). Like sidewall (742), sidewalls (744, 746) are sloped relative to a vertical plane passing longitudinally along the center of staple forming pocket (710), such that sidewalls (744, 746) provide a lead-in to surfaces (715, 717) and floor (718). Upper wall (741) is also sloped relative to a vertical plane passing longitudinally along the center of staple forming pocket (710), though with an angle that is less steep than the angle provided by sidewalls (744, 746). As best seen in FIG. 40, upper wall (741) is positioned below tissue contact surface (702), such that protrusion (740) is entirely recessed in channel (712) in this example.

When a staple is driven into staple forming pocket (710), the result may be similar to the result shown in FIGS. 24 and 34. In particular, surfaces (715, 717) may drive the legs of the staple toward each other as the staple is initially driven into staple forming pocket (710). Protrusions (720, 740) may eventually deflect the legs of the staple laterally in opposite directions, such that the legs do not collide with each other during formation of the staple and such that the legs are ultimately positioned on opposite sides of a vertical plane passing through the crown of the staple (e.g., as shown in FIG. 34). The tips of the staple legs may ultimately pass through layers (92, 94) of tissue just once, without even passing back through layer (94). In some versions, the tips of the staple legs may at least pass back through layer (94) a second time (e.g., as shown in FIG. 24).

It should be understood that a staple formed by staple forming pocket (710) may provide greater hemostasis of apposed tissue layers (92, 94), may provide greater structural integrity with respect to the apposition of tissue layers (92, 94), may have a reduced likelihood to undesirably pull through tissue layers (92, 94), may provide a reduced likelihood of tissue later tearing at the staple line, and/or may otherwise minimize trauma to tissue layers (92, 94), particularly when compared to staple (250) formed by staple forming pocket (210). When sealing certain tissue structures (e.g., a fragile artery, etc.), it may be desirable to minimize the amount of tissue puncturing by a staple. A staple formed by pocket (710) may minimize such puncturing (e.g., as compared to formed staple (250)) by not passing back trough layer (92) a second time; and in some instances not passing back through layer (94) a second time. By minimizing the fold-back motion of the staple legs formed by staple forming pocket (710), the resulting formed staple may bear more resemblance and functional similarity to a secure tissue clip than a conventional staple. Such a clip-like configuration may result in more tissue being captured between the legs and the crown of the formed staple than might otherwise be captured between legs (270, 290) and crown (252); which may in turn result in better tissue integrity and a reduced tendency for the tissue to tear near the staple. Minimizing the fold-back motion of the staple legs during the process of staple formation may also reduce the total force required to form the staple using staple forming pocket (710); as compared to the forces required to form a staple using a conventional staple forming pocket. This may reduce the force required to advance firing beam (14) distally during a firing stroke.

G. Exemplary Varied Array of Staple Forming Pockets

Figure 41:
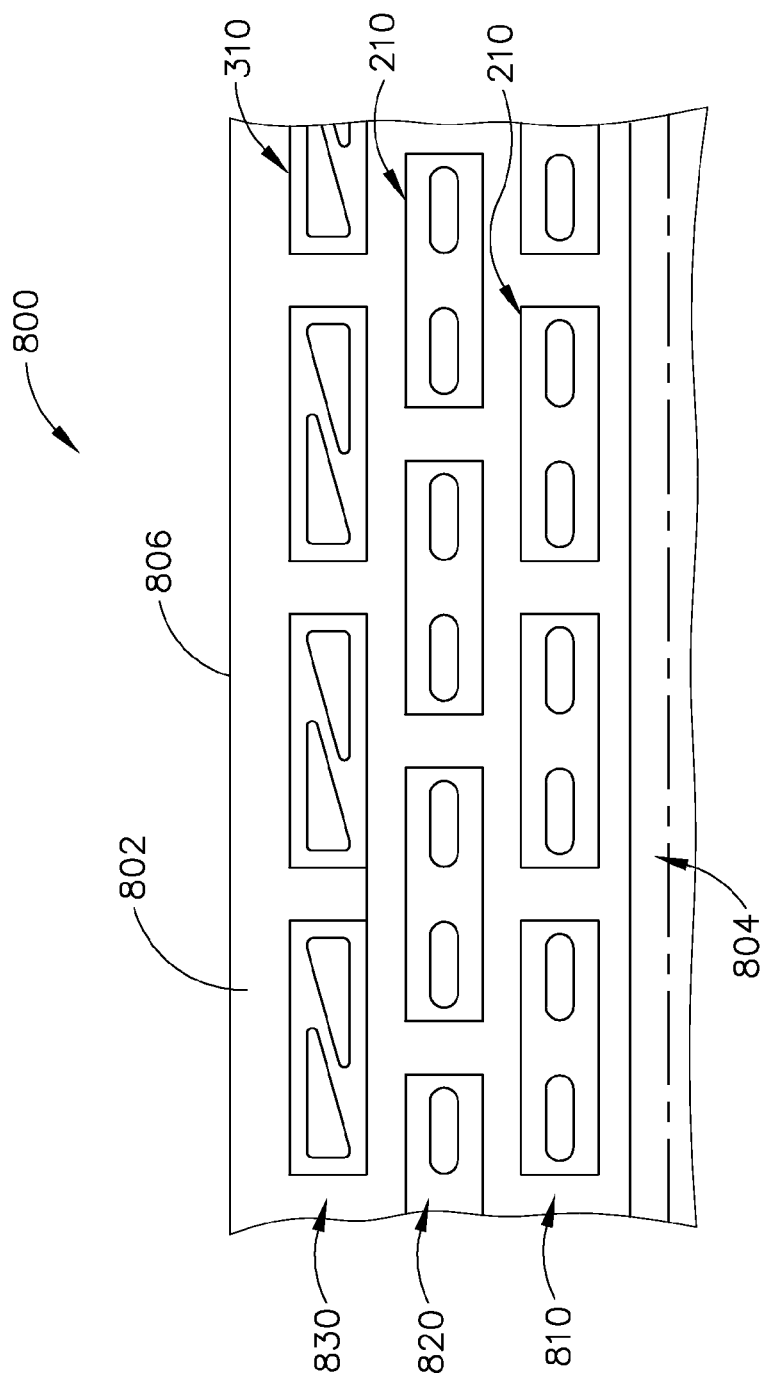
FIG. 41 depicts a bottom elevational view of staple forming pockets on another exemplary alternative anvil that may be incorporated into the instrument of FIG. 1.

In some exemplary anvils, all of the staple forming pockets have the same configuration. In some other exemplary anvils, at least some of the staple forming pockets are different from each other. An example of this is shown in FIG. 41, which shows a portion of an anvil (800) having two rows of a first kind of staple forming pockets (210) and a row of a second kind of staple forming pockets (310). Anvil (800) includes a tissue contact surface (802), an anvil slot (804) (which is similar to anvil slot (42) described above), and an outer side (806). It should be understood that FIG. 41 just shows pockets (210, 310) on one side of slot (804), and that a mirror image arrangement of pockets (210, 310) would be on the other side of slot (804) such that anvil (800) is symmetric about a plane extending perpendicularly out of the drawing sheet along the length of slot (804).

Pockets (210) are the same as pockets (210) shown in FIGS. 12-16 and described above. Pockets (310) are the same as pockets (310) shown in FIGS. 19-23 and described above. Of course, any other suitable pocket configurations may be used. It should also be understood that any suitable arrangement may be used. For instance, a first row (810) may include a first type of staple forming pocket, with a second row (820) including a second type of staple forming pocket, with a third row (830) including a third type of staple forming pocket. As another merely illustrative example, the staple forming pockets of at least one row (810, 820, 830) may be oriented in one direction; while the staple forming pockets of at least one other row (810, 820, 830) may be oriented in another direction. In some versions, the staple forming pockets of one row (810, 820, 830) are oriented obliquely relative to the staple forming pockets of the other rows (810, 820, 830). In addition or the alternative, the staple forming pockets of one row (810, 820, 830) may be oriented perpendicularly relative to the staple forming pockets of the other rows (810, 820, 830). Even the staple forming pockets of a particular row (810, 820, 830) may be oriented differently from other staple forming pockets in the same row (810, 820, 830) (e.g., alternating perpendicular or oblique orientations, etc.). Various suitable arrangements and combinations of pocket configurations will be apparent to those of ordinary skill in the art in view of the teachings here.

Figure 42:
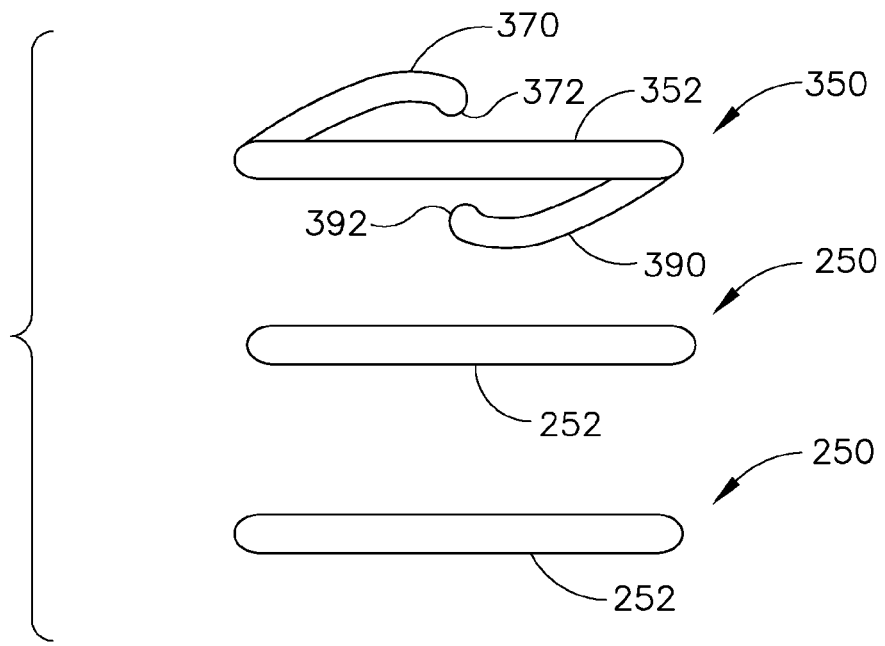
FIG. 42 depicts a top plan view of staples formed by the staple forming pockets of FIG. 41.
Figure 43:
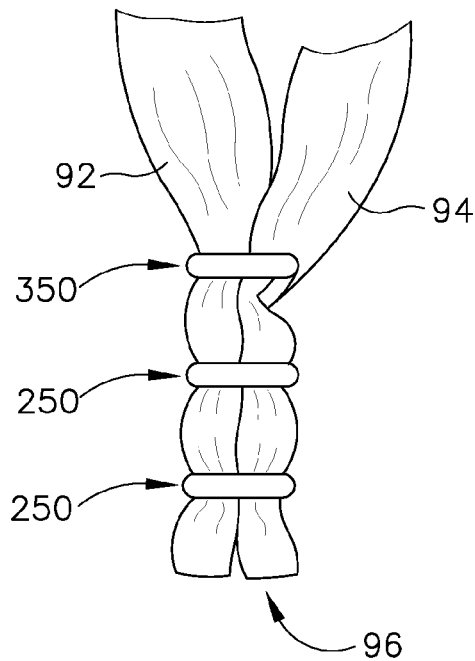
FIG. 43 depicts layers of tissue secured by the staples of FIG. 42.

FIGS. 42-43 show a series of staples (250, 350) formed by anvil (800). Staples (250) are the same as staple (250) shown in FIGS. 17-18E and described above. Staple (350) is the same as staple (350) shown in FIGS. 24-25D and described above. As best seen in FIG. 42, in each formed staple (250), legs (270, 290) remain positioned along a vertical plane passing through crown (252), such that legs (270, 290) are obscured in the top plan view of FIG. 42. However, legs (370, 390) of staple (350) are deflected laterally and obliquely relative to the vertical plane passing through crown (352) of staple (350), due to the configuration of pocket (310) as described above. FIG. 43 depicts these formed staples (250, 350) as applied to layers (92, 94). Since pockets (210) are positioned closest to slot (804), staples (250) are positioned closest to the cut line (96) created by cutting edge (48) of firing beam (14).

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, now U.S. Pat. No. 8,844,789, issued Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued Dec. 31, 2013 as U.S. Pat. No. 8,616,431, the disclosure of which is incorporated by reference herein; U.S. Pub. No. 2012/0199633, entitled "Surgical Stapling Instruments with Cam-Driven Staple Deployment Arrangements," published Aug. 9, 2012, issued Nov. 5, 2013 as U.S.

Pat. No. 8,573,461, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued Dec. 10, 2013 as U.S. Pat. No. 8,602,288, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued Apr. 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued Jul. 9, 2013 as U.S. Pat. No. 8,479,969; U.S. Pub. No. 2012/0138660, entitled "Robotically-Controlled Cable-Based Surgical End Effectors," published Jun. 7, 2012, now U.S. Pat. No. 8,800,838, issued Aug. 12, 2017, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued Nov. 5, 2013 as U.S. Pat. No. 8,573,465, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An end effector of a surgical instrument, the end effector comprising:
    (a) a first jaw, wherein the first jaw is configured to receive a staple cartridge; and
    (b) a second jaw, wherein the second jaw is movable relative to the first jaw, wherein the second jaw is configured to provide an anvil for forming staples driven from a staple cartridge received in the first jaw, wherein the anvil comprises:
        (i) a tissue contacting surface, and
        (ii) a staple forming pocket adjacent to the tissue contacting surface, wherein the staple forming pocket defines a length along a longitudinal axis, wherein the staple forming pocket comprises:
            (A) a first staple forming surface region configured to receive a first staple leg, wherein the first staple forming surface region defines a first sidewall, a second sidewall, a third sidewall, and a fourth sidewall,
                wherein the first staple forming surface region is laterally defined on a first side by the first, second and third sidewall portions and on a second side by the fourth sidewall portion,
                wherein the first sidewall of the first staple forming surface region has a shorter length than the second sidewall,
                wherein the first side of the first staple forming surface region is positioned opposite of the second side of the first staple forming surface region, and
            (B) a second staple forming surface region configured to receive a second staple leg, wherein the second staple forming surface region defines a first sidewall, a second sidewall, a third sidewall, and a fourth sidewall,
                wherein the second staple forming surface region is laterally defined on a first side by the first, second and third sidewall portions and on a second side by the fourth sidewall portion,
                wherein the first sidewall of the second staple forming surface region has a shorter length than the second sidewall,
                wherein the first side of the second staple forming surface region is positioned opposite of the second side of the second staple forming surface region, and
            (C) a dividing structure located between the first staple forming surface region and the second staple forming surface region,
                wherein the third sidewall of the first staple forming surface region and third sidewall of the second staple forming surface region abut one another to thereby define the dividing structure; and
                wherein the first sidewall portion of each of the first and second staple forming surface region has a first length, wherein the second sidewall portion of each of the first and second staple forming surface region has a second length, wherein the third sidewall portion of each of the first and second staple forming surface region has a third length, wherein the fourth sidewall portion of each of the first and second staple forming surface region has a fourth length, wherein the first length is less than the second length, wherein the third length is less than the fourth length.

2. The end effector of claim 1, wherein the first staple forming surface region is defined within a first channel, wherein the second staple forming surface region is defined within a second channel.

3. The end effector of claim 2, wherein the dividing structure separates the first channel from the second channel.

4. The end effector of claim 1, wherein the dividing structure is obliquely oriented relative to the longitudinal axis of the staple forming pocket.

5. The end effector of claim 4, wherein the first sidewall portion of each of the first and second staple forming surface region defines a first angle relative to the longitudinal axis of the staple forming pocket, wherein the second sidewall portion of each of the first and second staple forming surface region defines a second angle relative to the longitudinal axis of the staple forming pocket, wherein the first angle is greater than the second angle.

6. The end effector of claim 5, wherein the third sidewall portion of each of the first and second staple forming surface region defines a third angle relative to the longitudinal axis of the staple forming pocket, wherein the fourth sidewall portion of each of the first and second staple forming surface region defines a fourth angle relative to the longitudinal axis of the staple forming pocket, wherein the third angle is greater than the fourth angle.

7. The end effector of claim 6, wherein the first angle is equal to the third angle.

8. The end effector of claim 7, wherein the second angle is equal to the fourth angle.

9. The end effector of claim 1, wherein the first channel terminates at a region along the length of the staple forming pocket that is common with the region along the length of the staple forming pocket where the third sidewall portion of each of the first and second staple forming surface region transitions to the fourth sidewall portion of each of the first and second staple forming surface region, wherein the second channel terminates at a region along the length of the staple forming pocket that is common with the region along the length of the staple forming pocket where the first sidewall portion of each of the first and second staple forming surface region transitions to the second sidewall portion of each of the first and second staple forming surface region.

10. An end effector of a surgical instrument, the end effector comprising:
(a) a first jaw, wherein the first jaw is configured to receive a staple cartridge; and
(b) a second jaw, wherein the second jaw is pivotable relative to the first jaw, wherein the second jaw is configured to provide an anvil for forming staples driven from a staple cartridge received in the first jaw, wherein the second jaw comprises:
(i) a tissue contacting surface, and
(ii) a staple forming pocket adjacent to the tissue contacting surface, wherein the staple forming pocket defines a length along a longitudinal axis, wherein the staple forming pocket comprises:
(A) a first staple forming surface region configured to receive a first staple leg, wherein the first staple forming surface region includes a first convex surface configured to drive a staple leg laterally relative to the longitudinal axis, wherein the first staple forming surface region defines a first sidewall, a second sidewall, a third sidewall, and a fourth sidewall, and
(B) a second staple forming surface region configured to receive a second staple leg, wherein the second staple forming surface region includes a second convex surface configured to drive a staple leg laterally relative to the longitudinal axis, wherein the second staple forming surface region defines a first sidewall, a second sidewall, a third sidewall, and a fourth sidewall;
wherein the first sidewalls of each of the first and second staple forming surface regions are separated by the second sidewalls of each of the first and second staple forming surface regions by a first transition portion and extend parallel to one another and parallel to the longitudinal axis;
wherein the third sidewalls of each of the first and second staple forming surface regions are separated by the second sidewalls of each of the first and second staple forming surface regions by a second transition portion and extend parallel to one another and obliquely relative to the longitudinal axis;
wherein the fourth sidewalls of each of the first and second staple forming surface regions extend along a side facing the first, second and third sidewall portions of each of the first and second staple forming surface regions and extend obliquely relative to the longitudinal axis but at a different angle than the third sidewalls.

11. An end effector of a surgical instrument, the end effector comprising:
(a) a first jaw, wherein the first jaw is configured to receive a staple cartridge; and
(b) a second jaw, wherein the second jaw is pivotable relative to the first jaw, wherein the second jaw is configured to provide an anvil for forming staples driven from a staple cartridge received in the first jaw, wherein the second jaw comprises:
(i) a tissue contacting surface, and
(ii) a staple forming pocket adjacent to the tissue contacting surface, wherein the staple forming pocket defines a length along a longitudinal axis, wherein the longitudinal axis extends along the length of the staple forming pocket through a laterally central region of the staple forming pocket, wherein the staple forming pocket comprises:
(A) a first region configured to receive a first staple leg, wherein the first region includes a first surface region configured to drive a staple leg laterally relative to the longitudinal axis,
(B) a second region configured to receive a second staple leg, wherein the second region includes a second surface region configured to drive a staple leg laterally relative to the longitudinal axis, wherein parts of the first and second regions extend along a common range of the length of the staple forming pocket such that portions of the first and second regions are positioned lateral to each other, and
(C) a dividing wall located between the first staple forming surface region and the second staple forming surface region,
wherein the dividing wall is defined by a first sidewall portion, and a second sidewall portion, wherein the first sidewall portion further defines an inner side of the first staple forming surface region, wherein the second sidewall portion defines an inner side of the second staple forming surface region, and wherein the first and second sidewall portions are parallel with each other and are oblique with the longitudinal axis of the staple forming pocket;

wherein the first sidewall portion includes a third sidewall portion extending obliquely therefrom to further define the inner side of the first staple forming surface region;

wherein the second sidewall portion includes a fourth sidewall portion extending obliquely therefrom to further define the inner side of the second staple forming surface region;

wherein the fourth sidewalls of each of the first and second staple forming regions are laterally opposite of the first sidewall, second sidewall, and third sidewall of the respective staple forming regions to define the staple forming pocket;

wherein the first, second, third and fourth sidewalls are defined by substantially straight surfaces; and wherein a first transition member connects the first sidewall to the second sidewall and a second transition member connects the second sidewall to the third sidewall.

\* \* \* \* \*